United States Patent
Che et al.

(10) Patent No.: US 11,319,338 B2
(45) Date of Patent: May 3, 2022

(54) TIMOSAPONIN COMPOUNDS

(71) Applicants: Chiming Che, Hong Kong (CN);
Laiking Sy, Hong Kong (CN);
Chunnam Lok, Hong Kong (CN)

(72) Inventors: Chiming Che, Hong Kong (CN);
Laiking Sy, Hong Kong (CN);
Chunnam Lok, Hong Kong (CN)

(73) Assignee: GoldPorp Pharma Limited, Hong Kong (HK)

( * ) Notice: Subject to any disclaimer, the term of this patent is extended or adjusted under 35 U.S.C. 154(b) by 987 days.

(21) Appl. No.: 14/390,400

(22) PCT Filed: Apr. 2, 2013

(86) PCT No.: PCT/CN2013/073666
§ 371 (c)(1),
(2) Date: Oct. 3, 2014

(87) PCT Pub. No.: WO2013/149580
PCT Pub. Date: Oct. 10, 2013

(65) Prior Publication Data
US 2015/0050367 A1 Feb. 19, 2015

Related U.S. Application Data

(60) Provisional application No. 61/619,439, filed on Apr. 3, 2012.

(51) Int. Cl.
| | |
|---|---|
| *A61P 25/00* | (2006.01) |
| *A61P 25/16* | (2006.01) |
| *A61P 25/28* | (2006.01) |
| *A61K 31/7048* | (2006.01) |
| *A61K 31/58* | (2006.01) |
| *A61K 45/06* | (2006.01) |
| *C07J 71/00* | (2006.01) |

(52) U.S. Cl.
CPC ........... *C07J 71/0031* (2013.01); *A61K 31/58* (2013.01); *A61K 31/7048* (2013.01); *A61K 45/06* (2013.01); *C07J 71/0005* (2013.01)

(58) Field of Classification Search
CPC .......... A61P 25/00; A61P 25/16; A61P 25/28; A61K 31/7048; A61K 31/58; A61K 45/06; C07J 71/0005; C07J 71/0031
See application file for complete search history.

(56) References Cited

U.S. PATENT DOCUMENTS 6,593,301 B1 7/2003 Ma et al.
7,138,427 B2 * 11/2006 Barraclough ........ C07J 71/0005
514/453

FOREIGN PATENT DOCUMENTS

| CN | 101768202 A | * | 7/2010 |
| WO | 01/23406 A1 | | 4/2001 |
| WO | 01/23408 A1 | | 4/2001 |
| WO | WO 0149703 A2 | | 7/2001 |
| WO | 03/082893 A2 | | 10/2003 |

OTHER PUBLICATIONS

Kawasaki et al., 1964, caplus an 1964:45971.*
Bite et al., 1967, caplus an 1967:38204.*
Wulff et al., 1972, caplus an 1972:154081.*
Pilipenko et al., 2000, caplus an 2000:807981.*
El-Sayed, 1998, caplus an 1998:264542.*
Shchelochkova et al., 1980, caplus an 1980:639839.*
Kobayashi et al., 1994, caplus an 1994:50089.*
Gu et al., 2010, J. Clin. Biochem. Nutr., 46, 269-276.*
Liang et al., 1935, caplus an 1935:22879.*
Gohil et al., 2010, caplus an 2010:201423.*
Gohil et al. full reference, 2010, Nature Biotechnology, 28(3), 249-255.*
RN314755-68-5, registry database compound, entry date Jan. 18, 2001.*
CN101768202-machine-translation, 2019, machine translation of CN101768202.*
Song et al., 2010, caplus an 2010:863713.*
RN4965-85-9, registry database compound, entry date Nov. 16, 1984.*
Harris et al., 2004, International Congress Series, 1262, 380-383.*
Bennett et al., 1963, caplus an 1963:410277.*
Fu et al., 2011, caplus an 2011:1682457.*
Paseshnichenko et al., 1975, caplus an 1975:125560.*
RN1402423-11-3, 2012, registry database compound.*
RN156590-67-9, 1994, registry database compound.*
International Search Report (ISR).
International Written Opinion.
Registry-1 (Provided by ISA/CN with the ISR).
Registry-2 (Provided by ISA/CN with the ISR).
Registry-3 (Provided by ISA/CN with the ISR).
Deng Yun, et al., Protective effects of timosaponin BII on primary neurons against beta amyloid peptide 25-35, Chinese Pharmacological Bulletin, Feb. 2009, vol. 25, No. 2, pp. 244-247 (with an English Abstract).

* cited by examiner

*Primary Examiner* — Sun Jae Yoo
(74) *Attorney, Agent, or Firm* — Squire Patton Boggs (US) LLP

(57) ABSTRACT

Provided herein are timosaponin compounds of Formula I, II, III, I', II' and III', pharmaceutical compositions comprising the compounds, and processes of preparation thereof. Also provided are uses of said timosaponin compounds for preparing medicament for the treatment of diseases associated with beta-amyloid in hosts or subjects in need thereof.

13 Claims, 20 Drawing Sheets

(a) AlCl$_3$, LiAlH$_4$, ether, reflux
(b) Methyl sulfonation
(c) Reduction

R = sugar

Sarsasapogenin (a) AlCl$_3$, LiAlH$_4$, ether, reflux
(b) Methyl sulfonation
(c) Reduction (a) PivCl, pyridine, 0°C
(b) AgOTf, 4 Å MS, CH₂Cl₂, -16°C
(c) BF₃·OEt₂, 4 Å MS, room temperature
(d) NaOH, MeOH-H₂O-THF (1:1:1), 40°C

TIMOSAPONIN COMPOUNDS

CROSS-REFERENCE TO RELATED APPLICATIONS

This is a U.S. national stage application of the International Patent Application No. PCT/CN2013/073666, filed 2 Apr. 2013, which claims priority to U.S. Provisional Application No. 61/619,439, filed 3 Apr. 2012, both of which are incorporated herein by reference in their entirety.

FIELD OF THE INVENTION

Provided herein are timosaponin compounds, pharmaceutical compositions comprising the compounds, and processes of preparation thereof. Also provided are methods of their use for the treatment of diseases associated with beta-amyloid in hosts or subjects in need thereof.

BACKGROUND OF THE INVENTION

Saponins, literally foaming substances, are generally secondary metabolites consists of hydrophilic sugar attached to hydrophobic aglycone of steroid or triterpenoid. Many biologically active saponins have been isolated from traditional Chinese medicinal herbs. However, comparing to other natural products such as flavones, the therapeutic applications of saponins are less explored.

Timosaponins are a group of steroidal saponins with the sugar moiety (monosaccharide, disaccharide or polysaccharide) attached to the $C_3$ position of the aglycone, i.e., sarsasapogenin. Timosaponins can be isolated from the medicinal herb *Anemarrhena asphodeloides* (Zhimu in Chinese) which is a commonly used traditional Chinese medicine (TCM) listed in Schedule 2 in Chinese Medicine Ordinance (Chapter 549, Law of Hong Kong). The standardization work including qualitative and quantitative control of *Anemarrhena asphodeloides* is published in Hong Kong Chinese Materia Medica Standards by Department of Health (HKCMMS, Volume III, p 255, 2010). *Anemarrhena asphodeloides* is also officially listed in Chinese Pharmacopoeia (2010, Volume I, English version) as a medicine for treating febrile diseases. Some experimental evidence shows that sarsasapogenin, timosaponins, or the Zhimu extracts exhibit various pharmacological properties, including anti-pyretic, anti-inflammatory, anti-diabetic, anti-depressive activities and improvement of learning and memory. Despite of these interesting findings, the mechanism of action and pharmacological applications of timosaponins for the treatment of diseases associated with beta-amyloid remain unknown.

Currently, there is no curative treatment for some diseases associated with beta-amyloid such as the Alzheimer's disease. There is only symptomatic treatment for the cognitive manifestations of Alzheimer's disease using acetyl cholinesterase inhibitors and N-methyl-D-aspartate receptor antagonists. In view of several failure in Phase III clinical trials on patients with progressing Alzheimer's disease, the current therapeutics are developed with an emphasis on safe prophylactic intervention to lower Aβ levels in presymptomatic stage. Therefore, there is a clear and unmet need to develop effective therapeutics for treating or preventing diseases associated with beta-amyloid.

SUMMARY OF THE INVENTION

Provided herein are timosaponin compounds, pharmaceutical compositions comprising the compounds, and processes of preparation thereof. Also provided are methods of their use for the treatment of diseases associated with beta-amyloid in hosts in need thereof.

In one aspect, provided herein is a compound of Formula I:

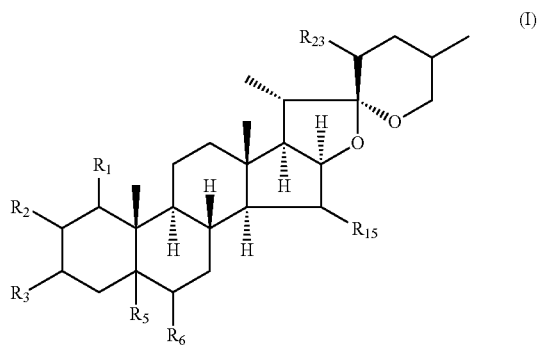

or a single enantiomer, a mixture of an enantiomeric pair, an individual diastereomer, or a mixture of diastereomers; or a pharmaceutically acceptable salt, solvate, or prodrug thereof, wherein:

each of $R_1$, $R_2$, $R_3$, $R_{15}$, and $R_{23}$ is independently H, OH, oxo, O-acyl, halo, O-alkyl, $OSO_3H$, $OSO_3Na$, $N_3$, $NH_2$, NHR, NRR', $NHSO_2R$, SR, SOR, $SO_2R$, $OPO_3H_2$, $OPO_3HNa$, $OPO_3Na_2$, O-monosacharride, O-disaccharide or O-oligosaccharide; and each of $R_5$ and $R_6$ is independently H, OH, O-acyl, halo, $OSO_3H$, O-alkyl, $OSO_3H$, $OSO_3Na$, $N_3$, $NH_2$, NHR, NRR', $NHSO_2R$, SR, SOR, $SO_2R$, $OPO_3H_2$, $OPO_3HNa$, $OPO_3Na_2$, epoxy, O-monosacharride, O-disaccharide or O-oligosaccharide, or $R_5$ and $R_6$ together form a double bond, where each of R and R' independently is alkyl (e.g., methyl), aryl, arylalkyl, alkaryl, heteroaryl, alkenyl, alkynyl, cycloalkyl, or heterocyclyl.

In some embodiments, the compound of Formula I has Formula I':

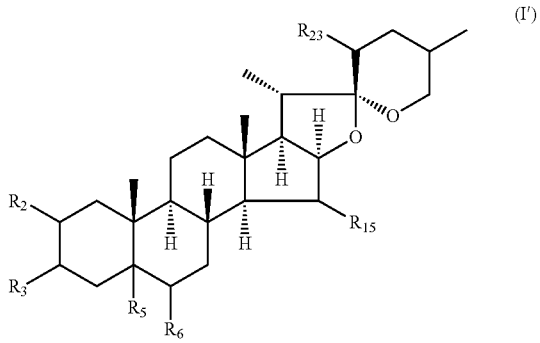

or a single enantiomer, a mixture of an enantiomeric pair, an individual diastereomer, or a mixture of diastereomers; or a pharmaceutically acceptable salt, solvate, or prodrug thereof, wherein:

$R_2$ is H or OH;

$R_3$ is OH, O-β-galactosyl, O-β-glucosyl(1→2)-β-Gal, O-β-mannosyl(1→2)-β-glucosyl, O-β-glucosyl(1→2)-O-[β-xylosyl(1→3)]-O-β-glucosyl(1→4)-β-galactosyl, O-β-glucosyl(1→2)-β-galactosyl, O-α-6-deoxy-mannosyl(1→2)-O-[α-6-deoxy-mannosyl(1→4)]-β-glucosyl, O-α- arabinosyl(1→4)-O-[α-6-deoxy-mannosyl(1→2)]-β-glucosyl or O-β-glucosyl(1→2)-O-[α-6-deoxy-mannosyl(1→2)]-O-β-glucosyl;

each of $R_5$ and $R_6$ is H, or $R_5$ and $R_6$ together form a double bond;

$R_{15}$ is H, OH or R; and $R_{23}$ is H, OH or SH, where each of R and R' independently is alkyl (e.g., methyl), aryl, arylalkyl, alkaryl, heteroaryl, alkenyl, alkynyl, cycloalkyl, or heterocyclyl.

In another aspect, provided herein is a compound of Formula II:

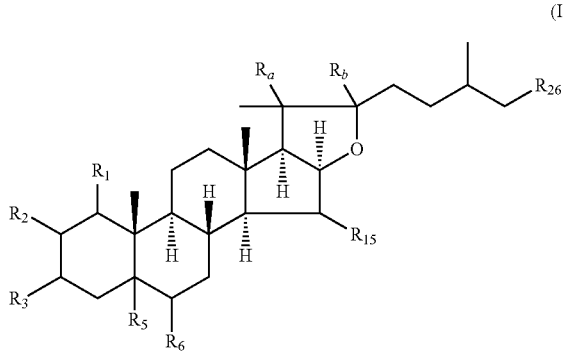

(II)

or a single enantiomer, a mixture of an enantiomeric pair, an individual diastereomer, or a mixture of diastereomers; or a pharmaceutically acceptable salt, solvate, or prodrug thereof, wherein:

each of $R_1$, $R_2$, $R_3$, and $R_{15}$ is independently H, OH, oxo, O-acyl, halo, O-alkyl, $OSO_3H$, $OSO_3Na$, $N_3$, $NH_2$, NHR, NRR', $NHSO_2R$, SR, SOR, $SO_2R$, $OPO_3H_2$, $OPO_3HNa$, $OPO_3Na_2$, O-monosacharride, O-disaccharide or O-oligosaccharide;

each of $R_5$ and $R_6$ is independently H, OH, O-acyl, halo, $OSO_3H$, O-alkyl, $OSO_3H$, $OSO_3Na$, $N_3$, $NH_2$, NHR, NRR', $NHSO_2R$, SR, SOR, $SO_2R$, $OPO_3H_2$, $OPO_3HNa$, $OPO_3Na_2$, epoxy, O-monosacharride, O-disaccharide or O-oligosaccharide, or $R_5$ and $R_6$ together form a double bond;

each of $R_a$ and $R_b$ is independently H, OH, O-acyl, halo, $OSO_3H$, O-alkyl, $OSO_3H$, $OSO_3Na$, $N_3$, $NH_2$, NHR, NRR', $NHSO_2R$, SR, SOR, $SO_2R$, $OPO_3H_2$, $OPO_3HNa$, $OPO_3Na_2$, epoxy, O-monosacharride, O-disaccharide or O-oligosaccharide, or $R_a$ and $R_b$ together form a double bond; and $R_{26}$ is OH, O-acyl, halo, O-alkyl, $OSO_3H$, $OSO_3Na$, $N_3$, $NH_2$, NHR, NRR', $NHSO_2R$, SR, SOR, $SO_2R$, $OPO_3H_2$, $OPO_3HNa$, $OPO_3Na_2$, CHO, carboxy, $CONH_2$, CONHR, CONRR', C(=O)O-akyl, O—C(=O)-alkyl, O-monosacharride, O-disaccharide or O-oligosaccharide, where each of R and R' independently is alkyl (e.g., methyl), aryl, arylalkyl, alkaryl, heteroaryl, alkenyl, alkynyl, cycloalkyl, or heterocyclyl.

In some embodiments, the compound of Formula II has Formula II':

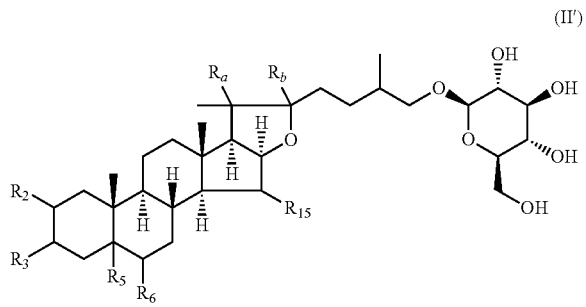

(II')

or a single enantiomer, a mixture of an enantiomeric pair, an individual diastereomer, or a mixture of diastereomers; or a pharmaceutically acceptable salt, solvate, or prodrug thereof, wherein:

$R_2$ is H or OH;

$R_3$ is O-β-glucosyl(1→2)-β-galactosyl, galactosyl, H, O-β-glucosyl(1→2)-O-[β-glucosyl(1→3)]-O-β-glucosyl (1→4)-β-galactosyl, O-β-glucosyl(1→2)-→-glucosyl or O-β-glucosyl(1→2)-O-[β-xylosyl(1→3)]-O-β-glucosyl (1→4)-β-galactosyl;

$R_5$ is H; $R_6$ is H or OH, or $R_5$ and $R_6$ together form a double bond;

$R_{15}$ is H or OH;

$R_a$ is H; and $R_b$ is OR or OH, or $R_a$ and $R_b$ together form a double bond, where each of R and R' independently is alkyl (e.g., methyl), aryl, arylalkyl, alkaryl, heteroaryl, alkenyl, alkynyl, cycloalkyl, or heterocyclyl.

In one aspect, provided herein is a compound of Formula III:

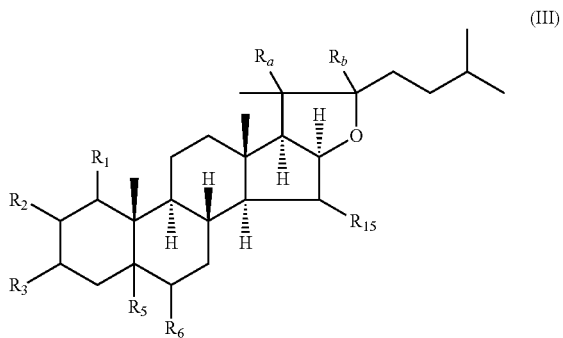

(III)

or a single enantiomer, a mixture of an enantiomeric pair, an individual diastereomer, or a mixture of diastereomers; or a pharmaceutically acceptable salt, solvate, or prodrug thereof, wherein:

each of $R_1$, $R_2$, $R_3$, $R_{15}$, and $R_b$ is independently H, OH, oxo, O-acyl, halo, O-alkyl, $OSO_3H$, $OSO_3Na$, $N_3$, $NH_2$, NHR, NRR', $NHSO_2R$, SR, SOR, $SO_2R$, $OPO_3H_2$, $OPO_3HNa$, $OPO_3Na_2$, O-monosacharride, O-disaccharide or O-oligosaccharide;

each of $R_5$ and $R_6$ is independently H, OH, O-acyl, halo, $OSO_3H$, O-alkyl, $OSO_3H$, $OSO_3Na$, $N_3$, $NH_2$, NHR, NRR', $NHSO_2R$, SR, SOR, $SO_2R$, $OPO_3H_2$, $OPO_3HNa$, $OPO_3Na_2$, epoxy, O-monosacharride, O-disaccharide or O-oligosaccharide, or $R_5$ and $R_6$ together form a double bond;

$R_a$ is alkyl (e.g., methyl); and $R_b$ is H, OH, O-acyl, halo, $OSO_3H$, O-alkyl, $OSO_3H$, $OSO_3Na$, $N_3$, $NH_2$, NHR, NRR', $NHSO_2R$, SR, SOR, $SO_2R$, $OPO_3H_2$, $OPO_3HNa$, $OPO_3Na_2$, epoxy, O-monosacharride, O-disaccharide or O-oligosaccharide, or $R_a$ and $R_b$ together form a double bond;

where each of R and R' independently is alkyl (e.g., methyl), aryl, arylalkyl, alkaryl, heteroaryl, alkenyl, alkynyl, cycloalkyl, or heterocyclyl.

In some embodiments, the compound of Formula III has Formula III':

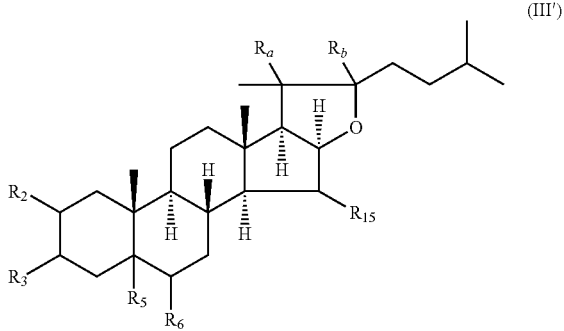

(III')

or a single enantiomer, a mixture of an enantiomeric pair, an individual diastereomer, or a mixture of diastereomers; or a pharmaceutically acceptable salt, solvate, or prodrug thereof, wherein:

$R_2$ is H;

$R_3$ is O-β-glucosyl(1→2)-β-galactosyl;

each of $R_5$ and $R_6$ is H;

$R_{15}$ is OH;

$R_a$ is R; and $R_b$ is OH or OR, where each of R and R' independently is alkyl (e.g., methyl), aryl, arylalkyl, alkaryl, heteroaryl, alkenyl, alkynyl, cycloalkyl, or heterocyclyl.

Also provided herein is a pharmaceutical composition comprising a compound disclosed herein, e.g., a compound of Formula I, II, III, I', II' or III', including a single enantiomer, a mixture of an enantiomeric pair, an individual diastereomer, or a mixture of diastereomers thereof; or a pharmaceutically acceptable salt, solvate, or prodrug thereof; in combination with one or more pharmaceutically acceptable excipients or carriers.

Also provided herein is a method treating or preventing a disease associated with beta-amyloid, which comprises administering to a subject a therapeutically effective amount of a compound disclosed herein, e.g., a compound of Formula I, II, III, I', II' or III', including a single enantiomer, a mixture of an enantiomeric pair, an individual diastereomer, or a mixture of diastereomers thereof; or a pharmaceutically acceptable salt, solvate, or prodrug thereof.

Provided is a compound disclosed herein, e.g., a compound of Formula I, II, III, I', II' or III', or a pharmaceutical composition thereof, for use in therapy. Also provided is a compound disclosed herein, e.g., a compound of Formula I, II, III, I', II' or III', or a pharmaceutical composition thereof, for use in treating or preventing a disease associated with beta-amyloid. Also provided is the use of a compound disclosed herein, e.g., a compound of Formula Formula I, II, III, I', II' or III', or a pharmaceutical composition thereof, for manufacture of a medicament for treating or preventing a disease associated with beta-amyloid.

DETAILED DESCRIPTION OF THE INVENTION

Figure 1:
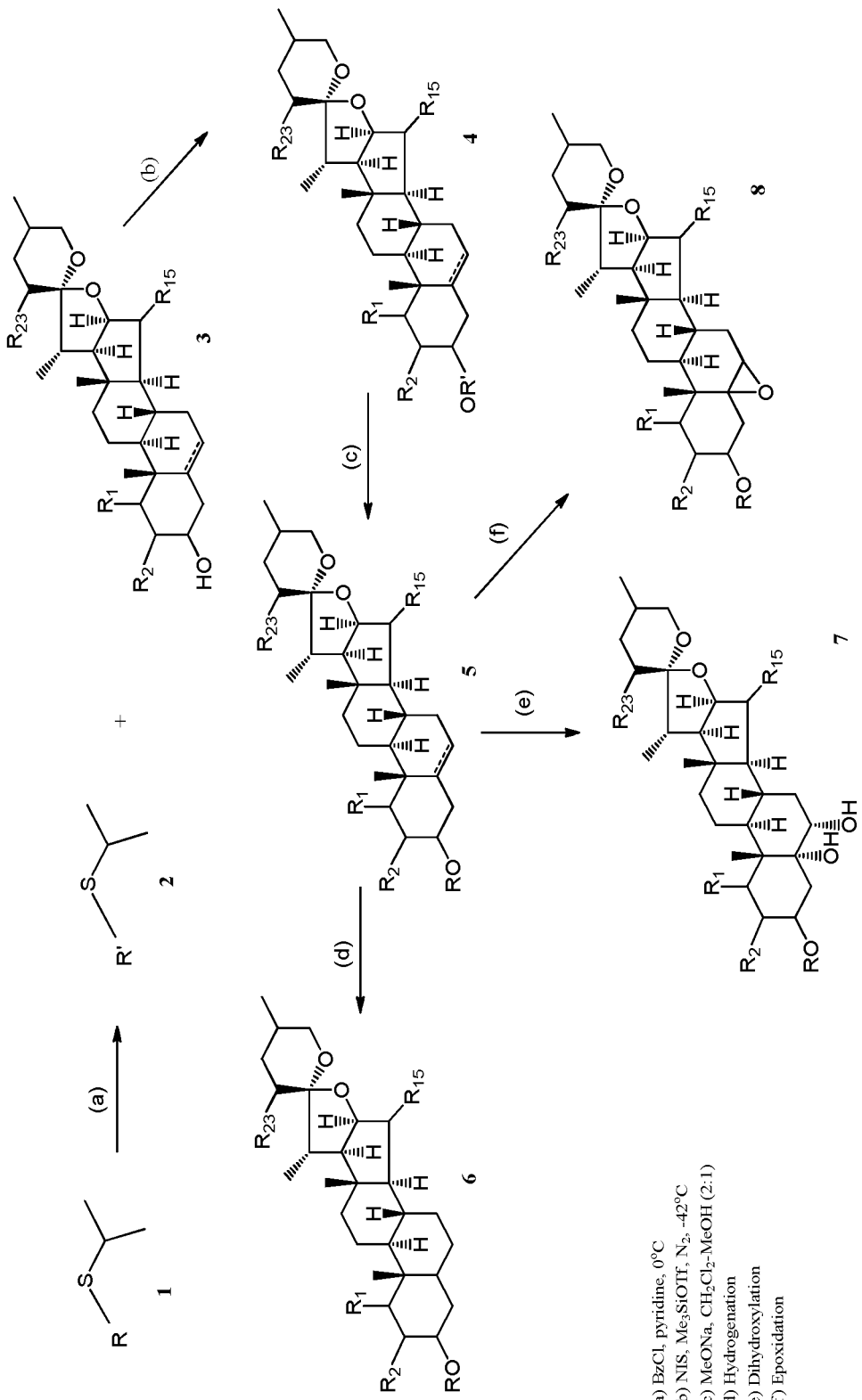
FIG. 1 depicts a general synthetic scheme for synthesizing compounds 5-8 of Formula I.

To facilitate understanding of the disclosure set forth herein, a number of terms are defined below.

Generally, the nomenclature used herein and the laboratory procedures in organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs. In the event that there is a plurality of definitions for a term used herein, those in this section prevail unless stated otherwise.

The term "subject" refers to an animal, including, but not limited to, a primate (e.g., human), cow, sheep, goat, horse, dog, cat, rabbit, rat, or mouse. The terms "subject" and "patient" are used interchangeably herein in reference, for example, to a mammalian subject, such as a human subject.

The term "host" refers to a unicellular or multicellular organism in which a virus can replicate, including, but not limited to, a cell, cell line, and animal, such as human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disease; or reducing a subject's risk of acquiring a disorder, disease, or condition.

The term "therapeutically effective amount" are meant to include the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a cell, tissue, system, animal, or human, which is being sought by a researcher, veterinarian, medical doctor, or clinician.

The term "$IC_{50}$" refers an amount, concentration, or dosage of a compound that is required for 50% inhibition of a maximal response in an assay that measures such response.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, excipient, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 21st Edition; Lippincott Williams & Wilkins: Philadelphia, Pa., 2005; *Handbook of Pharmaceutical Excipients,* 5th Edition; Rowe et al., Eds., The Pharmaceutical Press and the American Pharmaceutical Association: 2005; and *Handbook of Pharmaceutical Additives,* 3rd Edition; Ash and Ash Eds., Gower Publishing Company: 2007; *Pharmaceutical Preformulation and Formulation,* Gibson Ed., CRC Press LLC: Boca Raton, Fla., 2004).

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "active ingredient" and "active substance" refer to a compound, which is administered, alone or in combination with one or more pharmaceutically acceptable excipients, to a subject for treating, preventing, or ameliorating one or more symptoms of a disorder or disease. As used herein, "active ingredient" and "active substance" may be an optically active isomer of a compound described herein.

The terms "drug," "therapeutic agent," and "chemotherapeutic agent" refer to a compound, or a pharmaceutical composition thereof, which is administered to a subject for treating, preventing, or ameliorating one or more symptoms of a condition, disorder, or disease.

The term "release controlling excipient" refers to an excipient whose primary function is to modify the duration or place of release of an active substance from a dosage form as compared with a conventional immediate release dosage form.

The term "nonrelease controlling excipient" refers to an excipient whose primary function do not include modifying the duration or place of release of an active substance from a dosage form as compared with a conventional immediate release dosage form.

The term "monosaccharide" refers to the simplest form of sugar. Some non-limiting examples of suitable monosaccharides include glucose (dextrose), fructose (levulose), galactose, xylose, ribose, mannose and combinations thereof.

The term "disaccharide" refers to the carbohydrate formed when two monosaccharides undergo a condensation reaction which involves the elimination of a small molecule, such as water, and formation of a glycosidic bond. Some non-limiting examples of suitable disaccharides include sucrose, lactose, maltose, trehalose, cellobiose and combinations thereof.

The term "polysaccharide" or "oligosaccharide" refers to long carbohydrate molecules of repeated monomer units joined together by glycosidic bonds. They may range in structure from linear to highly branched. Some non-limiting examples of suitable polysaccharides or oligosaccharides include starch, glycogen, cellulose, chitin and combinations thereof.

The term "simple sugar" refers to a monosaccharide or a disaccharide.

The term "alkyl" refers to a linear or branched saturated monovalent hydrocarbon radical. The term "alkyl" also encompasses both linear and branched alkyl, unless otherwise specified. In certain embodiments, the alkyl is a linear saturated monovalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. In certain embodiments, the alkyl is a linear or branched saturated monovalent hydrocarbon radical that has at least 1, 2, 3, 4, 5, 6, 7, 8, 9, or 10 carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, t-butyl, pentyl (including all isomeric forms), and hexyl (including all isomeric forms). For example, $C_{1-6}$ alkyl refers to a linear saturated monovalent hydrocarbon radical of 1 to 6 carbon atoms or a branched saturated monovalent hydrocarbon radical of 3 to 6 carbon atoms. In certain embodiments, the alkyl may be substituted.

The term "alkenyl" refers to a linear or branched monovalent hydrocarbon radical, which contains one or more carbon-carbon double bonds. The alkenyl may be optionally substituted, e.g., as described herein. The term "alkenyl" also embraces radicals having "cis" and "trans" configurations, or alternatively, "E" and "Z" configurations, as appreciated by those of ordinary skill in the art. As used herein, the term "alkenyl" encompasses both linear and branched alkenyl, unless otherwise specified.

For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenyl groups include, but are not limited to, ethenyl, propenyl, allyl, propenyl, butenyl, and 4-methylbutenyl.

The term "alkynyl" refers to a linear or branched monovalent hydrocarbon radical, which contains one or more carbon-carbon triple bonds. The alkynyl may be optionally substituted, e.g., as described herein. The term "alkynyl" also encompasses both linear and branched alkynyl, unless otherwise specified. In certain embodiments, the alkynyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkynyl groups include, but are not limited to, ethynyl (—C≡CH) and propargyl (—CH$_2$C≡CH). For example, $C_{2-6}$ alkynyl refers to a linear unsaturated monovalent hydrocarbon radical of 2 to 6 carbon atoms or a branched unsaturated monovalent hydrocarbon radical of 3 to 6 carbon atoms.

The term "cycloalkyl" refers to a cyclic saturated bridged or non-bridged monovalent hydrocarbon radical, which may be optionally substituted, e.g., as described herein. In certain embodiments, the cycloalkyl has from 3 to 20 ($C_{3-20}$), from 3 to 15 ($C_{3-15}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclohexyl, cycloheptyl, decalinyl, and adamantyl.

The term "aryl" refers to a monocyclic or multicyclic monovalent aromatic group. In certain embodiments, the aryl has from 6 to 20 ($C_{6-20}$), from 6 to 15 ($C_{6-15}$), or from 6 to 10 ($C_{6-10}$) ring atoms. Examples of aryl groups include, but are not limited to, phenyl, naphthyl, fluorenyl, azulenyl, anthryl, phenanthryl, pyrenyl, biphenyl, and terphenyl. Aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl). All such aryl groups may also be optionally substituted, e.g., as described herein.

The term "heteroaryl" refers to a monocyclic or multicyclic aromatic group, wherein at least one ring contains one or more heteroatoms independently selected from O, S, and N. Each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. Examples of monocyclic heteroaryl groups include, but are not limited to, pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, and triazinyl. Examples of bicyclic heteroaryl groups include, but are not limited to, indolyl, benzothiazolyl, benzoxazolyl, benzothienyl, quinolinyl, tetrahydroisoquinolinyl, isoquinolinyl, benzimidazolyl, benzopyranyl, indolizinyl, benzofuranyl, isobenzofuranyl, chromonyl, coumarinyl, cinnolinyl, quinoxalinyl, indazolyl, purinyl, pyrrolopyridinyl, furopyridinyl, thienopyridinyl, dihydroisoindolyl, and tetrahydroquinolinyl. Examples of tricyclic heteroaryl groups include, but are not limited to, carbazolyl, benzindolyl, phenanthrollinyl, acridinyl, phenanthridinyl, and xanthenyl. All such heteroaryl groups may also be optionally substituted, e.g., as described herein.

The term "heterocyclyl" or "heterocyclic" refers to a monocyclic or multicyclic non-aromatic ring system, wherein one or more of the ring atoms are heteroatoms independently selected from O, S, or N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. Examples of heterocyclyl groups include, but are not limited to, pyrrolidinyl, piperidinyl, 2-oxopyrrolidinyl, 2-oxopiperidinyl, morpholinyl, piperazinyl, tetrahydropyranyl, and thiomorpholinyl. All such heterocyclic groups may also be optionally substituted, e.g., as described herein.

The term "acyl" refers to a —C(O)R radical, wherein R is, for example, alkyl, alkenyl, alkynyl, cycloalkyl, aryl, heteroaryl, or heterocyclyl, each as defined herein. Examples of acyl groups include, but are not limited to, acetyl, propionyl, butanoyl, isobutanoyl, pentanoyl, hexanoyl, heptanoyl, octanoyl, nonanoyl, decanoyl, dodecanoyl, tetradecanoyl, hexadecanoyl, octadecanoyl, eicosanoyl, docosanoyl, myristoleoyl, palmitoleoyl, oleoyl, linoleoyl, arachidonoyl, benzoyl, pyridinylcarbonyl, and furoyl.

The term "halogen", "halide" or "halo" refers to fluorine, chlorine, bromine, or iodine.

The term "arylalkyl" refers to an aryl group appended to an alkyl radical, such as aryl-(CH$_2$)—, aryl-CH$_2$—CH$_2$—, and aryl-CH$_2$—CH$_2$—CH$_2$—.

The term "alkaryl" refers to an alkyl group appended to an aryl radical, such as CH3-aryl, CH$_3$—CH$_2$— aryl, and CH$_3$—CH$_2$—CH$_2$— aryl.

The term "optionally substituted" is intended to mean that a group, such as an alkyl, alkylene, alkenyl, alkenylene, alkynyl, alkynylene, alkoxyl, cycloalkyl, cycloalkylene, aryl, arylene, heteroaryl, or heterocyclyl group, may be substituted with one or more substituents independently selected from, e.g., halo, cyano (—CN), nitro (—NO$_2$), —SR$^a$, —S(O)R$^a$, —S(O)$_2$R$^a$, —R$^a$, —C(O)R$^a$, —C(O)OR$^a$, —C(O)NR$^b$R$^c$, —OCH$_2$C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$ NR$^b$R$^c$, —NR$^b$R$^c$, —NR$^a$C(O)R$^b$, —NR$^a$C(O)OR$^b$, —NR$^a$C(O)NR$^b$R$^c$, —NR$^a$C(=NR$^a$)NR$^b$R$^c$, —NR$^a$S(O)R$^b$, —NR$^a$S(O)$_2$R$^b$, —NR$^a$S(O)NR$^b$R$^c$, —NR$^a$S(O)$_2$R$^b$R$^c$, or —OSi—R$^a$R$^b$R$^c$; wherein R$^a$, R$^b$, R$^c$, and R$^d$ are each independently, e.g., hydrogen, alkyl, alkenyl, alkynyl, cycloalkyl, aryl, heteroaryl, or heterocyclyl, each optionally substituted, e.g., as described herein; or R$^b$ and R$^c$ together with the N atom to which they are attached form heterocyclyl or heteroaryl, each optionally substituted, e.g., as described herein. The group can be substituted with any described moiety, including, but not limited to, one or more moieties selected from the group consisting of halogen (fluoro, chloro, bromo, or iodo), hydroxyl, amino, alkylamino (e.g., monoalkylamino, dialkylamino, or trialkylamino), arylamino (e.g., monoarylamino, diarylamino, or triarylamino), alkoxy, aryloxy, nitro, cyano, sulfonic acid, sulfate, phosphonic acid, phosphate, or phosphonate, either unprotected or protected as necessary, as known to those skilled in the art, for example, as taught in Greene, et al., *Protective Groups in Organic Synthesis*, John Wiley and Sons, Second Edition, 1991. As used herein, all groups that can be substituted in one embodiment are "optionally substituted," unless otherwise specified.

In certain embodiments, "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, or no less than about 94% no less than about 95%, no less than about 96%, no less than about 97%, no less than about 98%, no less than about 99%, or no less than about 99.5%, no less than about 99.8%. In certain embodiments, the compound comprises about 95% or more of the desired enantiomer and about 5% or less of the less preferred enantiomer based on the total weight of the racemate in question.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

The term "solvate" refers to a compound provided herein or a salt thereof, which further includes a stoichiometric or non-stoichiometric amount of solvent bound by non-covalent intermolecular forces. Where the solvent is water, the solvate is a hydrate.

Compounds

Provided herein are compounds which are useful for the treatment of HCV infection, which, in one embodiment, can have activity as HCV polymerase inhibitors. Also provided herein are pharmaceutical compositions that comprise the compounds, methods of manufacture of the compounds, and methods of use of the compounds for the treatment of HCV infection in a host in need of treatment.

In one aspect, provided herein is a compound of Formula I:

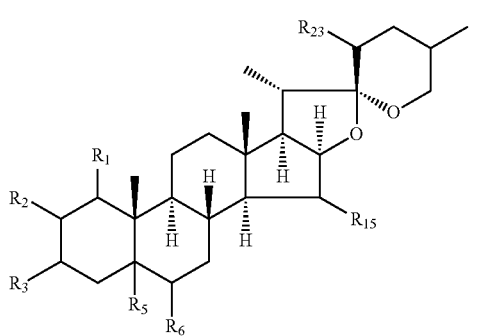

(I)

or a single enantiomer, a mixture of an enantiomeric pair, an individual diastereomer, or a mixture of diastereomers; or a pharmaceutically acceptable salt, solvate, or prodrug thereof, wherein:

each of $R_1$, $R_2$, $R_3$, $R_{15}$, and $R_{23}$ is independently H, OH, oxo, O-acyl, halo, O-alkyl, $OSO_3H$, $OSO_3Na$, $N_3$, $NH_2$, NHR, NRR', $NHSO_2R$, SR, SOR, $SO_2R$, $OPO_3H_2$, $OPO_3HNa$, $OPO_3Na_2$, O-monosacharride, O-disaccharide or O-oligosaccharide; and each of $R_5$ and $R_6$ is independently H, OH, O-acyl, halo, $OSO_3H$, O-alkyl, $OSO_3H$, $OSO_3Na$, $N_3$, $NH_2$, NHR, NRR', $NHSO_2R$, SR, SOR, $SO_2R$, $OPO_3H_2$, $OPO_3HNa$, $OPO_3Na_2$, epoxy, O-monosacharride, O-disaccharide or O-oligosaccharide, or $R_5$ and $R_6$ together form a double bond, where each of R and R' independently is alkyl (e.g., methyl), aryl, arylalkyl, alkaryl, heteroaryl, alkenyl, alkynyl, cycloalkyl, or heterocyclyl.

In some embodiments, the compound of Formula I has Formula I':

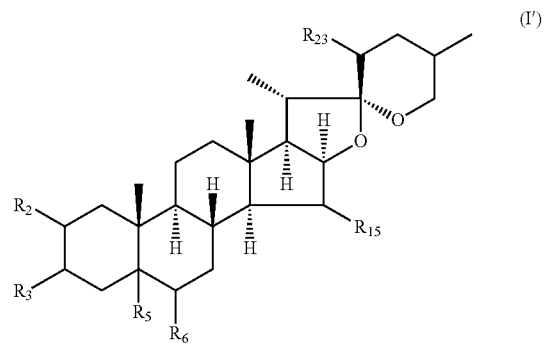

(I')

or a single enantiomer, a mixture of an enantiomeric pair, an individual diastereomer, or a mixture of diastereomers; or a pharmaceutically acceptable salt, solvate, or prodrug thereof, wherein:

$R_2$ is H or OH;

$R_3$ is OH, O-β-galactosyl, O-β-glucosyl(1→2)-β-Gal, O-β-mannosyl(1→2)-β-glucosyl, O-β-glucosyl(1→2)-O-[β-xylosyl(1→3)]-O-β-glucosyl(1→4)-β-galactosyl, O-β-glucosyl(1→2)-β-galactosyl, O-α-6-deoxy-mannosyl(1→2)-O-[α-6-deoxy-mannosyl(1→4)]-β-glucosyl, O-α-arabinosyl(1→4)-O-[α-6-deoxy-mannosyl(1→2)]-β-glucosyl or O-β-glucosyl(1→2)-O-[α-6-deoxy-mannosyl(1→2)]-O-β-glucosyl;

each of $R_5$ and $R_6$ is H, or $R_5$ and $R_6$ together form a double bond;

$R_{15}$ is H, OH or R; and $R_{23}$ is H, OH or SH, where each of R and R' independently is alkyl (e.g., methyl), aryl, arylalkyl, alkaryl, heteroaryl, alkenyl, alkynyl, cycloalkyl, or heterocyclyl.

In another aspect, provided herein is a compound of Formula II:

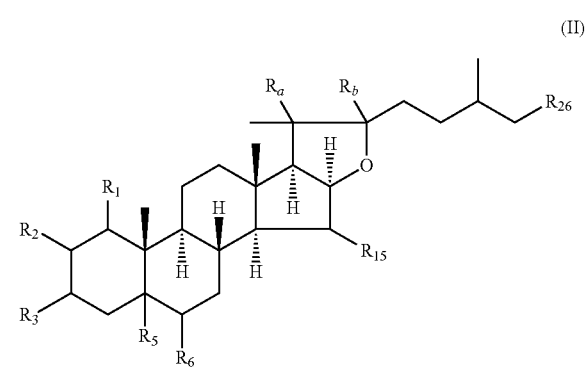

(II)

or a single enantiomer, a mixture of an enantiomeric pair, an individual diastereomer, or a mixture of diastereomers; or a pharmaceutically acceptable salt, solvate, or prodrug thereof, wherein:

each of $R_1$, $R_2$, $R_3$, and $R_{15}$ is independently H, OH, oxo, O-acyl, halo, O-alkyl, $OSO_3H$, $OSO_3Na$, $N_3$, $NH_2$, NHR, NRR', $NHSO_2R$, SR, SOR, $SO_2R$, $OPO_3H_2$, $OPO_3HNa$, $OPO_3Na_2$, O-monosacharride, O-disaccharide or O-oligosaccharide;

each of $R_5$ and $R_6$ is independently H, OH, O-acyl, halo, $OSO_3H$, O-alkyl, $OSO_3H$, $OSO_3Na$, $N_3$, $NH_2$, NHR, NRR', $NHSO_2R$, SR, SOR, $SO_2R$, $OPO_3H_2$, $OPO_3HNa$, $OPO_3Na_2$, epoxy, O-monosacharride, O-disaccharide or O-oligosaccharide, or $R_5$ and $R_6$ together form a double bond;

each of $R_a$ and $R_b$ is independently H, OH, O-acyl, halo, $OSO_3H$, O-alkyl, $OSO_3H$, $OSO_3Na$, $N_3$, $NH_2$, NHR, NRR', $NHSO_2R$, SR, SOR, $SO_2R$, $OPO_3H_2$, $OPO_3HNa$, $OPO_3Na_2$, epoxy, O-monosacharride, O-disaccharide or O-oligosaccharide, or $R_a$ and $R_b$ together form a double bond; and $R_{26}$ is OH, O-acyl, halo, O-alkyl, $OSO_3H$, $OSO_3Na$, $N_3$, $NH_2$, NHR, NRR', $NHSO_2R$, SR, SOR, $SO_2R$, $OPO_3H_2$, $OPO_3HNa$, $OPO_3Na_2$, CHO, carboxy, $CONH_2$, CONHR, CONRR', C(=O)O-akyl, O—C(=O)-alkyl, O-monosacharride, O-disaccharide or O-oligosaccharide, where each of R and R' independently is alkyl (e.g., methyl), aryl, arylalkyl, alkaryl, heteroaryl, alkenyl, alkynyl, cycloalkyl, or heterocyclyl.

In some embodiments, the compound of Formula II has Formula II':

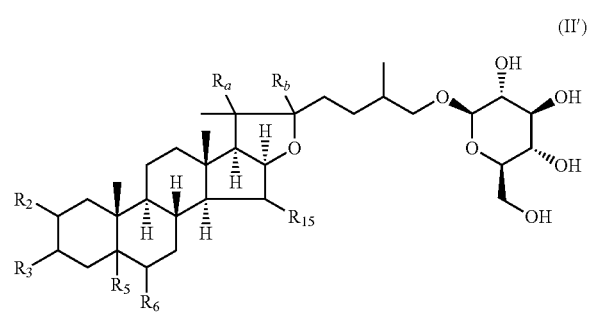

(II')

or a single enantiomer, a mixture of an enantiomeric pair, an individual diastereomer, or a mixture of diastereomers; or a pharmaceutically acceptable salt, solvate, or prodrug thereof, wherein:

$R_2$ is H or OH;

$R_3$ is O-β-glucosyl(1→2)-β-galactosyl, galactosyl, H, O-β-glucosyl(1→2)-O-[β-glucosyl(1→3)]-O-β-glucosyl(1→4)-β-galactosyl, O-β-glucosyl(1→2)-β-glucosyl or O-β-glucosyl(1→2)-O-[β-xylosyl(1→3)]-O-β-glucosyl(1→4)-β-galactosyl;

$R_5$ is H; $R_6$ is H or OH, or $R_5$ and $R_6$ together form a double bond;

$R_{15}$ is H or OH;

$R_a$ is H; and $R_b$ is OR or OH, or $R_a$ and $R_b$ together form a double bond, where each of R and R' independently is alkyl (e.g., methyl), aryl, arylalkyl, alkaryl, heteroaryl, alkenyl, alkynyl, cycloalkyl, or heterocyclyl.

In one aspect, provided herein is a compound of Formula III:

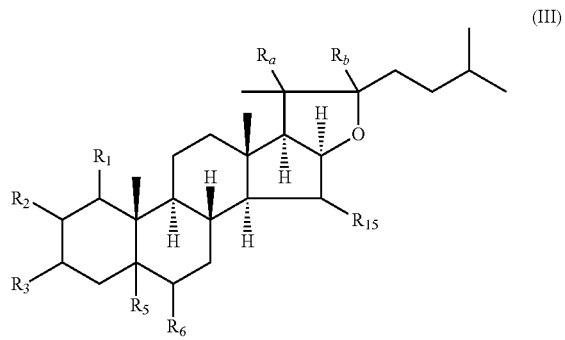

(III)

or a single enantiomer, a mixture of an enantiomeric pair, an individual diastereomer, or a mixture of diastereomers; or a pharmaceutically acceptable salt, solvate, or prodrug thereof, wherein:

each of $R_1$, $R_2$, $R_3$, $R_{15}$, and $R_b$ is independently H, OH, oxo, O-acyl, halo, O-alkyl, $OSO_3H$, $OSO_3Na$, $N_3$, $NH_2$, NHR, NRR', $NHSO_2R$, SR, SOR, $SO_2R$, $OPO_3H_2$, $OPO_3HNa$, $OPO_3Na_2$, O-monosacharride, O-disaccharide or O-oligosaccharide;

each of $R_5$ and $R_6$ is independently H, OH, O-acyl, halo, $OSO_3H$, O-alkyl, $OSO_3H$, $OSO_3Na$, $N_3$, $NH_2$, NHR, NRR', $NHSO_2R$, SR, SOR, $SO_2R$, $OPO_3H_2$, $OPO_3HNa$, $OPO_3Na_2$, epoxy, O-monosacharride, O-disaccharide or O-oligosaccharide, or $R_5$ and $R_6$ together form a double bond;

$R_a$ is alkyl (e.g., methyl); and $R_b$ is H, OH, O-acyl, halo, $OSO_3H$, O-alkyl, $OSO_3H$, $OSO_3Na$, $N_3$, $NH_2$, NHR, NRR', $NHSO_2R$, SR, SOR, $SO_2R$, $OPO_3H_2$, $OPO_3HNa$, $OPO_3Na_2$, epoxy, O-monosacharride, O-disaccharide or O-oligosaccharide, or $R_a$ and $R_b$ together form a double bond;

where each of R and R' independently is alkyl (e.g., methyl), aryl, arylalkyl, alkaryl, heteroaryl, alkenyl, alkynyl, cycloalkyl, or heterocyclyl.

In some embodiments, the compound of Formula III has Formula III':

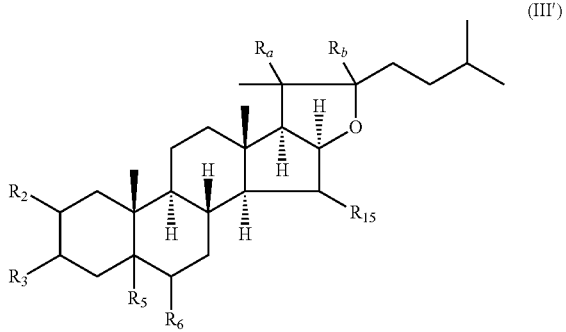

(III')

or a single enantiomer, a mixture of an enantiomeric pair, an individual diastereomer, or a mixture of diastereomers; or a pharmaceutically acceptable salt, solvate, or prodrug thereof, wherein:

$R_2$ is H;

$R_3$ is O-β-glucosyl(1→2)-β-galactosyl;

each of $R_5$ and $R_6$ is H;

$R_{15}$ is OH;

$R_a$ is R; and $R_b$ is OH or OR, where each of R and R' independently is alkyl (e.g., methyl), aryl, arylalkyl, alkaryl, heteroaryl, alkenyl, alkynyl, cycloalkyl, or heterocyclyl.

In certain embodiments according to Formula I, II, III, I', II', or III', each of alkyl, aryl, arylalkyl, alkaryl, heteroaryl, alkenyl, alkynyl, cycloalkyl, heterocyclyl, acyl, epoxy, monosacharride, disaccharide, and oligosaccharide is independently unsubstituted. In some embodiments according to Formula I, II, III, I', II', or III', each of alkyl, aryl, arylalkyl, alkaryl, heteroaryl, alkenyl, alkynyl, cycloalkyl, heterocyclyl, acyl, epoxy, monosacharride, disaccharide, and oligosaccharide is substituted.

The compounds provided herein are intended to encompass all possible stereoisomers, unless a particular stereochemistry is specified. Where the compound provided herein contains an alkenyl or alkenylene group, the compound may exist as one or mixture of geometric cis/trans (or Z/E) isomers. Where structural isomers are interconvertible via a low energy barrier, the compound may exist as a single tautomer or a mixture of tautomers. This can take the form of proton tautomerism in the compound that contains, for example, an imino, keto, or oxime group; or so-called valence tautomerism in the compound that contain an aromatic moiety. It follows that a single compound may exhibit more than one type of isomerism.

The compounds provided herein may be enantiomerically pure, such as a single enantiomer or a single diastereomer, or be stereoisomeric mixtures, such as a mixture of an enantiomeric pair, a racemic mixture, or a diastereomeric mixture. As such, one of skill in the art will recognize that administration of a compound in its (R) form is equivalent, for compounds that undergo epimerization in vivo, to administration of the compound in its (S) form. Conventional techniques for the preparation/isolation of individual enantiomers include synthesis from a suitable optically pure precursor, asymmetric synthesis from achiral starting materials, or resolution of an enantiomeric mixture, for example, chiral chromatography, recrystallization, resolution, diastereomeric salt formation, or derivatization into diastereomeric adducts followed by separation.

When the compound provided herein contains an acidic or basic moiety, it may also be provided as a pharmaceutically acceptable salt (See, Berge et al., *J. Pharm. Sci.* 1977, 66, 1-19; and "Handbook of Pharmaceutical Salts, Properties, and Use," Stahl and Wermuth, Ed.; Wiley-VCH and VHCA, Zurich, 2002).

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

The compound provided herein may also be provided as a prodrug, which is a functional derivative of the compound, for example, of Formula I, II, III, I', II' or III' and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, *Progress in Drug Research* 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnejad in "Transport Processes in Pharmaceutical Systems," Amidon et al., Ed., Marcell Dekker, 185-218, 2000; Balant et al., *Eur. J. Drug Metab. Pharmacokinet.* 1990, 15, 143-53; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs,* 1977, 409-421; Nathwani and Wood, *Drugs* 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; and Waller et al., *Br. J. Clin. Pharmac.* 1989, 28, 497-507.

Methods of Synthesis

Figure 3:
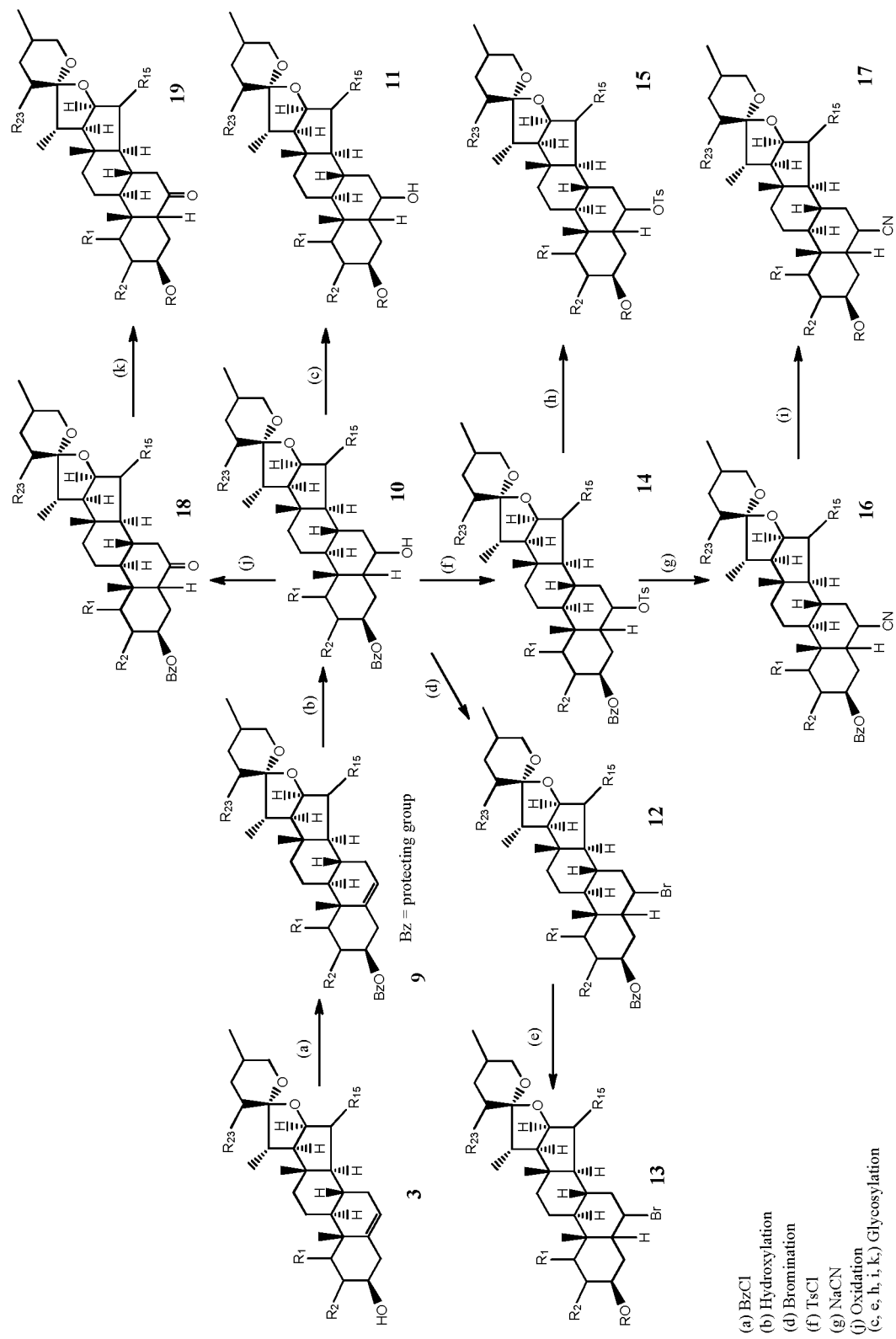
FIG. 3 depicts a general synthetic scheme for synthesizing compounds 11, 13, 15, 17, 19 of Formula I.
Figure 4:
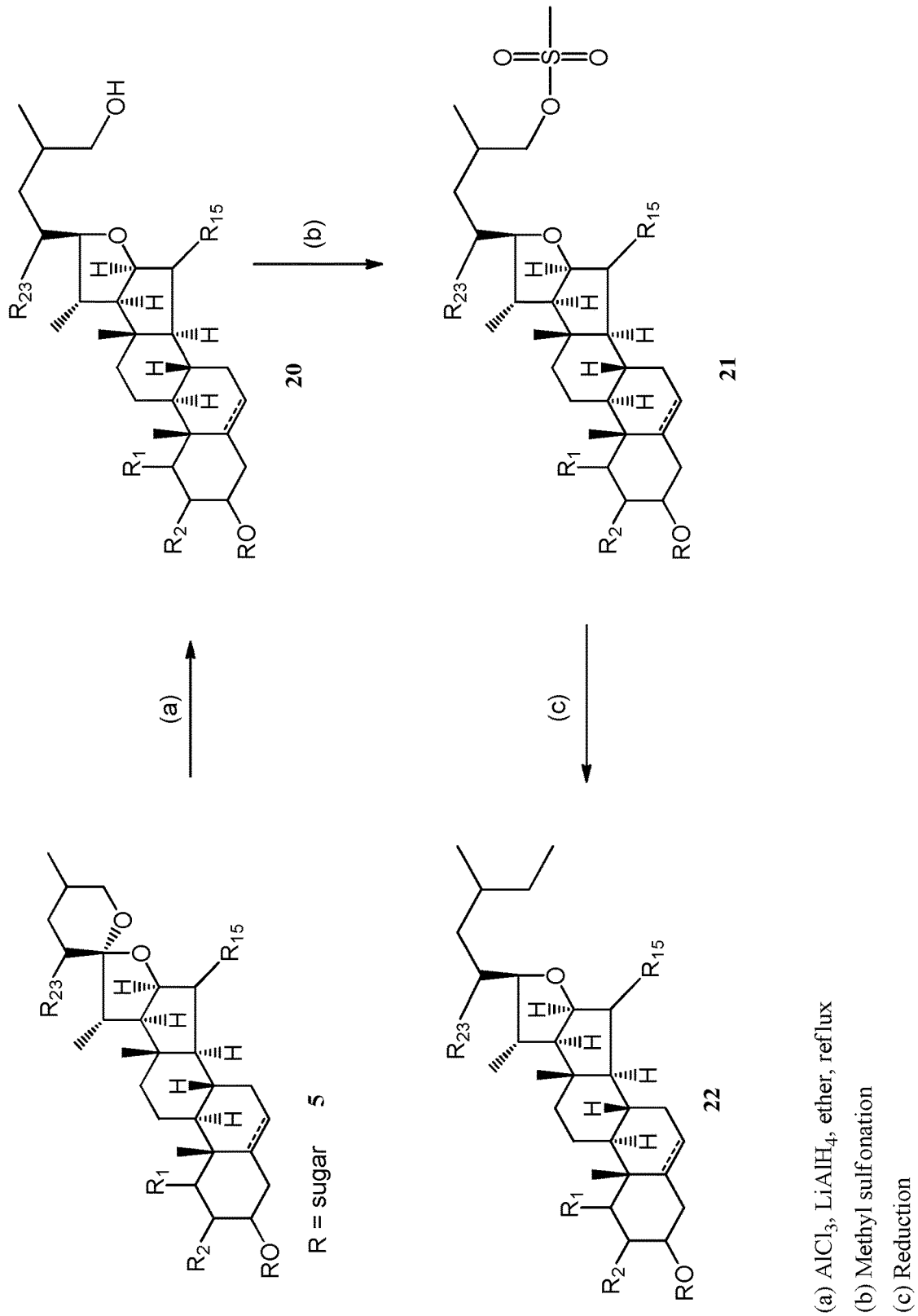
FIG. 4 depicts a general synthetic scheme for synthesizing compounds 20-22 of Formula II.

The compound provided herein can be prepared, isolated, or obtained by any method known to one of skill in the art. For example, a compound of Formula I or I' can be prepared as shown in the synthetic scheme as shown in FIG. 1 and the examples disclosed herein; a compound of Formula II or II' can be prepared as shown in the synthetic scheme as shown in FIG. 3 and the examples disclosed herein; and a compound of Formula III or III' can be prepared as shown in the synthetic scheme as shown in FIG. 4 and the examples disclosed herein.

Pharmaceutical Compositions

Provided herein are pharmaceutical compositions comprising a compound provided herein as an active ingredient, including a single enantiomer, a mixture of an enantiomeric pair, an individual diastereomer, or a mixture of diastereomers thereof; or a pharmaceutically acceptable salt, solvate, or prodrug thereof, in a pharmaceutically acceptable vehicle, carrier, diluent, or excipient, or a mixture thereof; in combination with one or more pharmaceutically acceptable excipients or carriers. In certain embodiments, the pharmaceutical composition comprises at least one release controlling excipient or carrier. In certain embodiments, the pharmaceutical composition comprises at least one nonrelease controlling excipient or carrier. In certain embodiments, the pharmaceutical composition comprises at least one release controlling and at least one nonrelease controlling excipients or carriers.

The compound provided herein may be administered alone, or in combination with one or more other compounds provided herein, one or more other active ingredients. The pharmaceutical compositions that comprise a compound provided herein may be formulated in various dosage forms for oral, parenteral, and topical administration. The pharmaceutical compositions may also be formulated as a modified release dosage form, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art (see, Remington: The Science and Practice of Pharmacy, supra; Modified-Release Drug Deliver Technology, Rathbone et al., Eds., Drugs and the Pharmaceutical Science, Marcel Dekker, Inc.: New York, N.Y., 2003; Vol. 126).

In one embodiment, the pharmaceutical compositions are provided in a dosage form for oral administration, which comprise a compound provided herein, including a single enantiomer, a mixture of an enantiomeric pair, an individual diastereomer, or a mixture of diastereomers thereof; or a pharmaceutically acceptable salt, solvate, or prodrug thereof; and one or more pharmaceutically acceptable excipients or carriers.

In another embodiment, the pharmaceutical compositions are provided in a dosage form for parenteral administration, which comprise a compound provided herein, including a single enantiomer, a mixture of an enantiomeric pair, an individual diastereomer, or a mixture of diastereomers thereof; or a pharmaceutically acceptable salt, solvate, or prodrug thereof; and one or more pharmaceutically acceptable excipients or carriers.

In yet another embodiment, the pharmaceutical compositions are provided in a dosage form for topical administration, which comprise a compound provided herein, including a single enantiomer, a mixture of an enantiomeric pair, an individual diastereomer, or a mixture of diastereomers thereof; or a pharmaceutically acceptable salt, solvate, or prodrug thereof; and one or more pharmaceutically acceptable excipients or carriers.

The pharmaceutical compositions provided herein may be provided in unit-dosage forms or multiple-dosage forms. Unit-dosage forms, as used herein, refer to physically discrete units suitable for administration to human and animal subjects and packaged individually as is known in the art. Each unit-dose contains a predetermined quantity of the active ingredient(s) sufficient to produce the desired therapeutic effect, in association with the required pharmaceutical carriers or excipients. Examples of unit-dosage forms include ampoules, syringes, and individually packaged tablets and capsules. Unit-dosage forms may be administered in fractions or multiples thereof. A multiple-dosage form is a plurality of identical unit-dosage forms packaged in a single container to be administered in segregated unit-dosage form. Examples of multiple-dosage forms include vials, bottles of tablets or capsules, or bottles of pints or gallons.

The pharmaceutical compositions provided herein may be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

A. Oral Administration

The pharmaceutical compositions provided herein may be provided in solid, semisolid, or liquid dosage forms for oral administration. As used herein, oral administration also include buccal, lingual, and sublingual administration. Suitable oral dosage forms include, but are not limited to, tablets, capsules, pills, troches, lozenges, pastilles, cachets, pellets, medicated chewing gum, granules, bulk powders, effervescent or non-effervescent powders or granules, solutions, emulsions, suspensions, solutions, wafers, sprinkles, elixirs, and syrups. In addition to the active ingredient(s), the pharmaceutical compositions may contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include colloidal silicon dioxide, CAB-O-SIL (Cabot Co. of Boston, Mass.), and asbestos-free talc. Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Flavoring agents include natural flavors extracted from plants, such as fruits, and synthetic blends of compounds which produce a pleasant taste sensation, such as peppermint and methyl salicylate. Sweetening agents include sucrose, lactose, mannitol, syrups, glycerin, and artificial sweeteners, such as saccharin and aspartame. Suitable emulsifying agents include gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suspending and dispersing agents include sodium carboxymethylcellulose, pectin, tragacanth, Veegum, acacia, sodium carbomethylcellulose, hydroxypropyl methylcellulose, and polyvinylpyrrolidone. Preservatives include glycerin, methyl and propylparaben, benzoic add, sodium benzoate and alcohol. Wetting agents include propylene glycol monostearate, sorbitan monooleate, diethylene glycol monolaurate, and polyoxyethylene lauryl ether. Solvents include glycerin, sorbitol, ethyl alcohol, and syrup. Examples of non-aqueous liquids utilized in emulsions include mineral oil and cottonseed oil. Organic acids include citric and tartaric acid. Sources of carbon dioxide include sodium bicarbonate and sodium carbonate.

It should be understood that many carriers and excipients may serve several functions, even within the same formulation.

The pharmaceutical compositions provided herein may be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquids or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration may be also provided in the forms of liposomes, micelles, microspheres, or nanosystems. Micellar dosage forms can be prepared as described in U.S. Pat. No. 6,350,458.

The pharmaceutical compositions provided herein may be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein may be formulated as immediate or modified release dosage forms, including delayed-, sustained, pulsed-, controlled, targeted-, and programmed-release forms.

The pharmaceutical compositions provided herein may be co-formulated with other active ingredients which do not impair the desired therapeutic action, or with substances that supplement the desired action, such as drotrecogin-α, and hydrocortisone.

B. Parenteral Administration

The pharmaceutical compositions provided herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

The pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

The pharmaceutical compositions provided herein may be formulated for single or multiple dosage administration. The single dosage formulations are packaged in an ampoule, a vial, or a syringe. The multiple dosage parenteral formulations must contain an antimicrobial agent at bacteriostatic or fungistatic concentrations. All parenteral formulations must be sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein may be formulated as immediate or modified release dosage forms, including delayed-, sustained, pulsed-, controlled, targeted-, and programmed-release forms.

The pharmaceutical compositions may be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical compositions provided herein may be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical compositions provided herein may be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, dermal patches. The topical formulation of the pharmaceutical compositions provided herein may also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions may also be administered topically by electroporation, iontophoresis, phonophoresis, sonophoresis, or microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions provided herein may be provided in the forms of ointments, creams, and gels. Suitable ointment vehicles include oleaginous or hydrocarbon vehicles, including such as lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, *Remington: The Science and Practice of Pharmacy*, supra). These vehicles are emollient but generally require addition of antioxidants and preservatives.

Suitable cream base can be oil-in-water or water-in-oil. Cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include crosslinked acrylic acid polymers, such as carbomers, carboxypolyalkylenes, CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein may be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, hydrogels, such as polyvinyl alcohol, hydroxyethyl methacrylate, polyacrylic acid; glycerinated gelatin. Combinations of the various vehicles may be used. Rectal and vaginal suppositories may be prepared by the compressed method or molding. The typical weight of a rectal and vaginal suppository is about 2 to about 3 g.

The pharmaceutical compositions provided herein may be administered ophthalmically in the forms of solutions, suspensions, ointments, emulsions, gel-forming solutions, powders for solutions, gels, ocular inserts, and implants.

The pharmaceutical compositions provided herein may be administered intranasally or by inhalation to the respiratory tract. The pharmaceutical compositions may be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions may also be provided as a dry powder for insufflation, alone or in combination with an inert carrier such as lactose or phospholipids; and nasal drops. For intranasal use, the powder may comprise a bioadhesive agent, including chitosan or cyclodextrin.

Solutions or suspensions for use in a pressurized container, pump, spray, atomizer, or nebulizer may be formulated to contain ethanol, aqueous ethanol, or a suitable alternative agent for dispersing, solubilizing, or extending release of the active ingredient provided herein, a propellant as solvent; and/or a surfactant, such as sorbitan trioleate, oleic acid, or an oligolactic acid.

The pharmaceutical compositions provided herein may be micronized to a size suitable for delivery by inhalation, such as about 50 micrometers or less, or about 10 micrometers or less. Particles of such sizes may be prepared using a comminuting method known to those skilled in the art, such as spiral jet milling, fluid bed jet milling, supercritical fluid processing to form nanoparticles, high pressure homogenization, or spray drying.

Capsules, blisters and cartridges for use in an inhaler or insufflator may be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients or carriers include dextran, glucose, maltose, sorbitol, xylitol, fructose, sucrose, and trehalose. The pharmaceutical compositions provided herein for inhaled/intranasal administration may further comprise a suitable flavor, such as menthol and levomenthol, or sweeteners, such as saccharin or saccharin sodium.

The pharmaceutical compositions provided herein for topical administration may be formulated to be immediate release or modified release, including delayed-, sustained-, pulsed-, controlled-, targeted, and programmed release.

D. Modified Release

The pharmaceutical compositions provided herein may be formulated as a modified release dosage form. As used herein, the term "modified release" refers to a dosage form in which the rate or place of release of the active ingredient(s) is different from that of an immediate dosage form when administered by the same route. Modified release dosage forms include delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

1. Matrix Controlled Release Devices

The pharmaceutical compositions provided herein in a modified release dosage form may be fabricated using a matrix controlled release device known to those skilled in the art (see, Takada et al in "Encyclopedia of Controlled Drug Delivery," Vol. 2, Mathiowitz Ed., Wiley, 1999).

In one embodiment, the pharmaceutical compositions provided herein in a modified release dosage form is formulated using an erodible matrix device, which is water-swellable, erodible, or soluble polymers, including synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; and cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(–)-3-hydroxybutyric acid; and other acrylic acid derivatives, such as homopolymers and copolymers of butylmethacrylate, methylmethacrylate, ethylmethacrylate, ethylacrylate, (2-dimethylaminoethyl)methacrylate, and (trimethylaminoethyl)methacrylate chloride.

In further embodiments, the pharmaceutical compositions are formulated with a non-erodible matrix device. The active ingredient(s) is dissolved or dispersed in an inert matrix and is released primarily by diffusion through the inert matrix once administered. Materials suitable for use as a non-erodible matrix device included, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, polyvinyl chloride, plasticized nylon, plasticized polyethylene terephthalate, natural rubber, silicone rubbers, polydimethylsiloxanes, silicone carbonate copolymers, and; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical compositions provided herein in a modified release dosage form may be prepared by methods known to those skilled in the art, including direct compression, dry or wet granulation followed by compression, melt-granulation followed by compression.

2. Osmotic Controlled Release Devices

The pharmaceutical compositions provided herein in a modified release dosage form may be fabricated using an osmotic controlled release device, including one-chamber system, two-chamber system, asymmetric membrane technology (AMT), and extruding core system (ECS). In general, such devices have at least two components: (a) the core which contains the active ingredient(s); and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents water-swellable hydrophilic polymers, which are also referred to as "osmopolymers" and "hydrogels," including, but not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol, organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates may be employed to influence how rapidly the active ingredient(s) is initially delivered from the dosage form. For example, amorphous sugars, such as MANNOGEM™ EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core may also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane may also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane may be formed post-coating by mechanical or laser drilling. Delivery port(s) may also be formed in situ by erosion of a plug of water-soluble material or by rupture of a thinner portion of the membrane over an indentation in the core. In addition, delivery ports may be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form may further comprise additional conventional excipients or carriers as described herein to promote performance or processing of the formulation.

The osmotic controlled-release dosage forms can be prepared according to conventional methods and techniques known to those skilled in the art (see, *Remington: The Science and Practice of Pharmacy*, supra; Santus and Baker, *J. Controlled Release* 1995, 35, 1-21; Verma et al., *Drug Development and Industrial Pharmacy* 2000, 26, 695-708; Verma et al., *J. Controlled Release* 2002, 79, 7-27).

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients or carriers. See, U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), a hydroxyethyl cellulose, and other pharmaceutically acceptable excipients or carriers.

3. Multiparticulate Controlled Release Devices

The pharmaceutical compositions provided herein in a modified release dosage form may be fabricated a multiparticulate controlled release device, which comprises a multiplicity of particles, granules, or pellets, ranging from about 10 μm to about 3 mm, about 50 μm to about 2.5 mm, or from about 100 μm to about 1 mm in diameter. Such multiparticulates may be made by the processes know to those skilled in the art, including wet-and dry-granulation, extrusion/spheronization, roller-compaction, melt-congealing, and by spray-coating seed cores. See, for example, *Multiparticulate Oral Drug Delivery*; Marcel Dekker: 1994; and *Pharmaceutical Pelletization Technology*; Marcel Dekker: 1989.

Other excipients or carriers as described herein may be blended with the pharmaceutical compositions to aid in processing and forming the multiparticulates. The resulting particles may themselves constitute the multiparticulate device or may be coated by various film-forming materials, such as enteric polymers, water-swellable, and water-soluble polymers. The multiparticulates can be further processed as a capsule or a tablet.

4. Targeted Delivery

The pharmaceutical compositions provided herein may also be formulated to be targeted to a particular tissue, receptor, or other area of the body of the subject to be treated, including liposome-, resealed erythrocyte-, and antibody-based delivery systems.

Methods of Use

Provided herein are methods for treating or preventing a disease associated with beta-amyloid in a host or subject, which comprises administering to the host or subject a therapeutically effective amount of the compound of Formula I, II, III, I', II' or III', including a single enantiomer, a mixture of an enantiomeric pair, an individual diastereomer, or a mixture of diastereomers thereof; or a pharmaceutically acceptable salt, solvate, or prodrug thereof. In one embodiment, the host or subject is a mammal. In another embodiment, the host or subject is a human.

Additionally, provided herein is a method for reducing beta-amyloid peptide production in a host to mitigate a disease associated with beta-amyloid, which comprises contacting the host or subject with a therapeutically effective amount of the compound of Formula I, II, III, I', II' or III', including a single enantiomer, a mixture of an enantiomeric pair, an individual diastereomer, or a mixture of diastereomers thereof; or a pharmaceutically acceptable salt, solvate, or prodrug thereof. In one embodiment, the host is a cell. In another embodiment, the host is a human cell. In yet another embodiment, the host is a mammal. In still another embodiment, the host is human.

In certain embodiments, administration of a therapeutically effective amount of the compound of Formula I, II, III, I', II' or III', including a single enantiomer, a mixture of an enantiomeric pair, an individual diastereomer, or a mixture of diastereomers thereof; or a pharmaceutically acceptable salt, solvate, or prodrug thereof, results in a 10%, 20%, 30%, 40%, 50%, 60%, 70%, 80%, 90%, 95%, 99% or more reduction in the beta-amyloid peptide production in a subject relative to another subject without administration of the compound, as determined at 1 day, 2 days, 3 days, 4 days, 5 days, 10 days, 15 days, or 30 days after the administration by a method known in the art, e.g., determination of viral titer.

Also provided herein is a method for treating, preventing, or ameliorating one or more symptoms of a disease associated with beta-amyloid, comprising administering to a subject a therapeutically effective amount of the compound of Formula I, II, III, I', II' or III', including a single enantiomer, a mixture of an enantiomeric pair, an individual diastereomer, or a mixture of diastereomers thereof; or a pharmaceutically acceptable salt, solvate, or prodrug thereof. Some non-limiting examples of the compound of Formula I, II, III, I', II' or III' include neurodegenerative diseases, mild cognitive impairment, cerebral amyloid angiopathy of sporadic or hereditary form, inclusion body myositis, Down syndrome, dementia with Lewy bodies, senile dementia, or Alzheimer's disease. In some embodiments, the disease associated with beta-amyloid is not dementia or Alzheimer's disease. In some embodiments, the disease associated with beta-amyloid is not dementia with Lewy bodies, senile dementia or Alzheimer's disease.

Depending on the condition, disorder, or disease, to be treated and the subject's condition, a compound provided herein may be administered by oral, parenteral (e.g., intramuscular, intraperitoneal, intravenous, ICV, intracistemal injection or infusion, subcutaneous injection, or implant), inhalation, nasal, vaginal, rectal, sublingual, or topical (e.g., transdermal or local) routes of administration, and may be formulated, alone or together, in suitable dosage unit with pharmaceutically acceptable carriers, adjuvants and vehicles appropriate for each route of administration.

The dose may be in the form of one, two, three, four, five, six, or more sub-doses that are administered at appropriate intervals per day. The dose or sub-doses can be administered in the form of dosage units containing from about 0.1 to about 1000 milligram, from about 0.1 to about 500 milligrams, or from 0.5 about to about 100 milligram active ingredient(s) per dosage unit, and if the condition of the patient requires, the dose can, by way of alternative, be administered as a continuous infusion.

In certain embodiments, an appropriate dosage level is about 0.01 to about 100 mg per kg patient body weight per day (mg/kg per day), about 0.01 to about 50 mg/kg per day, about 0.01 to about 25 mg/kg per day, or about 0.05 to about 10 mg/kg per day, which may be administered in single or multiple doses. A suitable dosage level may be about 0.01 to about 100 mg/kg per day, about 0.05 to about 50 mg/kg per day, or about 0.1 to about 10 mg/kg per day. Within this range the dosage may be about 0.01 to about 0.1, about 0.1 to about 1.0, about 1.0 to about 10, or about 10 to about 50 mg/kg per day.

Combination Therapy

The compounds provided herein may also be combined or used in combination with other therapeutic agents useful in the treatment and/or prevention of diseases associated with beta-amyloid such as neurodegenerative diseases, mild cognitive impairment, cerebral amyloid angiopathy of sporadic or hereditary form, inclusion body myositis, Down syndrome, dementia with Lewy bodies, senile dementia, or Alzheimer's disease. In some embodiments, the disease associated with beta-amyloid is not dementia or Alzheimer's disease.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a subject with a disease or disorder. A first therapy (e.g., a prophylactic or therapeutic agent such as a compound provided herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to the subject. Triple therapy is also contemplated herein.

As used herein, the term "synergistic" includes a combination of a compound provided herein and another therapy (e.g., a prophylactic or therapeutic agent) which has been or is currently being used to treat, prevent, or manage a disease or disorder, which is more effective than the additive effects of the therapies. A synergistic effect of a combination of therapies (e.g., a combination of prophylactic or therapeutic agents) permits the use of lower dosages of one or more of the therapies and/or less frequent administration of said therapies to a subject with a disorder. The ability to utilize lower dosages of a therapy (e.g., a prophylactic or therapeutic agent) and/or to administer said therapy less frequently reduces the toxicity associated with the administration of said therapy to a subject without reducing the efficacy of said therapy in the prevention or treatment of a disorder). In addition, a synergistic effect can result in improved efficacy of agents in the prevention or treatment of a disorder. Finally, a synergistic effect of a combination of therapies (e.g., a combination of prophylactic or therapeutic agents) may avoid or reduce adverse or unwanted side effects associated with the use of either therapy alone.

The compound provided herein can be administered in combination or alternation with another therapeutic agent that can be used to treat and/or prevent diseases associated with beta-amyloid. In some embodiments, the therapeutic agent is an acetyl cholinesterase inhibitor, an N-methyl-D-aspartate receptor antagonist, Donepezil (Aricept™), ENA-713 (Exelon™), Galantamine (Reminyl™), Memantine (Namenda™), Tacrine (Cognex™), Risperidone (Risperidol™), a serotonin reuptake inhibitor (SRIs), benzodiazepines, Ginkgo biloba extract, alpha-tocopherol (vitamin E), melatonin, docosahexanoic acid (DHA)/omega-3 fatty acid, any agent that can lower the production of β-amyloid peptides (Aβ) or a combination thereof. Aβ are generated from proteolysis of amyloid precursor protein (APP) during aging. High levels of Aβ and its oligomers can be toxic to neuronal cells. APP is a transmembrane protein whose proteolysis can be mediated by α-, β- and γ-secretases which can cleave at specific sites of the polypeptide. The specific process of Aβ production, or amyloidogenesis, generally involves first cleavage of APP to create an Aβ containing c-terminal fragment (CTF) known as β-CTF which is then cleaved by multiprotein γ-secretase complex to produce Aβ and γ-CTF. APP is generally located in both plasma membrane and intracellular compartments including endosome, golgi bodies and secretary vesicles.

In combination therapy, effective dosages of two or more agents are administered together, whereas in alternation or sequential-step therapy, an effective dosage of each agent is administered serially or sequentially. The dosages given will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

In certain embodiments, the compounds provided herein can be combined with one or more steroidal drugs known in the art, including, but not limited to the group including, aldosterone, beclometasone, betamethasone, deoxycorticosterone acetate, fludrocortisone, hydrocortisone (cortisol), prednisolone, prednisone, methylprednisolone, dexamethasone, and triamcinolone.

In certain embodiments, the compounds provided herein can be combined with one or more antibacterial agents known in the art, including, but not limited to the group including amikacin, amoxicillin, ampicillin, arsphenamine, azithromycin, aztreonam, azlocillin, bacitracin, carbenicillin, cefaclor, cefadroxil, cefamandole, cefazolin, cephalexin, cefdinir, cefditorin, cefepime, cefixime, cefoperazone, cefotaxime, cefoxitin, cefpodoxime, cefprozil, ceftazidime, ceftibuten, ceftizoxime, ceftriaxone, cefuroxime, chloramphenicol, cilastin, ciprofloxacin, clarithromycin, clindamycin, cloxacillin, colistin, dalfopristin, demeclocycline, dicloxacillin, dirithromycin, doxycycline, erythromycin, enrofloxacin, ertepenem, ethambutol, flucloxacillin, fosfomycin, furazolidone, gatifloxacin, geldanamycin, gentamicin, herbimycin, imipenem, isoniazid, kanamycin, levofloxacin, linezolid, lomefloxacin, loracarbef, mafenide, moxifloxacin, meropenem, metronidazole, mezlocillin, minocycline, mupirocin, nafcillin, neomycin, netilmicin, nitrofurantoin, norfloxacin, ofloxacin, oxytetracycline, penicillin, piperacillin, platensimycin, polymyxin B, prontocil, pyrazinamide, quinupristine, rifampin, roxithromycin, spectinomycin, streptomycin, sulfacetamide, sulfamethizole, sulfamethoxazole, teicoplanin, telithromycin, tetracycline, ticarcillin, tobramycin, trimethoprim, troleandomycin, trovafloxacin, and vancomycin.

In certain embodiments, the compounds provided herein can be combined with one or more antifungal agents known in the art, including, but not limited to the group including amorolfine, amphotericin B, anidulafungin, bifonazole, butenafine, butoconazole, caspofungin, ciclopirox, clotrimazole, econazole, fenticonazole, filipin, fluconazole, isoconazole, itraconazole, ketoconazole, micafungin, miconazole, naftifine, natamycin, nystatin, oxyconazole, ravuconazole, posaconazole, rimocidin, sertaconazole, sulconazole, terbinafine, terconazole, tioconazole, and voriconazole.

In certain embodiments, the compounds provided herein can be combined with one or more anticoagulants known in the art, including, but not limited to the group including acenocoumarol, argatroban, bivalirudin, lepirudin, fondaparinux, heparin, phenindione, warfarin, and ximelagatran.

In certain embodiments, the compounds provided herein can be combined with one or more thrombolytics known in the art, including, but not limited to the group including anistreplase, reteplase, t-PA (alteplase activase), streptokinase, tenecteplase, and urokinase.

In certain embodiments, the compounds provided herein can be combined with one or more non-steroidal anti-inflammatory agents known in the art, including, but not limited to, aceclofenac, acemetacin, amoxiprin, aspirin, azapropazone, benorilate, bromfenac, carprofen, celecoxib, choline magnesium salicylate, diclofenac, diflunisal, etodolac, etoricoxib, faislamine, fenbufen, fenoprofen, flurbiprofen, ibuprofen, indometacin, ketoprofen, ketorolac, lornoxicam, loxoprofen, lumiracoxib, meclofenamic acid, mefenamic acid, meloxicam, metamizole, methyl salicylate, magnesium salicylate, nabumetone, naproxen, nimesulide, oxyphenbutazone, parecoxib, phenylbutazone, piroxicam, salicyl salicylate, sulindac, sulfinpyrazone, suprofen, tenoxicam, tiaprofenic acid, and tolmetin.

In certain embodiments, the compounds provided herein can be combined with one or more antiplatelet agents known in the art, including, but not limited to, abciximab, cilostazol, clopidogrel, dipyridamole, ticlopidine, and tirofibin.

The compounds provided herein can also be administered in combination with other classes of compounds, including, but not limited to, endothelin converting enzyme (ECE) inhibitors, such as phosphoramidon; thromboxane receptor antagonists, such as ifetroban; potassium channel openers; thrombin inhibitors, such as hirudin; growth factor inhibitors, such as modulators of PDGF activity; platelet activating factor (PAF) antagonists; anti-platelet agents, such as GPIIb/IIIa blockers (e.g., abciximab, eptifibatide, and tirofiban), P2Y(AC) antagonists (e.g., clopidogrel, ticlopidine and CS-747), and aspirin; anticoagulants, such as warfarin; low molecular weight heparins, such as enoxaparin; Factor VIIa Inhibitors and Factor Xa Inhibitors; renin inhibitors; neutral endopeptidase (NEP) inhibitors; vasopeptidase inhibitors (dual NEP-ACE inhibitors), such as omapatrilat and gemopatrilat; HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, atavastatin, or visastatin); squalene synthetase inhibitors; fibrates; bile acid sequestrants, such as questran; niacin; anti-atherosclerotic agents, such as ACAT inhibitors; MTP Inhibitors; calcium channel blockers, such as amlodipine besylate; potassium channel activators; alpha-adrenergic agents; beta-adrenergic agents, such as carvedilol and metoprolol; antiarrhythmic agents; diuretics, such as chlorothiazide, hydrochlorothiazide, flumethiazide, hydroflumethiazide, bendroflumethiazide, methylchlorothiazide, trichloromethiazide, polythiazide, benzothiazide, ethacrynic acid, ticrynafen, chlorthalidone, furosenide, muzolimine, bumetanide, triamterene, amiloride, and spironolactone; thrombolytic agents, such as tissue plasminogen activator (tPA), recombinant tPA, streptokinase, urokinase, prourokinase, and anisoylated plasminogen streptokinase activator complex (APSAC); anti-diabetic agents, such as biguanides (e.g., metformin), glucosidase inhibitors (e.g., acarbose), insulins, meglitinides (e.g., repaglinide), sulfonylureas (e.g., glimepiride, glyburide, and glipizide), thiozolidinediones (e.g., troglitazone, rosiglitazone, and pioglitazone), and PPAR-gamma agonists; mineralocorticoid receptor antagonists, such as spironolactone and eplerenone; growth hormone secretagogues; aP2 inhibitors; phosphodiesterase inhibitors, such as PDE III inhibitors (e.g., cilostazol) and PDE V inhibitors (e.g., sildenafil, tadalafil, and vardenafil); protein tyrosine kinase inhibitors; antiinflammatories; antiproliferatives, such as methotrexate, FK506 (tacrolimus), mycophenolate mofetil; chemotherapeutic agents; immunosuppressants; anticancer agents and cytotoxic agents (e.g., alkylating agents, such as nitrogen mustards, alkyl sulfonates, nitrosoureas, ethylenimines, and triazenes); antimetabolites, such as folate antagonists, purine analogues, and pyrimidine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids (e.g., cortisone), estrogens/antiestrogens, androgens/antiandrogens, progestins, and luteinizing hormone-releasing hormone antagonists, and octreotide acetate; microtubule-disruptor agents, such as ecteinascidins; microtubule-stabilizing agents, such as pacitaxel, docetaxel, and epothilones A-F; plant-derived products, such as vinca alkaloids, epipodophyllotoxins, and taxanes; and topoisomerase inhibitors; prenyl-protein transferase inhibitors; and cyclosporine; steroids, such as prednisone and dexamethasone; cytotoxic drugs, such as azathioprine and cyclophosphamide; TNF-alpha inhibitors, such as tenidap; anti-TNF antibodies or soluble TNF receptor, such as etanercept, rapamycin, and leflunimide; and cyclooxygenase-2 (COX-2) inhibitors, such as celecoxib and rofecoxib; and miscellaneous agents such as, hydroxyurea, procarbazine, mitotane, hexamethylmelamine, gold compounds, platinum coordination complexes, such as cisplatin, satraplatin, and carboplatin.

The compounds provided herein can also be provided as an article of manufacture using packaging materials well known to those of skill in the art. See, e.g., U.S. Pat. Nos. 5,323,907; 5,052,558; and 5,033,252. Examples of pharmaceutical packaging materials include, but are not limited to, blister packs, bottles, tubes, inhalers, pumps, bags, vials, containers, syringes, and any packaging material suitable for a selected formulation and intended mode of administration and treatment.

Provided herein also are kits which, when used by the medical practitioner, can simplify the administration of appropriate amounts of active ingredients to a subject. In certain embodiments, the kit provided herein includes a container and a dosage form of a compound provided herein, including a single enantiomer, a mixture of an enantiomeric pair, an individual diastereomer, or a mixture of diastereomers thereof; or a pharmaceutically acceptable salt, solvate, or prodrug thereof.

In certain embodiments, the kit includes a container comprising a dosage form of the compound provided herein, including a single enantiomer, a mixture of an enantiomeric pair, an individual diastereomer, or a mixture of diastereomers thereof or a pharmaceutically acceptable salt, solvate, or prodrug thereof, in a container comprising one or more other therapeutic agent(s) described herein.

Kits provided herein can further include devices that are used to administer the active ingredients. Examples of such devices include, but are not limited to, syringes, needle-less injectors drip bags, patches, and inhalers. The kits provided herein can also include condoms for administration of the active ingredients.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and propylene glycol; and non-aqueous vehicles, including, but not limited to, corn oil, cottonseed oil, peanut oil, sesame oil, ethyl oleate, isopropyl myristate, and benzyl benzoate.

The disclosure will be further understood by the following non-limiting examples.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); µL (microliters); mM (millimolar); µM (micromolar); Hz (Hertz); MHz (megahertz); mmol (millimoles); hr (hours); min (minutes); TLC (thin layer chromatography); HPLC (high performance liquid chromatography); SCX (strong cation exchange); MS (mass spectrometry); $R_t$ (retention time); $SiO_2$ (silica); THF (tetrahydrofuran); $CD_3OD$ (deuterated methanol); $CDCl_3$ (deuterated chloroform); DCE (dichloroethane); DCM (dichloromethane); DMF (dimethyformamide); DMSO (dimethylsulfoxide); EtOAc (ethyl acetate); $CHCl_3$ (chloroform); DMF (N,N-dimethylformamide); DMA (N,N-dimethyacetamide); MeOH (methanol); EtOH (ethanol); HCl (hydrochloric acid); LiOH (lithium hydroxide); NaOH (sodium hydroxide); KOH (potassium hydroxide); Ac (acetyl); Me (methyl); Et (ethyl); t-Bu (tert-butyl).

For all of the following examples, standard work-up and purification methods known to those skilled in the art can be utilized. Unless otherwise indicated, all temperatures are expressed in ° C. (degrees Centigrade). All reactions conducted at room temperature unless otherwise noted. Synthetic methodologies illustrated in Schemes 4 to 6 are intended to exemplify the applicable chemistry through the use of specific examples and are not indicative of the scope of the disclosure.

Example 1

The Multi-Step Scheme is Shown in FIG. 1

Step (a): Synthesis of Protected Isopropyl-β-D-1-Thioglycoside (2)

To isopropyl-β-D-1-thioglycoside (1) (1 mmol) dissolved in anhydrous pyridine is added slowly with benzoyl chloride (1.1 mmol). A reaction mixture is stirred at 0° C. and the completion of reaction is monitored by a thin layer chromatography ("TLC"). The reaction mixture is then diluted with dichloromethane and transferred to a separating funnel. The reaction mixture is washed with a solution of HCl (1M) to remove excessive pyridine, followed by neutralization with $NaHCO_3$. The solution is further washed with brine for three times (5 mL each). Organic layers are collected, combined and then dried over anhydrous sodium sulfate. A filtrate is concentrated at reduced pressure. A crude product is subjected to column chromatography to obtain pure protected isopropyl-β-D-1-thioglycoside (2).

Step (b): Synthesis of Benzoylated Steroidal Saponin (4)

To a mixture of benzoylated isopropyl-β-D-1-thioglycoside (2) (0.824 mmol) and steroidal aglycone (3) (0.687 mmol) in anhydrous dichloromethane (10 mL), is added with N-iodosuccinimide (NIS) (1.237 mmol) and i-propyl-silyltrifluoromethanesulfonate (i-$Pr_3$SiOTO (0.082 mmol) under nitrogen atmosphere at −42° C. The mixture is stirred under these conditions for 1 hour. The mixture is neutralized with triethylamine and concentrated at reduced pressure. A crude product is subjected to column chromatography to obtain pure benzoylated steroidal saponin (4).

Step (c): Debenzoylation of Steroidal Saponin (4)

To a solution of benzoylated steroidal saponin (4) (0.127 mol) is dissolved in an anhydrous mixture of dichloromethane and methanol (2:1, 21 mL). Sodium methoxide in methanol (1M, 0.1 mL) is added dropwise. A reaction mixture is stirred at room temperature for 3.5 hours and monitored by TLC to ensure completion of reaction. The reaction mixture is then neutralized with Amberlite IR 120 ($H^+$), filtered and concentrated at reduced pressure. A crude product is subjected to column chromatography to obtain the pure product of steroidal saponin (5).

Step (d): Hydrogenation of Steroidal Saponin (5)

To a solution of steroidal saponin (5) dissolved in methanol is added with Pd-charcoal (5%) as a catalyst. Hydrogen is bubbled in and the reaction mixture is stirred at room temperature overnight. A reaction mixture is filtered and concentrated at reduced pressure to obtain the hydrogenated steroidal saponin (6).

Step (e): Dihydroxylation of Steroidal Saponin (5)

To a solution of a steroidal saponin (5) (2 mmol) in tert-butyl alcohol (15 mL) and water (15 mL) is added with $K_3Fe(CN)_6$ (6 mmol), potassium carbonate (6 mmol), and $OsO_4$ solution (0.5 mL, 0.0125 equivalent). A reaction mixture is stirred for 24 hours at ambient temperature. The solution is then added with a proper quantity of $Na_2SO_3$, and stirring is continued for additional several hours. A pale blue solution obtained is then concentrated to dryness at reduced pressure, and the residue is extracted with three portions of diethyl ether. The combined diethyl ether extracts are dried over magnesium sulfate, filtered and then concentrated at reduced pressure. Residue is subjected to column chromatography to obtain pure dihydroxy steroidal saponin (7).

Step (f): Epoxidation of Steroidal Saponin (5)

To a solution of steroidal saponin (5) (1 mmol) in a mixture of methanol and $CHCl_3$ (1:1), meta-chloroperoxybenzoic acid, m-CPBA (1.5 mmol) is added. A reaction mixture is stirred overnight at room temperature and monitored by TLC for completion. The reaction mixture is then neutralized with saturated $NaHCO_3$ and concentrated to dryness at reduced pressure. A crude product is then subjected to column chromatography to obtain pure epoxide steroidal saponin (8). A schematic representation of Example 1 is shown in FIG. 1.

Example 2

Synthesis of Timosaponin A I

Step (a): Synthesis of 3,6-Di-O-benzoylated-isopropyl-β-D-1-thiogalactopyranoside To isopropyl-β-D-1-thioglycoside (1.015 g, 4.2 mmol) dissolved in anhydrous pyridine (7 mL) was added slowly with benzoyl chloride (0.982 mL, 8.5 mmol). A reaction mixture was stirred at 0° C. and the completion of reaction is monitored by TLC. The reaction mixture was then diluted with dichloromethane and transferred to a separating funnel. The reaction mixture was washed with a solution of HCl (1M, 10 mL) to remove excessive pyridine, followed by neutralization with a solution of $NaHCO_3$. The solution was further washed with brine for three times (5 mL each). Organic layers were collected and dried over anhydrous sodium sulfate. Filtrate was concentrated to dryness at reduced pressure. A crude product was then subjected to column chromatography (silica gel, 60 Mesh) using dichloromethane and EtOAc (25:1) as the eluant to obtain pure 3,6-di-O-benzoylated-isopropyl-β-D-1-thiogalactopyranoside (0.98 g). The product was characterized by the following analytical data: $^1$H NMR (300 MHz, $CDCl_3$): δ 8.09 (d, J=7.2 Hz, 2H), 8.01 (d, J=7.2 Hz, 2H,), 7.54-7.59 (m, 2H), 7.40-7.45 (m, 4H), 5.18 (dd, J=9.6 Hz, J=3.2 Hz, 1H), 4.52-4.62 (m, 3H), 4.25-4.28 (m, 1H), 3.98-4.08 (m, 2H), 3.24 (sep, J=6.7 Hz, 1H), 2.66 (d, J=5.6 Hz, 1H), 2.60 (d, J=2.6 Hz, 1H), 1.33 (t, J=6.6 Hz, 6H). $^{13}$C NMR (125 MHz, $CDCl_3$): δ 166.45, 166.05, 133.49, 133.33, 129.93, 129.74, 129.55, 129.50, 128.51, 128.44, 86.73, 76.48, 76.07, 68.07, 67.56, 63.07, 36.24, 24.27, 23.89. ESI-MS m/z (rel. int.) 914.9 $[2M+Na]^+$ (90), 469.1 $[M+Na]^+$ (100).

Step (b): Synthesis of Benzoylated Timosaponin A I

To a mixture of 3,6-di-O-benzoylated-isopropyl-β-D-1-thiogalactopyranoside (368 mg, 0.824 mmol) and sarsasapogenin (286 mg, 0.687 mmol) in anhydrous dichloromethane (10 mL), was added NIS (277 mg, 1.237 mmol) and i-$Pr_3$SiOTf (22.2 μL, 0.082 mmol) under $N_2$ atmosphere at −42° C. The mixture was stirred under these conditions for 1 hour. The reaction mixture was neutralized with TEA and then concentrated at reduced pressure. The crude product is subjected to column chromatography (silica gel, 60 Mesh) using dichloromethane and methanol (50:1) as eluant. Pure benzoylated timosaponin A I (106 mg) was obtained. The product was characterized by the following analytical data: $^1$H NMR (400 MHz, $CDCl_3$): δ 8.10 (d, J=7.2 Hz, 2H), 8.03 (d, J=7.2 Hz, 2H,), 7.55-7.60 (m, 2H), 7.43-7.48 (m, 4H), 5.18 (dd, J=9.6 Hz, J=3.2 Hz, 1H), 4.40-4.61 (m, 4H), 4.26-4.29 (m, 1H), 3.94-4.13 (m, 4H), 3.30 (d, J=11.0 Hz, 1H), 2.37 (d, J=5.6 Hz, 1H), 2.27 (d, J=2.2 Hz, 1H), 1.15-2.27 (m, 27H), 1.08 (d, J=7.1 Hz, 3H), 0.99 (d, J=6.7 Hz, 3H), 0.95 (s, 3H), 0.76 (s, 3H). $^{13}$C NMR (125 MHz, $CDCl_3$): δ 166.40, 166.04, 133.43, 133.30, 129.90, 129.75, 129.63, 129.60, 128.49, 128.45, 109.75, 101.89, 81.02, 75.34, 75.28, 72.29, 69.62, 67.41, 65.16, 62.62, 62.13, 56.45, 42.14, 40.69, 40.30, 40.17, 37.16, 35.29, 35.07, 31.76, 30.42, 30.26, 27.09, 26.64, 26.55, 26.36, 25.97, 25.79, 23.90, 20.88, 16.49, 16.05, 14.34. ESI-MS 1591.1 $[2M+H_2O+H]^+$ (50), 804.1 $[M+H_2O]^-$ (100), 787.3 $[M+H]^+$ (100).

Step (c): Debenzyolation of Benzyolated Timosaponin A I

Figure 2:
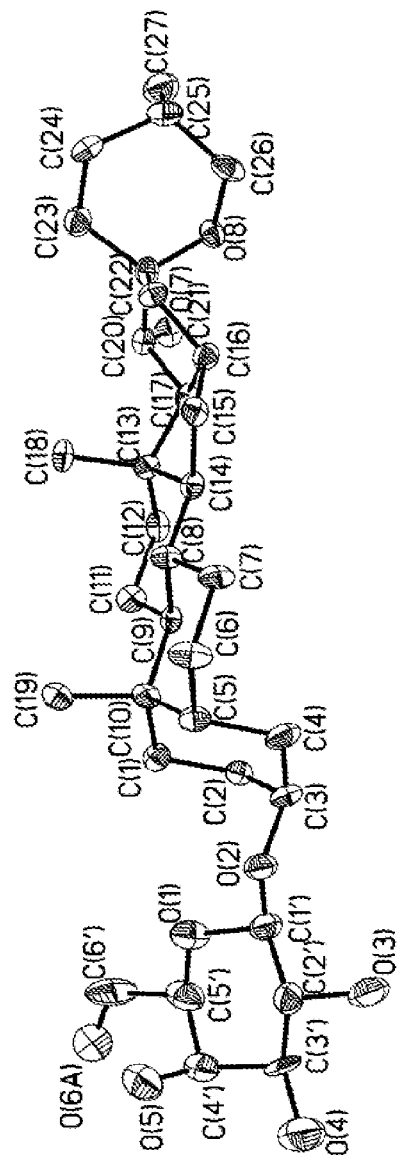
FIG. 2 depicts an ORTEP diagram of Timosaponin A I.

Benzyolated timosaponin A I (100 mg, 0.127 mmol) was dissolved in anhydrous mixture of dichloromethane and methanol (2:1; 21 mL,) followed by dropwise addition of a solution of sodium methoxide in methanol (1M, 0.1 mL) at room temperature. A reaction mixture was stirred at room temperature for 3.5 hours and monitored by TLC (using dichloromethane and methanol (9:1) as developing solvents) to ensure completion of reaction. The reaction mixture was then neutralized with Amberlite IR 120 ($H^+$), filtered and concentrated to dryness at reduced pressure. A crude product was then subjected to column chromatography (Silica gel, Mesh 60) using dichloromethane and methanol (9:1) as eluant. Pure product of timosaponin A I (66 mg) was obtained. The product was characterized by the following analytical data: $^1$H NMR δ ppm (500 MHz, $d_4$-MeOH, 50° C.): 0.79 (s, 3H), 0.98 (s, 3H), 0.99 (d, 8.1, 3H), 1.09 (d, 7.0, 3H), 3.31 (dd, 1.6, 3.2, 1H), 3.45-3.53 (m, 3H), 3.73, (d, 6.0, 2H), 3.85 (d, 2.6, 1H), 3.94 (dd, 2.7, 11.0, 1H), 4.05 (m, 1H), 4.28 (d, 7.5, 1H). $^{13}$C NMR δ ppm (500 MHz, $d_4$-MeOH, 50° C.): 111.2, 103.7, 82.6, 76.7, 76.1, 75.5, 73.0, 70.6, 66.3, 64.0, 62.7, 57.9, 43.7, 42.0, 41.7, 41.6, 38.2, 37.0, 36.3, 32.9, 31.7, 31.5, 28.7, 27.9, 27.8, 27.7, 27.3, 26.9, 24.3, 22.2, 17.0, 16.5, 14.7. HREIMS m/z (rel. int.) 578.3813 [$M^+$, Δ=0.5 mmu for $C_{33}H_{54}O_8$] (2), 399.3 (20), 344.2 (7), 329.2 (11), 302.2 (9), 285.2 (23). ESI-MS m/z: 601.5 $[M+Na]^-$ (35), 1179.5 $[2M+Na]^-$ (100). The chemical structure of timosaponin A I was further confirmed by X-ray crystallography after recrystalizing from methanol. The ORTEP diagram of timosaponin A I is shown in FIG. 2.

Example 3

Proposed Syntheses for New Compounds 11, 13, 15, 17, 19 of Formula I (Scheme II)

Step (a): Benzyolation of Steroid (3)

A solution of benzoyl chloride (BzCl, 78.9 mL, 0.679 mol) is added to a stirring solution of steroid (3) (0.241 mol) in dried dichloromethane (400 mL) and dried pyridine in an ice bath. The reaction mixture is warmed to room temperature and stirred for 24 hours. The reaction solution is concentrated at reduced pressure. The crude oil product is recrystallized from $CH_2Cl_2$-EtOAc to afford benzoylated steroid (9).

Step (b): Hydroxylation of Steroid (9)

To a stirred solution of steroid (9) (104 mmol) in tetrahydrofuran (450 mL) at −10° C., under $N_2$, is added $BH_3$.THF complex (1M) in THF (260 mmol). After completing the addition, the mixture is stirred at room temperature for 3 hours. Water (500 mL) is cautiously added dropwise followed by $NaBO_3.4H_2O$ (204 mmol). After stirring at room temperature for overnight, the mixture is filtered. A solid is washed with tetrahydrofuran and then discarded. Two liquid phases, including an aqueous layer, are separated. The aqueous layer is saturated with sodium chloride and extracted with tetrahydrofuran for three times (200 mL). Combined organic extracts are dried over sodium chloride and sodium sulfate, filtered, and then evaporated to dry at reduced pressure. A crude product is crystallized from EtOAc:MeOH to obtain 5=, 6α- or 5β, 6β-hydroxylated steroid (10).

Step (d): Bromination of Hydroxylated Steroid (10)

Triphenylphosphine (0.003 mol) is added to a stirring solution of hydroxylated steroid (10) (0.002 mol) in anhydrous tetrahydrofuran (40 mL) and a reaction mixture is cooled to −18° C. N-Bromosuccinimide (1.210 g, 0.007 mol) is added in three parts to the reaction mixture over 1 hour and it is then allowed to warm to room temperature. After 1.5 hours, when TLC analysis showed no more starting material, the reaction mixture is poured into HCl solution (1M, 150 mL) and extracted with ethyl acetate (3×100 mL). Combined organic layers is washed with water for two times (100 mL each) and brine (100 mL), dried over magnesium sulfate, filtered and then evaporated under reduced pressure. A crude product is subjected to column chromatography to obtain pure brominated steroid (12).

Step (f): Tosylation of Hydroxylated Steroid (10)

Hydroxylated steroid (10) (10 mmol) is dissolved in chloroform (10 mL) and cooled in an ice bath (0° C.). Pyridine (1.62 mL, 20 mmol) is then added, followed by the addition of p-toluenesulfonyl chloride (TsCl) (2.85 g, 15 mmol) in small portions with constant stirring. The completion of reaction is monitored by TLC. Diethyl ether (30 mL) and water (7 mL) are added and an organic layer is washed successively with HCl (2N), NaHCO$_3$ (5%) and water and then dried with magnesium sulfate. The solvent is removed under reduced pressure and a crude product is subjected to column chromatography to obtain pure tosylated steroid (14).

Step (g): Cyanation of Tosylated Steroid (14)

Tosylated steroid (14) (8.44 mmol) and sodium cyanide (830 mg, 16.9 mmol) are stirred in DMSO (50 mL) at 90° C. for 5 hours. A reaction mixture is extracted using EtOAc/H$_2$O, combined organic phases are dried with magnesium sulfate and the solvent is evaporated at reduced pressure. A crude product is subjected to column chromatography to obtain a purified nitrile steroid (16).

Step (j): Oxidation of Hydroxylated Steroid (10)

Pyridinium chlorochromate (FCC) (851 mg, 3.95 mmol) is added to a solution of hydroxylated steroid (10) (1.53 mmol) in dichloromethane (40 mL). A reaction mixture is stirred at 23° C. for 2 hours and then diluted with tert-butyl methyl ether (40 mL). The reaction mixture is then filtered through SiO$_2$ (5 cm, hexane/tert-butyl methyl ether) the solvent is evaporated at reduced pressure to yield ketone steroid (18) Steps c, e, h, I and k are glycosylation of steroid (10), (12), (14), (16) and (18) respectively. The procedures are similar to the glycosylation steps in Example 1. A schematic representation of Example 3 is shown in FIG. 3.

Example 4

Proposed Syntheses for New Compounds 20-22 of Formula II (Scheme III)

Step (a): Ring Opening of Steroid Saponin (5)

Anhydrous AlCl$_3$ (0.1 mol) is placed in a 500-mL, 3-necked flask equipped with a sealed stirrer, reflux condenser protected by a drying tube and a pressure-equalized addition funnel. The flask is cooled in an ice-bath and Mallinckrodt anhydrous ether (100 mL, pre-cooled for 30 minutes in a refrigerator) is added slowly with stirring. After all AlCl$_3$ is dissolved, standardized ethereal LiAlH$_4$ (1.0 M, 25 mL, 0.025 mol) is added with continued cooling and stirring. 30 minutes later, steroid saponin (5) (0.05 mol) dissolved in anhydrous ether (100 mL) is added and a reaction mixture is stirred for 2 hours after the removal of ice bath. The aluminium complexes are then destroyed by adding dropwise aqueous H$_2$SO$_4$ (10%, 100 mL) with cooling. A clear ether layer is separated and an aqueous layer is extracted with ether (3×50 mL). Combined ether layers are dried over anhydrous potassium carbonate and then concentrated at reduced pressure. A crude product is subjected to column chromatography to obtain hydroxyl steroid saponin (20).

Step (b): Methyl Sulfonation of Steroid Saponin (20)

A dry 50-mL round bottomed flask is outfitted with a stir bar, gas inlet adapter and a rubber septum. The assembly is flame dried under vacuum and cooled under N$_2$. Hydroxyl steroid saponin (20) (0.44 mmol) and dichloromethane (6 mL) are sequentially added to the flask and a mixture is allowed to stir and cool in an ice bath. Triethylamine (1.11 mmol) and methanesulfonyl chloride (0.66 mmol) are sequentially added to the cooled reaction mixture and is then allowed to stir for 30 minutes. The reaction mixture is diluted with hexane and poured into ice water. An organic layer is separated and an aqueous layer extracted three times with hexane. The organic layers are combined, dried over sodium sulfate and then concentrated at reduced pressure. A residue is then subjected to column chromatography to obtain methyl sulfonated steroid saponin (21).

Step (c): Reduction of Methyl Sulfonated Steroid Saponin (III)

A dry 50-mL round bottomed flask is outfitted with a stir bar, gas inlet adapter and a rubber septum. The assembly is flame dried under vacuum and cooled under N$_2$. Methyl sulfonated steroid saponin (21) (0.41 mmol), tetrahydrofuran (4 mL) and lithium triethylborohydride (4.0 mL of 1.0 M solution in THF, 4.0 mmol) are sequentially added to the flask and then allowed to stir for 3 hours. A reaction mixture is quenched with water, partitioned between brine and hexanes, and then extracted three times with hexanes. Organic layers are combined, dried over sodium sulfate and concentrated at reduced pressure. A residue is then subjected to column chromatography to obtain purified steroidal saponin (22). A schematic representation of Example 4 is shown in FIG. 4.

Example 5

Effect of Timosaponin A-III on the Aβ Production in SweAPP N2A Cells

Neuro-2A cells expressing Swedish mutants of ("SweAPP N2A cells") was cultured in minimal essential medium with glutamine (2 mM), pyruvate (2 mM) and fetal bovine serum (10%). Cells were seeded at 6-well plate at $1 \times 10^6$ cells/mL and grown overnight. The medium was replaced. Different concentrations (0.6, 1, 3, 5 and 10 µM) of timosaponin A-III as shown in Table 1 were added into different wells and incubated for 18 hours. Control experiment was done by replacing timosaponin A-III with DMSO.

Figure 6:
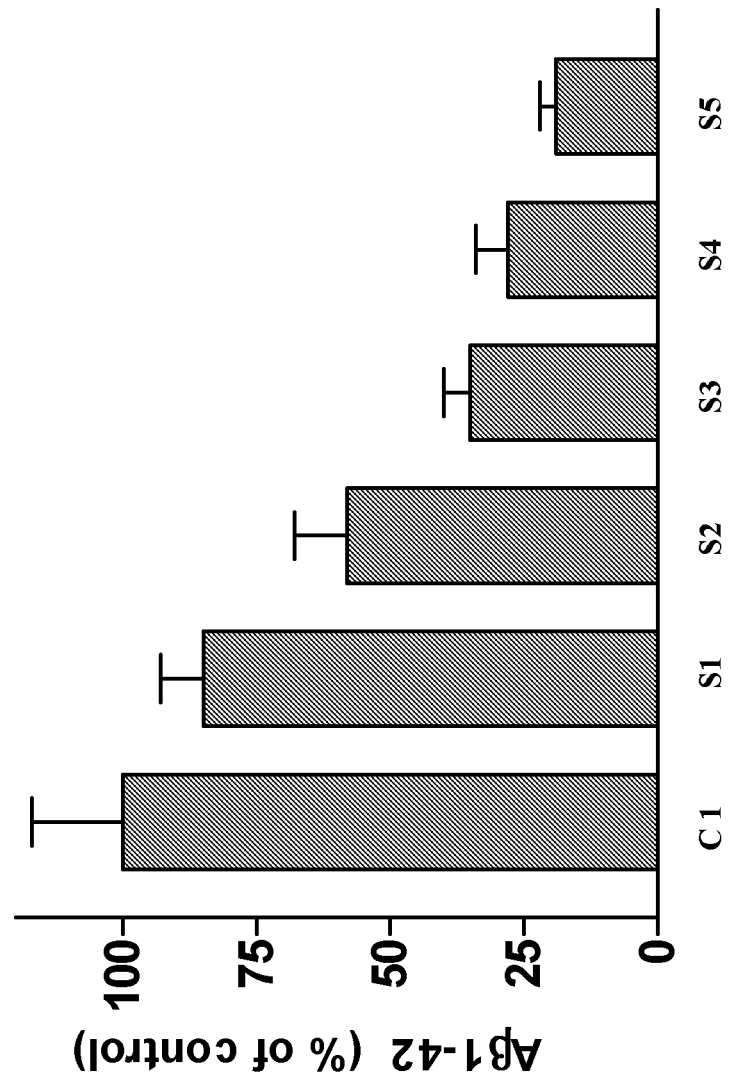
FIG. 6 depicts a result of ELISA of effects of Timosaponin A-III on the Aβ production in sweAPP N2A cells.

Conditioned medium was diluted with 2 part volume of ELISA diluents. $A\beta_{1-42}$ concentrations were determined by using human $A\beta_{1-42}$ ultrasensitive ELISA kit (manufactured by Invitrogen). FIG. 6 shows the relative concentrations of $A\beta_{1-42}$ in the samples compared with the concentration of $A\beta_{1-42}$ in C1.

TABLE 1

| Sample No. | Concentration of Timosaponin A-III (µM) | Concentration of DMSO |
| --- | --- | --- |
| S 1 | 0.6 | 0 |
| S 2 | 1 | 0 |
| S 3 | 3 | 0 |
| S 4 | 5 | 0 |
| S 5 | 10 | 0 |
| C 1 | 0 | 0.1% |

SweAPP N2A cells constitutively produce and secrete Aβ from the Swedish mutant APP which is susceptible to cleavage by beta-site APP-cleaving enzyme ("BACE"). Treatment of cells with timosaponin A-III resulted in a concentration dependent reduction of $A\beta_{1-42}$ peptide secretion as determined by ELISA, with an $IC_{50} = 2$ µM.

The $IC_{50}$ is defined as the concentration of compound required to reduce the enzyme activity by 50% under the condition of the assay.

Timosaponin A-III did not affect the cell viability at concentrations that significantly inhibited Aβ production. Our results suggest that timosaponin A-III is an effective micromolar inhibitor of Aβ production and its potency appears to be among the lowest of those derived from natural products or TCM (e.g. green tea polyphenols, ginsenosides and resveratrol).

Example 6

Immunoblot Analysis

Cells obtained from Example 5 were washed with phosphate buffered saline and lysed with buffer containing Tris-Cl (50 mM, pH 7.4), NaCl (150 mM), TRITON™X-100 (1%) supplemented with protease inhibitors. Equal amount of proteins (30 µg) was resolved by 16.5% Tris-tricine gels and then transferred to nitrocellulose membrane with 0.2 µm pore size. For detection of secreted Aβ, 50 µL of the conditioned medium was mixed with sodium dodecyl sulfate ("SDS") sample buffer and resolved accordingly. The membrane was blocked with Tris-buffered saline containing TWEEN™20 (0.1%) and bovine serum albumin ("BSA") (3%) and then incubated with primary antibodies at 4° C. overnight, followed with appropriate secondary antibodies for 2 hours. The primary antibodies used included rabbit APP c-terminal antibody with 1:5000 dilution (obtained from Merck Bioscience) for detection of full length ("FL") and CTFs, and mouse monoclonal 6E10 (obtained from Covance) for detection of secreted Aβ. The immunoreactivities were detected using enhanced chemiluminescence reagents (manufactured by GE Health care).

Figure 7:
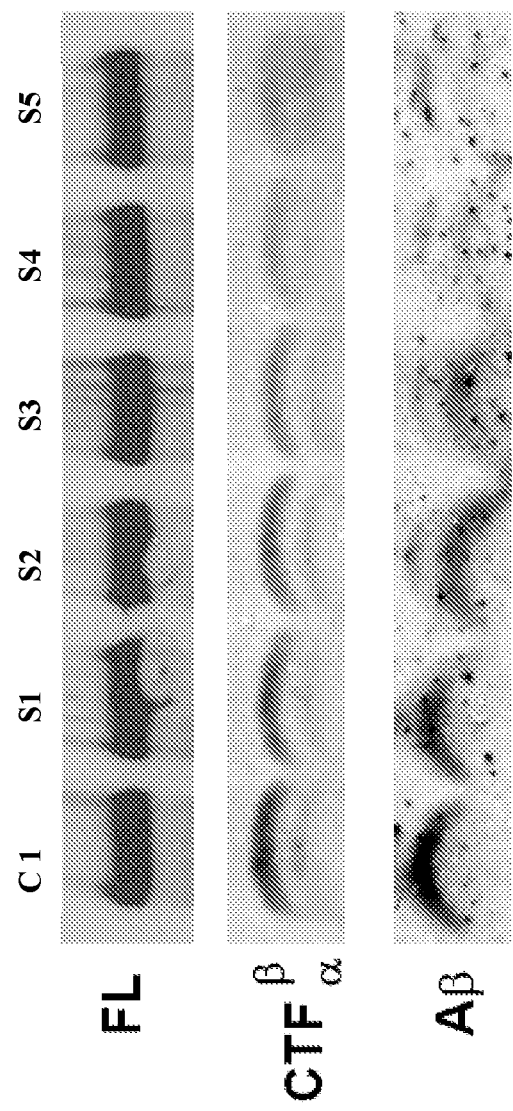
FIG. 7 depicts a result of an immunoblot analysis of an effect of Timosaponin A-III on APP processing in sweAPP N2A cells.

Immunoblot analysis revealed that in SweAPP N2A cells, both FL, α-CTF, β-CTF APP were shown in FIG. 7. In timosaponin A-III-treated cells, the intracellular APP β-CTF expression was significantly decreased without significant changes in FL APP expression. The reduction of intracellular APP β-CTF expression of timosaponin A-III-treated cells was also accompanied by concomitant decrease in Aβ immunoreactivities in the conditioned medium. These results suggest that timosaponin A-III specifically inhibit the amyloidogenic pathway through inhibition of β-cleavage of APP.

A possible cause of reduction of β-cleavage of APP is an inhibition of BACE activity. In cells treated with timosaponin A-III, there was no change in BACE activity in cell lysates. Furthermore, the activity of purified BACE1 enzyme was also not affected by the presence of timosaponin A-III up to 100 µM.

Example 7

The procedures were similar to Example 5 except timosaponin A-III (2 µM and 5 µM), timosaponin AI (20 µM and 50 µM) and sarsasapogenin ("SSG") (20 µM and 50 µM) were used instead of timosaponin A-III (0.6, 1, 3, 5 and 10 µM) as shown in Table 2.

TABLE 2

| Sample No. | Concentration (µM) | Concentration of DMSO |
| --- | --- | --- |
| S 6 | 2 µM Timosaponin A-III | 0 |
| S 7 | 5 µM Timosaponin A-III | 0 |
| S 8 | 20 µM Timosaponin AI | 0 |
| S 9 | 50 µM Timosaponin AI | 0 |
| S 10 | 20 µM SSG | 0 |
| S 11 | 50 µM SSG | 0 |
| C2 | 0 | 0.1% |

Figure 8:
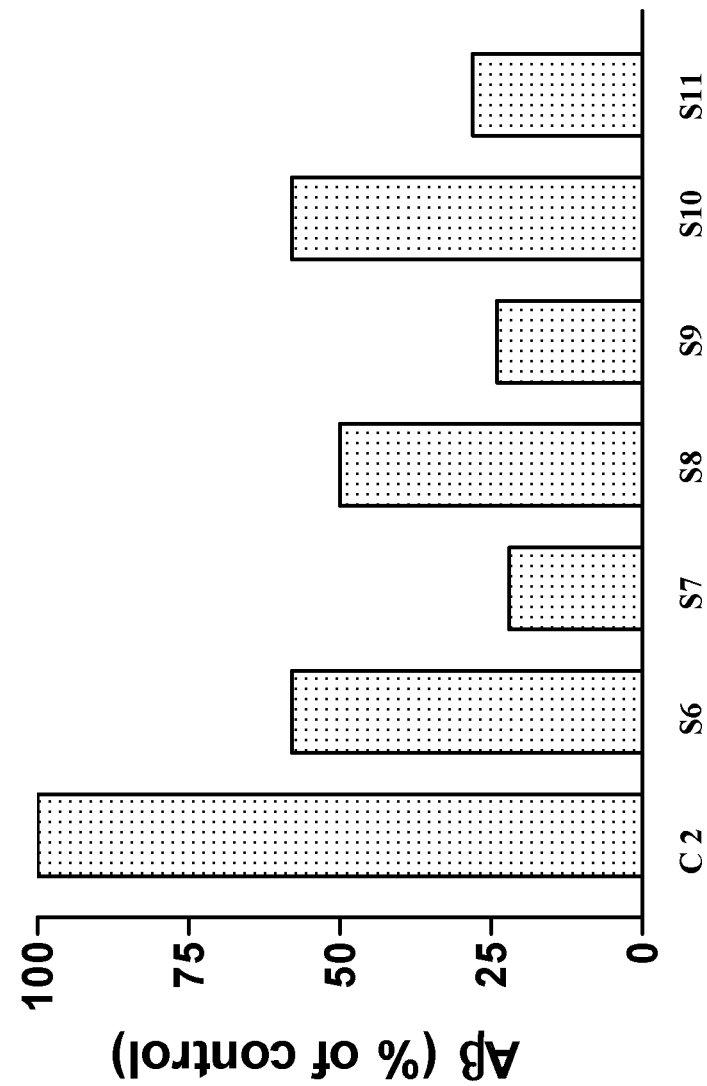
FIG. 8 depicts effects of Timosaponins and derivatives on the Aβ production in sweAPP N2A cells.

FIG. 8 shows the relative concentrations of $A\beta_{1-42}$ in the samples compared with the concentration of $A\beta_{1-42}$ in C2. Analogues of timosaponin including timosaponin AI and SSG were also tested for their effects on the Aβ production. Timosaponin AI and SSG exhibited inhibition of Aβ production with $IC_{50}$ of about 20 µM.

Example 8

Figure 9:
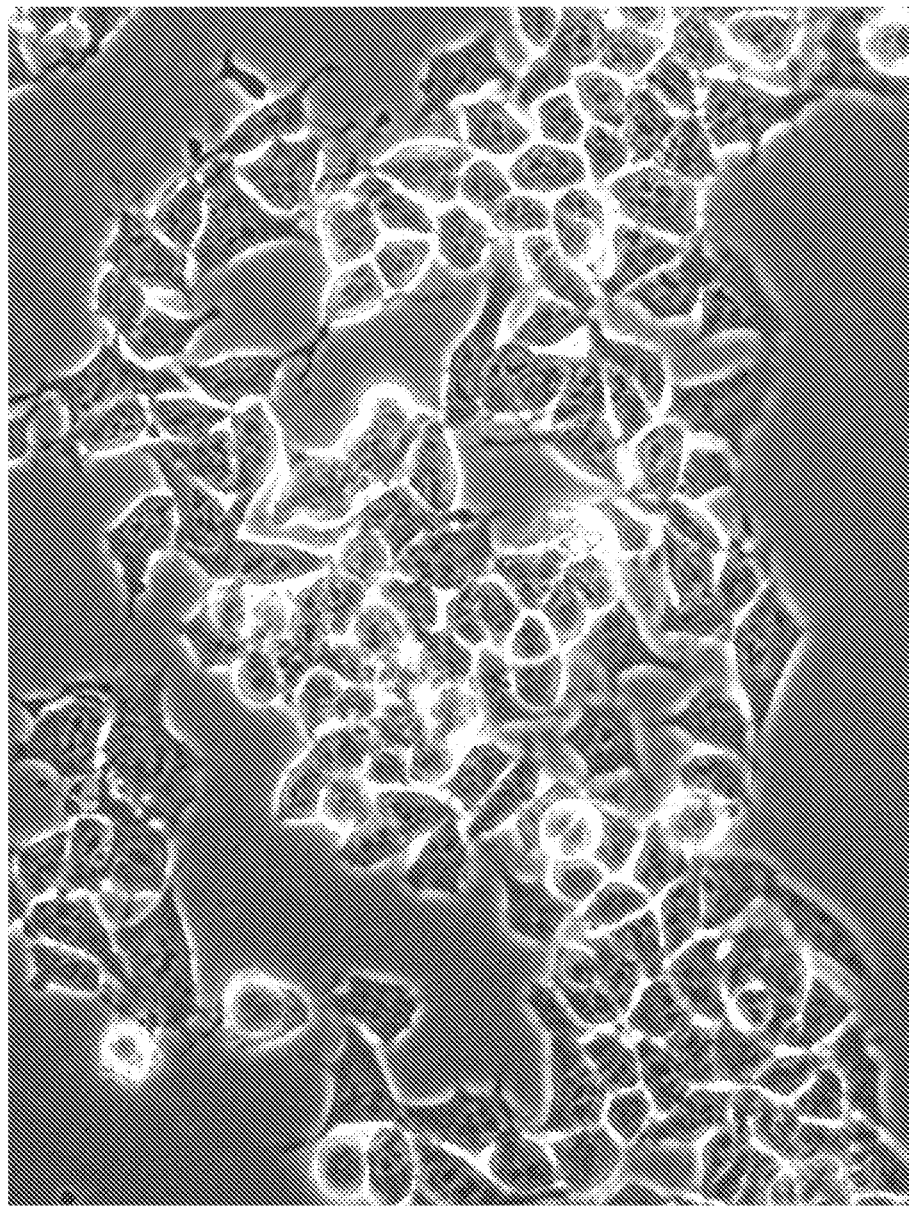
FIG. 9 depicts a light microscopic examination of N2A cells without an effect of Timosaponin A-III.
Figure 10:
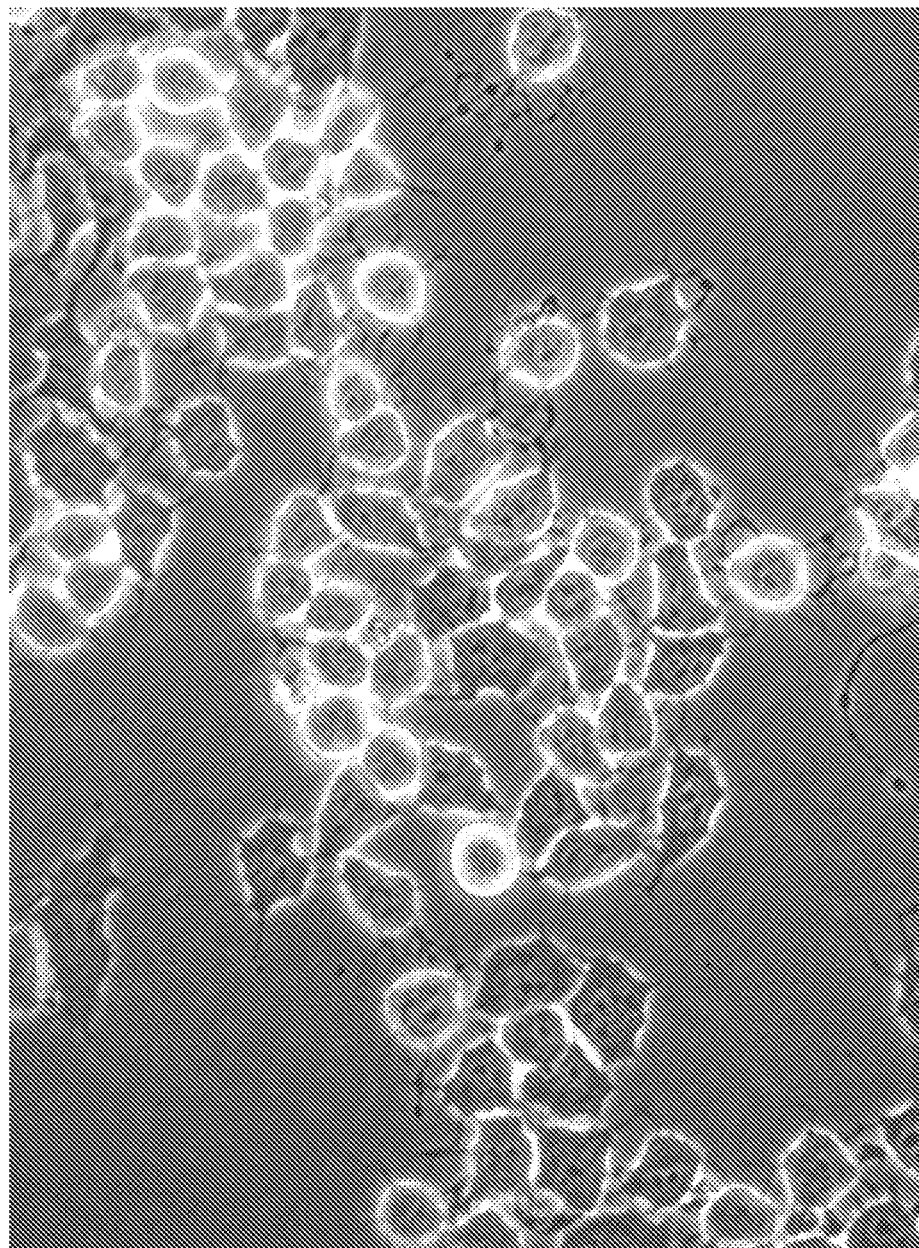
FIG. 10 depicts a light microscopic examination of N2A cells with an effect of Timosaponin A-III.

Regeneration of neurons represents a promising strategy for drugs targeted against neurodegenerative disorders such as Alzheimer's disease. The effect of timosaponin A-III on neurite outgrowth of N2A cells were examined. FIG. 9 shows the treatment of N2A cells with DMSO for 18 hours. FIG. 10 shows the treatment of N2A with timosaponin A-III (5 µM) for 18 hours. Treatment with timosaponin A-III resulted in significant extension and branching neuritis.

Example 9

Figure 11:
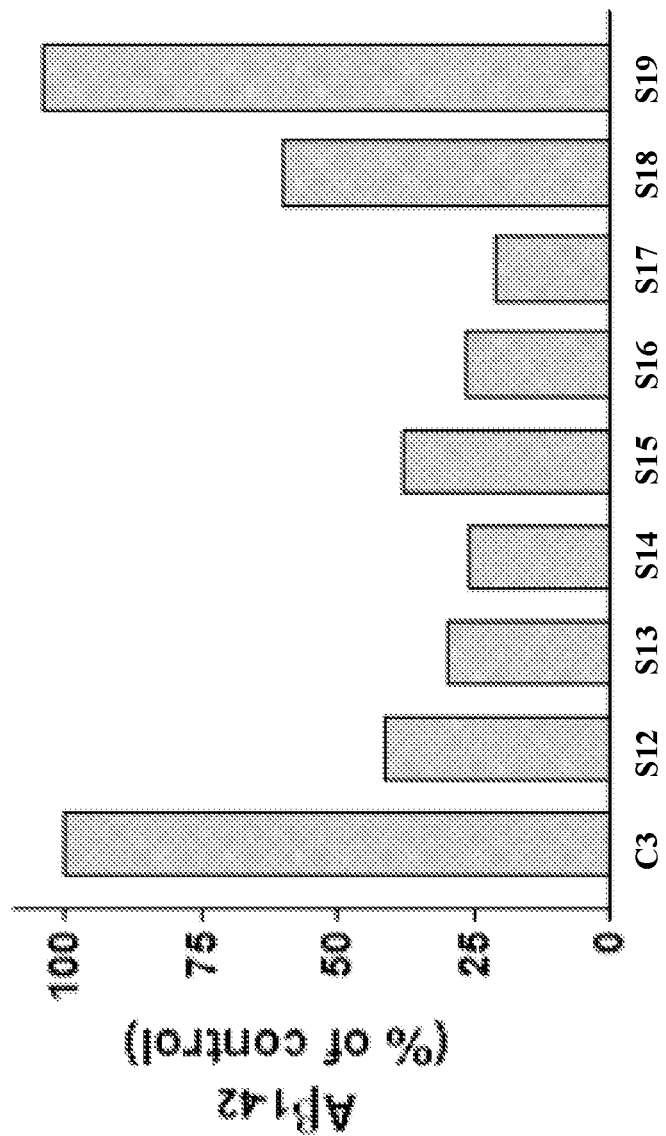
FIG. 11 depicts a result of ELISA of effects of Timosaponin A-III, Timosaponin A-I, SSG and DSG on the production in sweAPP N2A cells.

The procedures were similar to Example 5 except timosaponin A-III (2.5 µM, 5 µM and 10 µM), timosaponin AI (5 µM, 10 µM and 20 µM), SSG (50 µM) and diosgenin ("DSG") (50 µM) were used instead of timosaponin A-III (0.6, 1, 3, 5 and 10 µM) as shown in Table 3. FIG. 11 shows the relative concentrations of $A\beta_{1-42}$ in the samples compared with the concentration of $A\beta_{1-42}$ in $C_3$.

TABLE 3

| Sample No. | Concentration (µM) | Concentration of DMSO |
|---|---|---|
| S12 | 2.5 µM Timosaponin A-III | 0 |
| S13 | 5 µM Timosaponin A-III | 0 |
| S14 | 10 µM Timosaponin A-III | 0 |
| S15 | 5 µM Timosaponin AI | 0 |
| S16 | 10 µM Timosaponin AI | 0 |
| S17 | 20 µM Timosaponin AI | 0 |
| S18 | 50 µM SSG | 0 |
| S19 | 50 µM DSG | 0 |
| C3 | 0 | 0.1% |

Sarsasapogenin linked to galactose-glucose disaccharide is an effective inhibitor of Aβ production ($IC_{50}$=2.5 µM). Sarsasapogenin linked to galactose monosaccharide (i.e., timosaponin AI) has slightly lower Aβ-lowering activity ($IC_{50}$=5 µM). The aglycone sarsasapogenin has weaker activity ($IC_{50}$=50 µM).

Example 10

Characterization of Anti-Amyloidogenic Action of Timosaponins and Derivatives

The amyloidogenic pathway involves multiple components of proteolysis and cell compartmentalization of APP. The mechanism of action of anti-amyloidogenic compounds can be deduced through examination of several crucial steps in the APP metabolism.

a. Cellular Model

Neuro-2A neuronal cells stably transfected with Swedish mutant of APP (N2A SweAPP) are used as the cellular model for studying how timosaponins reduce the production of Aβ. N2A SweAPP cells constitutively produce Aβ from the Swedish mutant of APP which is susceptible to intracellular cleavage by β-secretase.

b. Aβ Production and APP Processing

Cells were treated with timosaponins or other test compounds, and the conditioned medium was collected and subjected to measurement of secreted Aβ and N-terminal secreted APP (sAPPα and sAPPβ) by ELISA using specific antibodies pair targeting to respective fragments. Lysates from cells treated with timosaponins were subjected to immunoblot analysis using antibodies against c-terminal of APP to detect the full length APP, α-CTF and β-CTF. Cell viability and cytotoxicity are examined by MTT and LDH release assays, respectively.

c. APP Cleavage Enzymes

To examine the effects of timosaponins on the APP cleavage enzymes, α-, β-, and γ-secretase activities in lysates from cells treated with timosaponins or in cell lysates directly treated with the compound are determined using secretase-specific peptide substrates conjugated to fluorogenic reporter molecules. Alternatively, the in vitro β- and γ-secretase activities are determined by detecting the cleaved products of APP in the P2 membrane fractions by immunoblots.

The association of APP with its processing proteins is examined by immunoprecipitation of APP followed by immunoblot analysis with the secretases component proteins and other interacting proteins. In addition, biological mass spectrometry analysis is performed on the co-immunoprecipitated complex to identify the interacting proteins.

Example 10A

The Effect of Timosaponin A-III on Exogenous Aβ

Human SH-SY5Y neuronal cells were transfected with microtuble-associated protein light chain 3 tagged with monomeric red fluorescence protein (mRFP-LC3) are treated with fluorophore labeled $A\beta_{1-42}$ peptide for 1 hour followed by replacement of medium containing 5 µM of Timosaponin A-III or control (0.05%) for 16 hours. Fluorescence microscopic examination revealed that the fluorophore labeled $A\beta_{1-42}$ was significantly colocalized with the mRFP-LC3 associated autophagic compartments in Timosaponin A-III treated cells.

Example 11

Animal Studies a. Evaluation of Oral Dosing and Determination of Saponin and Aβ Levels in Mice Balb/c mice are used in the preliminary studies to determine the dosage and treatment time. Tentatively, the mice are administered with timosaponins (TAIII or TAI) or vehicle at 1-50 mg/kg/day via oral gavage for short term (1-7 days) or doped chow for long term (1 to 3 months). The health condition and survival are monitored. At the end of the experiment, the mice are sacrificed and blood is collected for determination of the saponin levels by LC-MS. Brain hemispheres are harvested for measurement of Aβ content by standard ELISA.

b. Tg2576 Mouse Model

Tg2576 mouse line harbouring Swedish double mutation (K670/M671L) on the human APP 695 transgene is used as AD model. These mice express high levels of human Aβ in the brains and show spatial memory impairment. The Tg2576 transgenic mice are obtained from Taconic Farms, Inc. (model 2789). After settling the animal importing, housing, breeding (to 129S6 background) and screening procedures, the animals are treated with timosaponins with the dosages and treatment time determined in the pilot experiments performed on Balb/c mice. The brain Aβ content after treatment of timosaponins is measured by both ELISA and immunohistochemical staining Behavioral test based on novel object recognition, Y maze and Morris water maze is performed.

Example 12

Chemistry a. Semi-Synthesis of Timosaponin A I (TAI)

Figure 5:
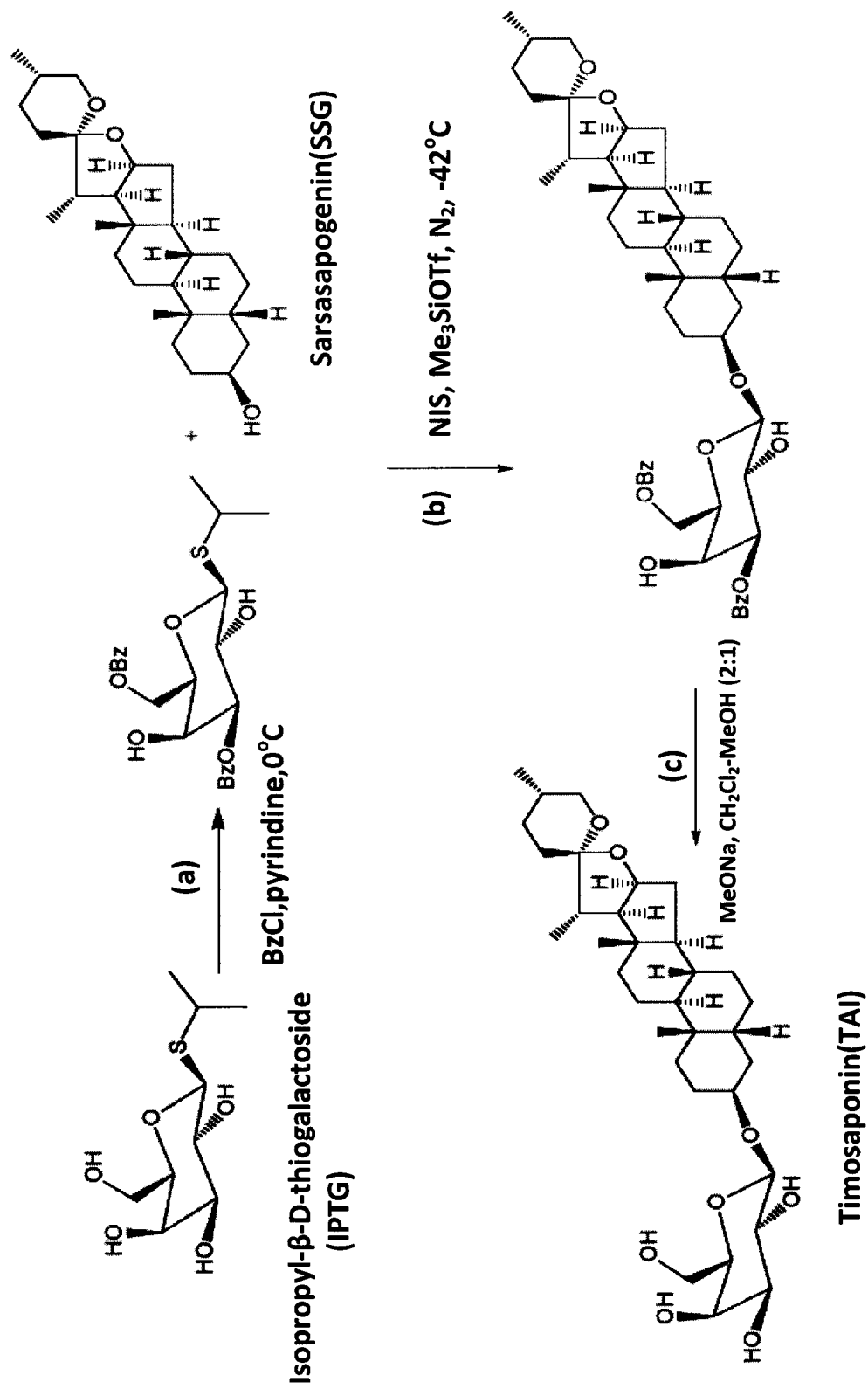
FIG. 5 depicts a synthetic scheme for Timosaponin A I.

SSG and TAIII are currently available from commercial market but the availability of TAI is problematic. The abundance of TAI in *Anemarrhena asphodeloides* is much less than that of TAIII, indicating that the isolation of TAI (0.002% yield) from natural resource is labour intensive and time consuming and thereby semi-synthesis of TAI in the long run is recommended (FIG. 5). There are three major steps: (a) protecting Isopropyl-β-D-thiogalactoside (IPTG), (b) coupling protected IPTG with SSG and (c) deprotecting coupled IPTG. The starting materials involved for the synthesis of TAI including IPTG are commercially available with reasonable price, suggesting an efficient and cost-optimum synthesis is possible. The structure elucidation of TAI was ascertained based on 1-dimensional ($^1$H NMR, $^{13}$C NMR, $^{13}$C DEPT) and two-dimensional NMR (HSQC, HMBC, $^1$H-$^1$H COSY and NOESY). The $^1$H and $^{13}$C chemical shifts of $C_3$ position of SSG were found diagnostically downfield shifted from δ4.11 ppm and δ67.1 ppm to δ3.49 ppm and δ76.7 ppm in TAI. Remarkably, the $^1$H NMR at δ4.28 ppm with a coupling constant of 7.5 Hz indicated a β-configuration for the glycosidic bond of TAI. TAI was also qualitatively confirmed by high resolution mass spectroscopy showing a molecular mass of $C_{33}H_{54}O_8$ [M$^-$ 578.3813, Δ=0.5 mmu]. The relative stereochemistry of TAI after recrystalizing from methanol was unambiguously verified by X-ray analysis as shown in FIG. 2.

b. Synthesis of Open-Ring Derivatives of SSG

SSG is a spirostan sapogenin and the F-ring appears to be a crucial radical in bioactive saponins We herein propose that the F-ring in SSG/TAI/TAIII as shown below is one of the essential factors in inhibiting Aβ production.

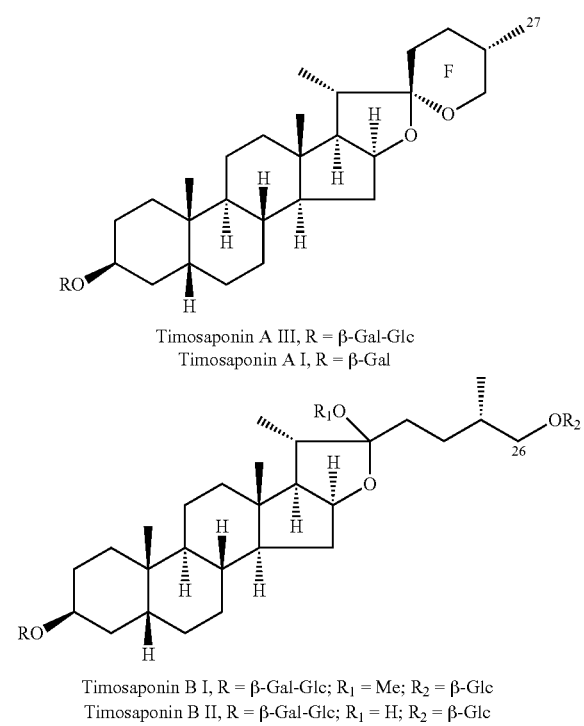

Timosaponin A III, R = β-Gal-Glc
Timosaponin A I, R = β-Gal

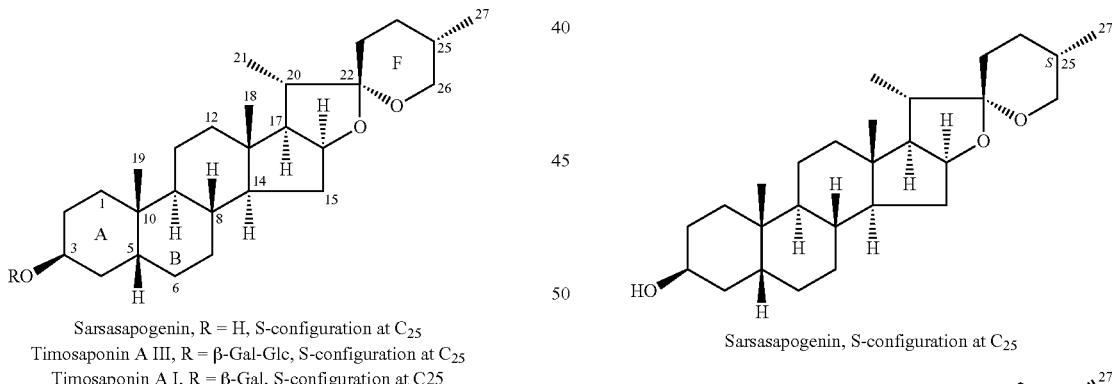

Timosaponin B I, R = β-Gal-Glc; $R_1$ = Me; $R_2$ = β-Glc
Timosaponin B II, R = β-Gal-Glc; $R_1$ = H; $R_2$ = β-Glc c. The Role of S- and R-Configuration at $C_{25}$ Smilagenin, which is an enantiomer of SSG having an R-configuration at $C_{25}$ where the $C_{27}$-methyl group attached to is equatorially orientated as shown below, is studied.

Sarsasapogenin, R = H, S-configuration at $C_{25}$
Timosaponin A III, R = β-Gal-Glc, S-configuration at $C_{25}$
Timosaponin A I, R = β-Gal, S-configuration at C25

Figure 12:
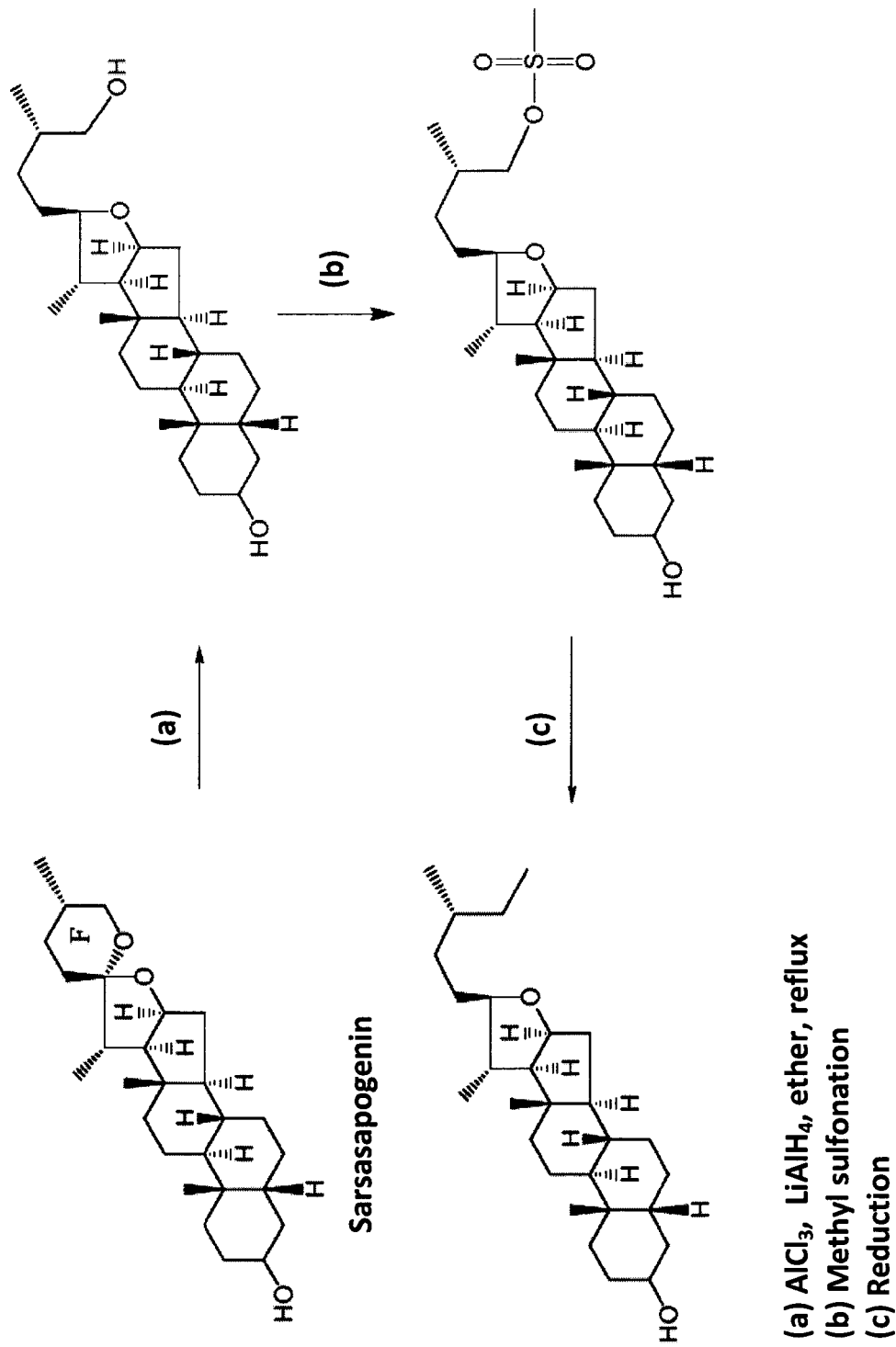
FIG. 12 depicts a synthetic scheme for synthesizing sarsasapogenin with F-ring cleaved.

Thus, several SSG analogs are synthesized as shown in FIG. 12. These analogs are structurally similar to SSG but consisting furostan sapogenin (or dihydrosarsasapogenin) in which the F-ring is cleaved. In addition, Aβ production of two commercially available saponins timosaponin B I (TBI) and timosaponin B II (TBII) are also examined. TBI and TBII as shown below both contain dihydrosarsasapogenin as the aglycone and have disaccharide and monosaccharide sugar chains attached to $C_3$ and $C_{26}$ respectively, representing a group of timosaponins polar than TAIII.

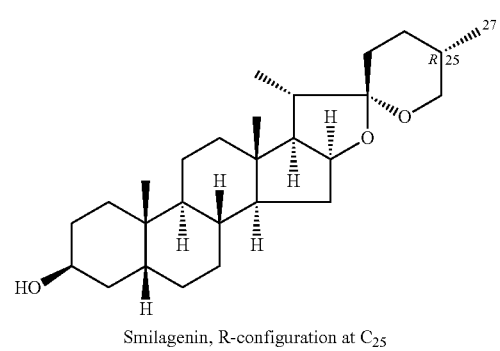

Sarsasapogenin, S-configuration at $C_{25}$

Smilagenin, R-configuration at $C_{25}$ d. The Role of Cis- and Trans-Fused AB Ring

Figure 13:
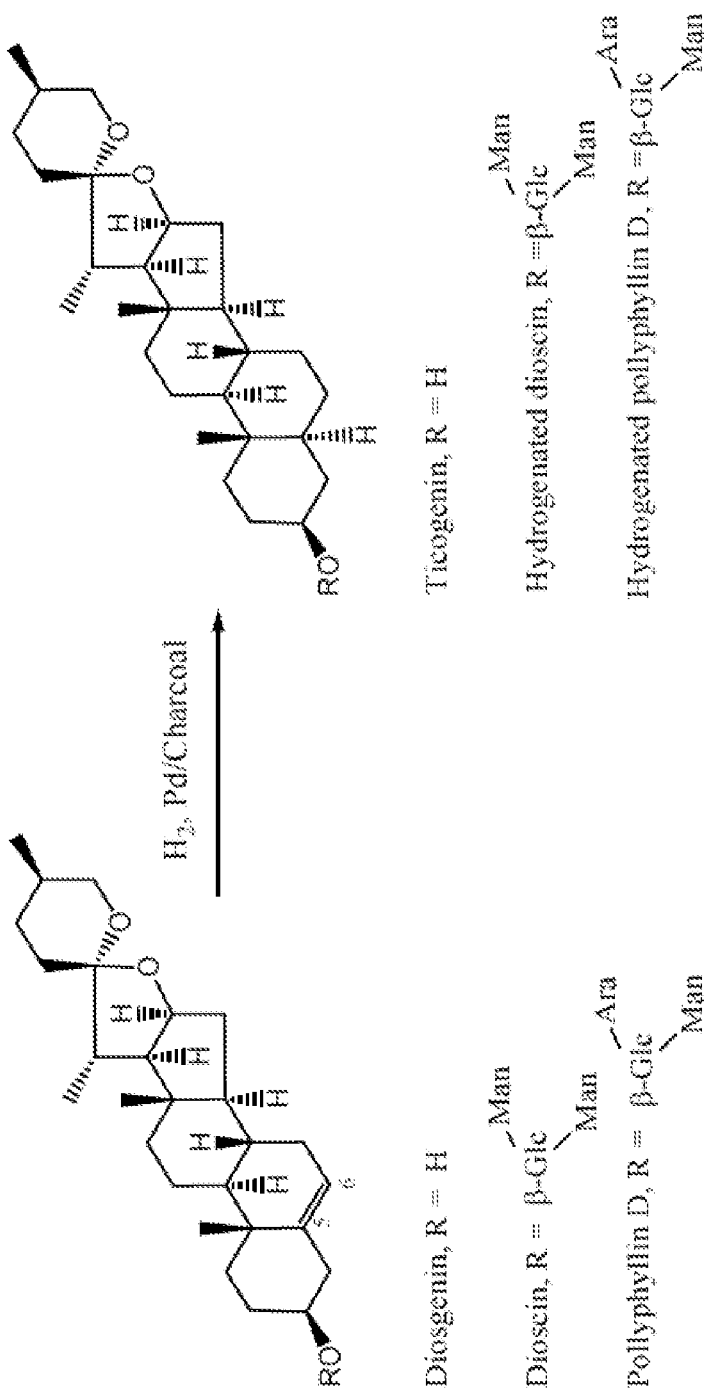
FIG. 13 depicts chemical structures of trans-fused AB ring analogs to SSG.

Other sapogenins and saponins with trans-fused AB ring are studied for studying the pharmacological effect in Aβ generation. Ticogenin structurally resembled to SSG has an AB trans-fused ring and an R-configuration at $C_{25}$ as shown in FIG. 13. However, there are limited commercial sources for Ticogenin. On the other hand, pure Ticogenin can be obtained by simple hydrogenation of Diosgenin as shown in FIG. 13, which bearing a double bond at $C_5$-$C_6$ position.

e. Sarsasapogenin (SSG) Derivatives Having Improved Solubilities

Figure 14:
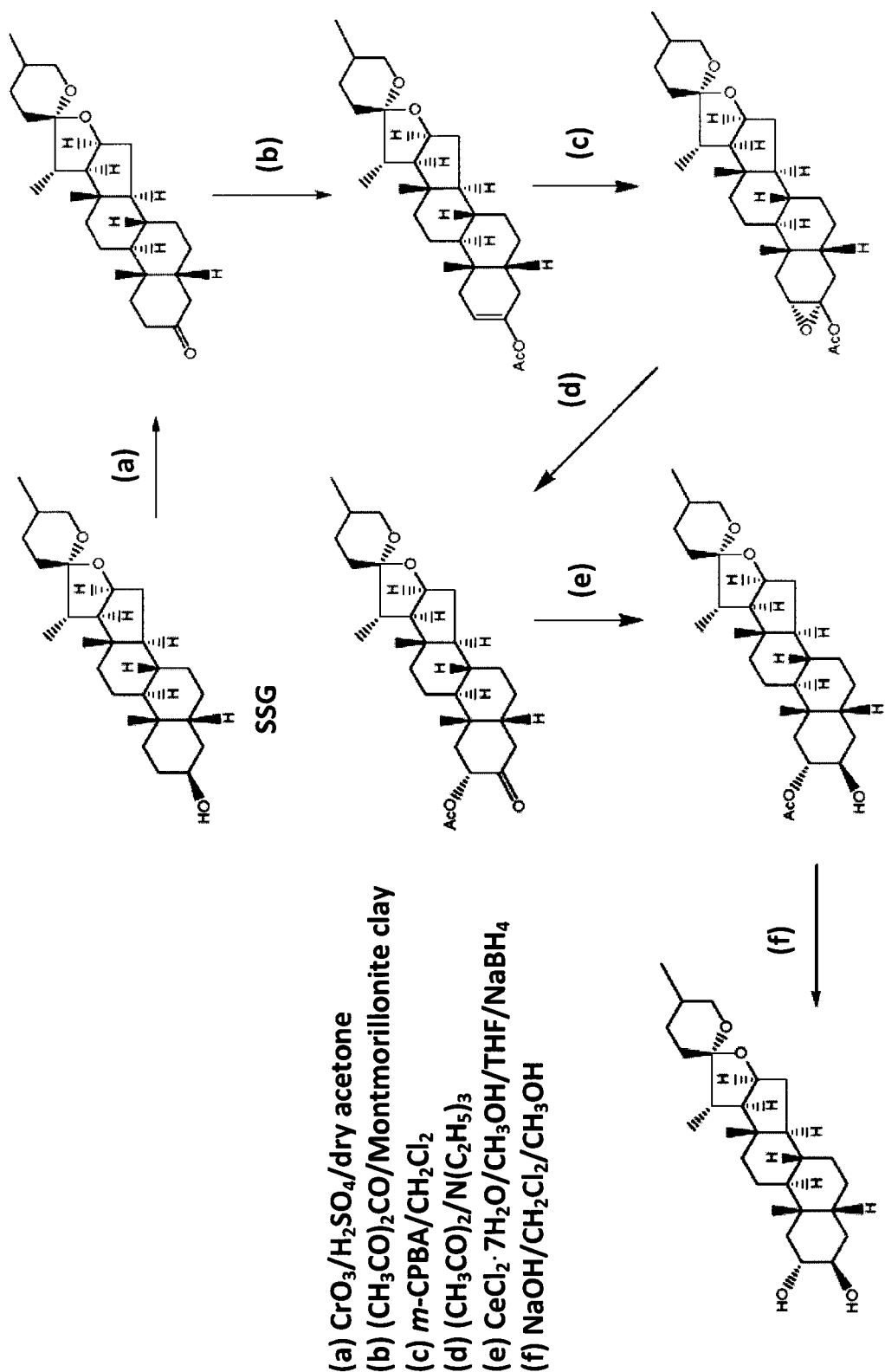
FIG. 14 depicts a synthetic scheme for synthesizing 2-functionalized SSG.

As aforementioned, the sapogenin SSG may be an active substance in inhibiting Aβ production though with high effective dosage as shown in FIG. 11. This is probably due to its strong hydrophobic character and leads to poor solubility in water and buffered cell cultures. The solubility of SSG is improved by introducing polar groups to the molecule as shown in the synthetic scheme FIG. 14. 2-Functionalized SSG derivatives can be used to serve as polar building blocks for the synthesis of timosaponins of improved solubility.

f. Synthesis of TAI Derivatives Having Improved Solubilities

Figure 15:
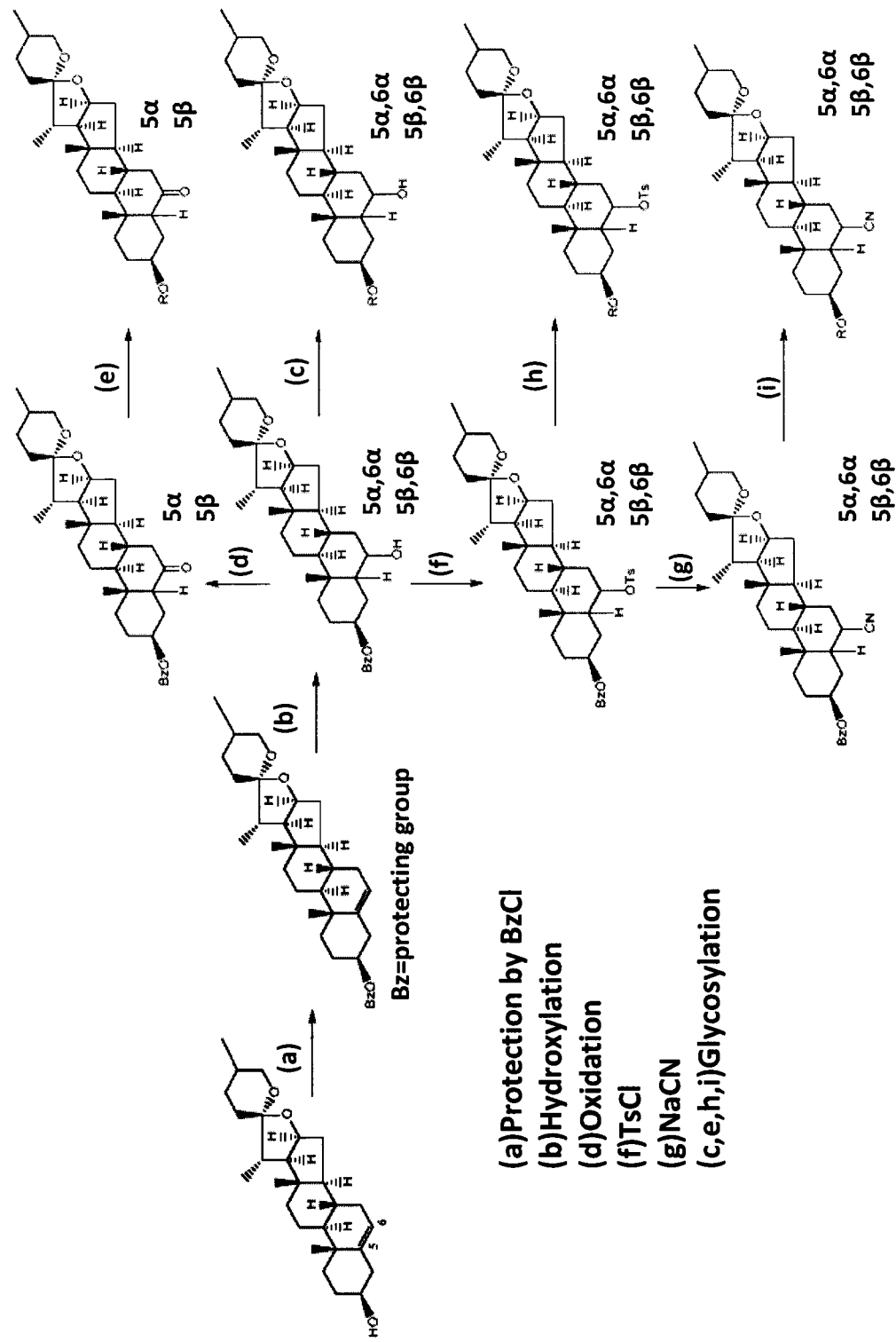
FIG. 15 depicts chemical structures of polar TAI analogs.

Diosgenin possessing double bond can provide a good starting point for various chemical modifications as shown in FIG. 15, for example, hydroxylation at $C_5$-$C_6$ leads to a pair of hydroxylated isomers either 5α-H, 6α-OH or 5β-H, 6β-OH.

g. Synthesis of Monoscaahraide Timosaponins

Figure 16:
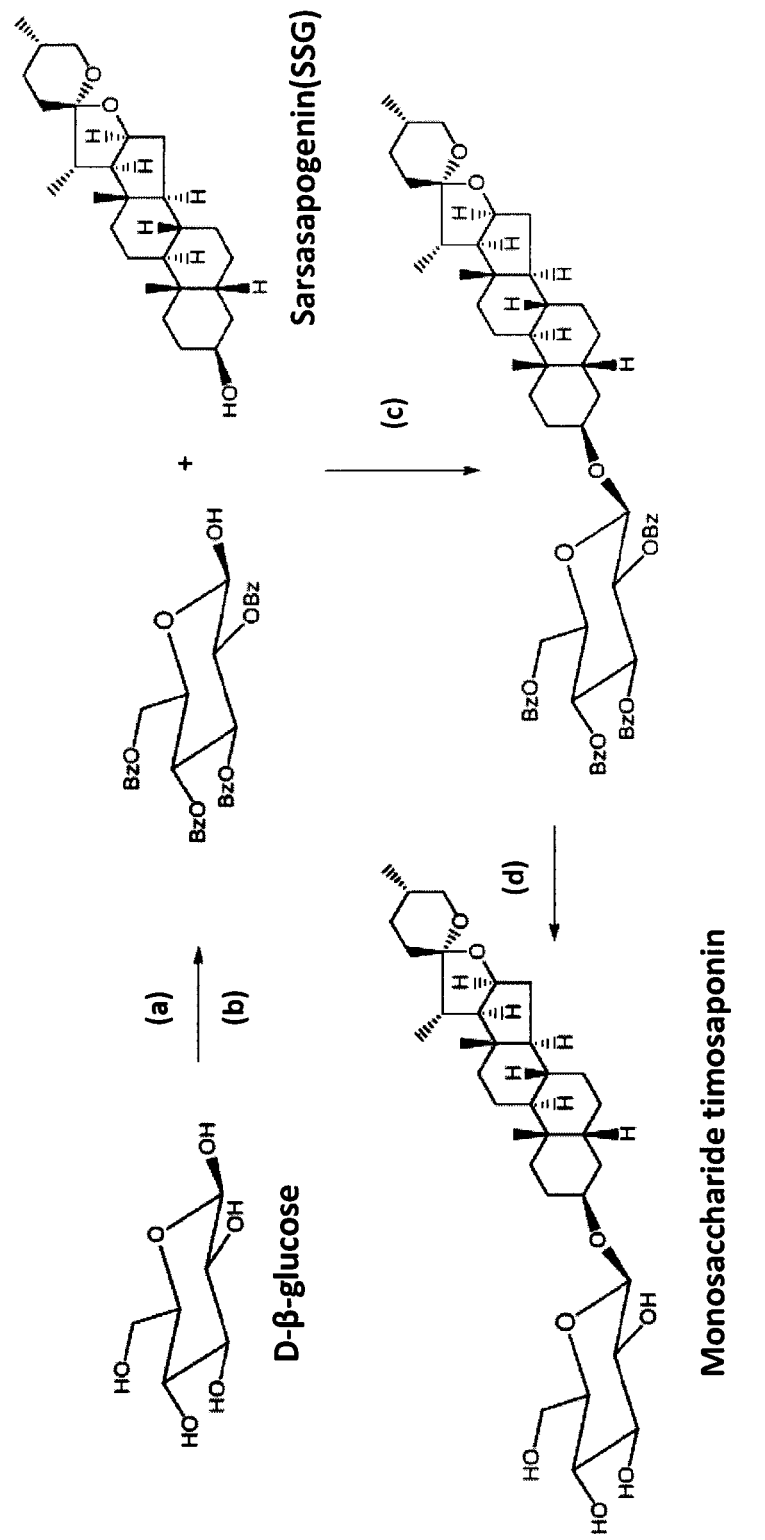
FIG. 16 depicts a synthetic scheme for synthesizing glucoside timosaponin.

FIG. 16 shows a scheme for synthesizing a monoscaahraide timosaponins, i.e., D-β-glucose timosaponin.

h. Synthesis of Trisaccharide Timosaponin

Figure 17:
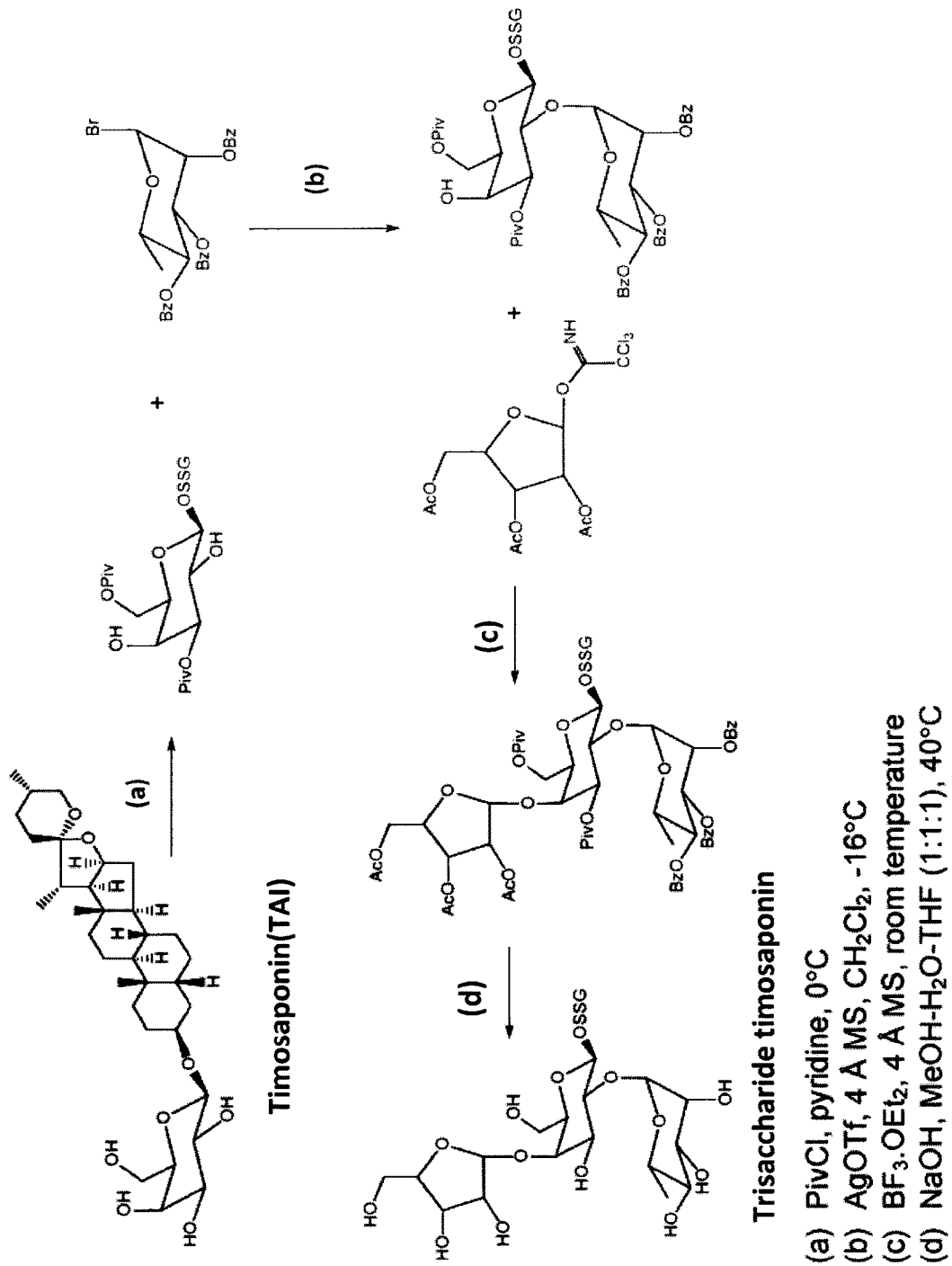
FIG. 17 depicts a synthetic scheme for synthesizing trisaccharide timosaponin.

FIG. 17 shows a scheme for synthesizing a trisaccharide or branched sugar timosaponin from monosaccharide saponin TAI. Similar scheme can be used for synthesizing a trisaccharide or branched sugar timosaponin from disaccharide saponin TAIII.

Example 13

Chemistry

Materials and Methods

Reagents: All reagents were of analytical grade (purity>98%) and were purchased from Sigma-Aldrich Chemical Co. unless otherwise specified. SSG was purchased from Wako Pure Chemical Industries, Ltd. Compounds were dissolved in DMSO as 10 mM stock solutions. Cell culture medium constituents were purchased from Life Technologies, Inc.

Cell culture: Neuro-2A cells expressing Swedish mutants of APP (N2A-APPswe) was cultured in minimal essential medium with 2 mM glutamine, 2 mM pyruvate and 10% fetal bovine serum. Cells were seeded at 6-well plate at $1\times10^6$ cells/mL and grown for two days until confluence. The medium was replaced and the test compounds were added at indicated concentrations for 24 hr. Cell viability was measured by standard MTT assays.

Immunoblot analysis: Cells were washed with phosphate buffered saline and lysed with buffer containing 50 mM Tris-Cl, pH 7.4, 150 mM NaCl, 1% Triton X-100 supplemented with protease inhibitors. Equal amount of proteins (30 μg) was resolved by 16.5% Tris-tricine gels and then transferred to nitrocellulose membrane with 0.2 μm pore size. For detection of secreted Aβ, sAPPα and sAPPβ, cells were treated with the timosaponins for 8 hr in complete medium which were then replaced with medium containing 0.1% FBS. After further incubation of 16 hr, 50 μL of the conditioned medium was mixed with SDS sample buffer and resolved accordingly. The membrane was blocked with Tris-buffered saline containing 0.1% TWEEN® 20 and 3% BSA and then incubated with primary antibodies at 4° C. overnight, followed with appropriate secondary antibodies for 2 hr. The primary antibodies were: APP c-terminal rabbit antibody (1:5000; Merck Bioscience) for detection of full length APP and APP-CTFs, mouse monoclonal 6E10 (Covance) for secreted Aβ and sAPPα, mouse monoclonal 6A1 (IBL) for sAPPβswe, ADAM-10 rabbit antibody (Millipore) and BACE1 rabbit antibody (Millipore). The immunoreactivities were detected using enhanced chemiluminescence reagents (GE Health care). For examination of notch cleavage by γ-secretase, N2A-APPswe cells were transfected with myc-tagged NotchΔE construct (pSC2 EMV-6MT, using Fugene HD (Roche). Cells were then treated with timosaponins for 18 hr and the expression of NotchΔE and NICD were examined by immunoblot analysis using myc-tagged antibodies.

Aβ ELISA: Aβ concentrations in conditioned medium were assayed using ELISA kits for human $A\beta_{40}$, human $A\beta_{42}$ (ultrasensitive) (Invitrogen) and $A\beta_{38}$ (MyBioSource).

β-Secretase assays: Confluent N2A-APPswe cells were harvested and homogenized with 50 mM MES, pH 5.5. Protein extracts (10 μg) were incubated with TAIII for 1 hr at room temperature. The β-secretase activities were assayed by adding 10 μM fluorogenic β-secretase substrate (Millipore) to the reaction mixtures and fluorescence signals (excitation, 380 nm; emission, 460 nm) were measured. β-Secretase assays were also performed using purified BACE1 (Millipore) at 100 ng in a buffer of 50 mM MES, pH 5.5.

Immunofluorescence examination of neurite outgrowth: Neuro-2A cells were seeded at $1\times10^5$ cells per glass bottom dish. After treatment, cells were fixed with 4% paraformaldyde for 10 min, permeabilized with 0.1% Trition X-100, and then blocked with 1% BSA in PBS. The cells were incubated with monoclonal antibody raised against type III β-tubulin (Sigma) for 1 hr followed by Alexa488 conjugated secondary antibody. Neurite morphology was examined under fluorescence microscope.

Chemical Synthesis

NMR spectra for the following examples were recorded on a Bruker AV 400, DRX 500 or AV 600 spectrometers. Each final product was recorded for 1-dimensional ($^1$H NMR, $^{13}$C NMR and Dept-135) and 2-dimensional ($^1$H-$^1$H COSY, $^1$H-$^1$H NOESY, $^1$H-$^{13}$C HSQC and $^1$H-$^{13}$C HMBC) NMR spectra. Samples were dissolved in $CDCl_3$, $CD_3OD$ or $C_5D_5N$ and chemical shifts were expressed in ppm relative to TMS as an internal standard reference at ambient temperature except specified. Mass spectra were obtained in EI or FAB mode using Thermo Scientific DFS High Resolution Magnetic Sector spectrometer. ESI mass spectra were measured on a Thermo Scientific LCQ classic spectrometer.

Example 14

Chemistry

Synthesis of Timosaponin A I (TAI)

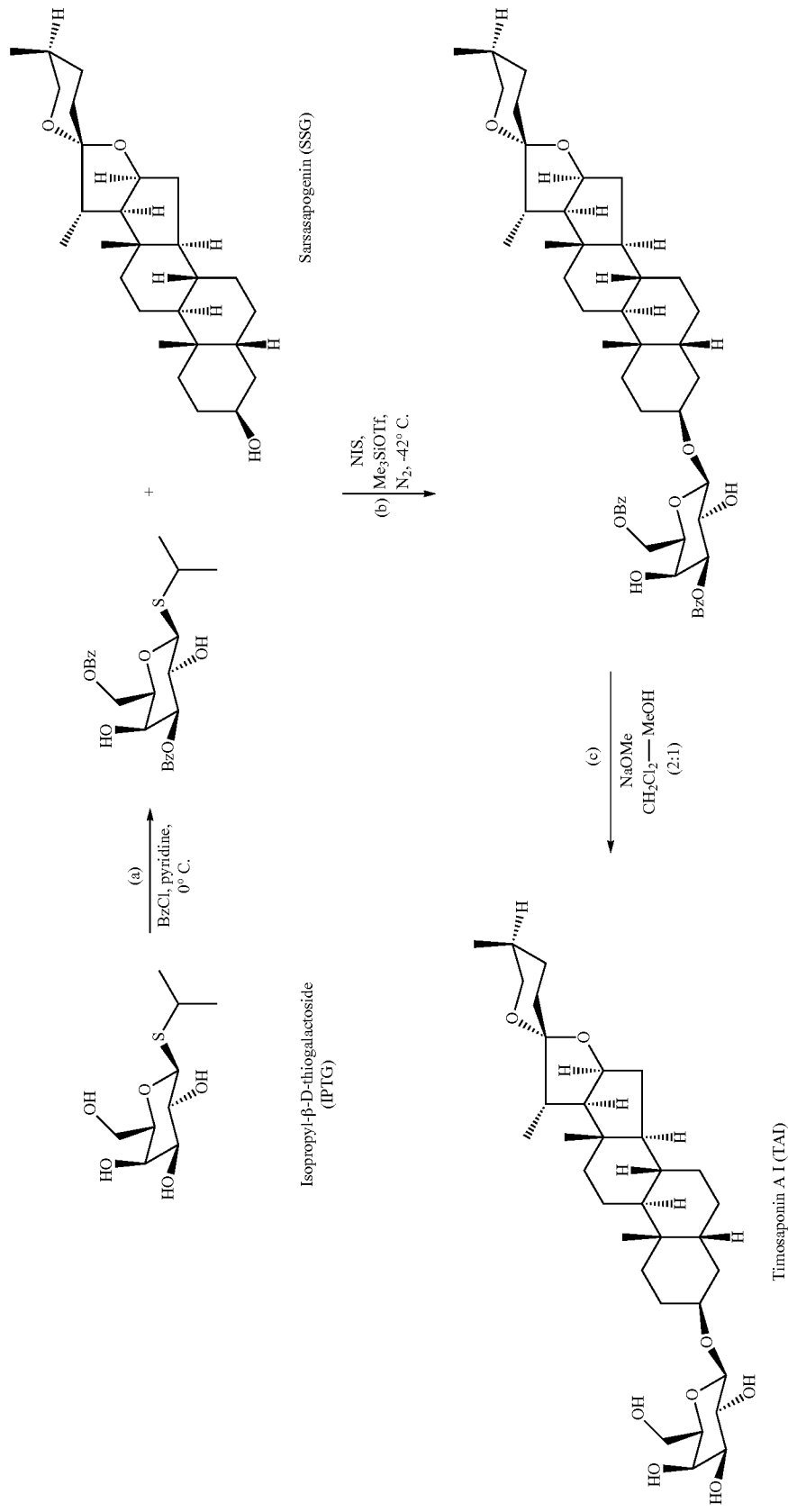
FIG. 1 Synthesis of Timosaponin A I (TAI)

Step (a)

To a solution of isopropyl-β-D-thiogalactopyranoside (IPTG, 1.015 g, 4.2 mmol) dissolved in anhydrous pyridine (7 mL) was slowly added benzoyl chloride (0.982 mL, 8.5 mmol) to form a reaction mixture. The reaction mixture was stirred at 0° C. until all the IPTG was consumed. The reaction progress was monitored by TLC. The reaction mixture was diluted with $CH_2Cl_2$ and then washed sequentially with dilute HCl, saturated $NaHCO_3$ and brine. The organic layer was dried over anhydrous $Na_2SO_4$ and concentrated by vacuum. The crude product was subjected to column chromatography using $CH_2Cl_2$:EtOAc (25:1) as eluent to obtain isopropyl 3,6-di-O-benzoyl-1-thio-β-D-galactopyranoside (0.98 g, yield 52%.)

Step (b)

To a mixture of isopropyl 3,6-di-O-benzoyl-1-thio-β-D-galactopyranoside (368 mg, 0.824 mmol) and sarsasapogenin (286 mg, 0.687 mmol) in anhydrous $CH_2Cl_2$ (10 mL), NIS (277 mg, 1.237 mmol) and i-$Pr_3$SiOTf (22.2 μL, 0.082 mmol) were added under $N_2$ atmosphere at −42° C. The mixture was stirred at this condition for 1 hr, then neutralized with TEA and concentrated. The crude product was subjected to column chromatography using $CH_2Cl_2$:MeOH (50:1) as eluent to obtain 3,6-dibenzyolated Timosaponin A I (265 mg, yield 49%).

Step (c)

To a stirred solution of 3,6-dibenzyolated timosaponin A I (100 mg, 0.127 mmol) in anhydrous $CH_2Cl_2$:MeOH (2:1, 21 mL) was added dropwise with NaOMe in MeOH (0.1 mL, 1.0 M) at room temperature to form a reaction mixture. After stirring for 3.5 hr, TLC ($CH_2Cl_2$:MeOH=9:1) indicated that all starting materials had been consumed. The reaction mixture was neutralized with Amberlite IR 120 ($H^+$), filtered and concentrated. The crude product was subjected to column chromatography using $CH_2Cl_2$:MeOH (9:1) to obtain Timosaponin A I (66 mg, yield 90%).

Example 15

Chemistry

Syntheses of Timosaponin A V and Timosaponin A III.

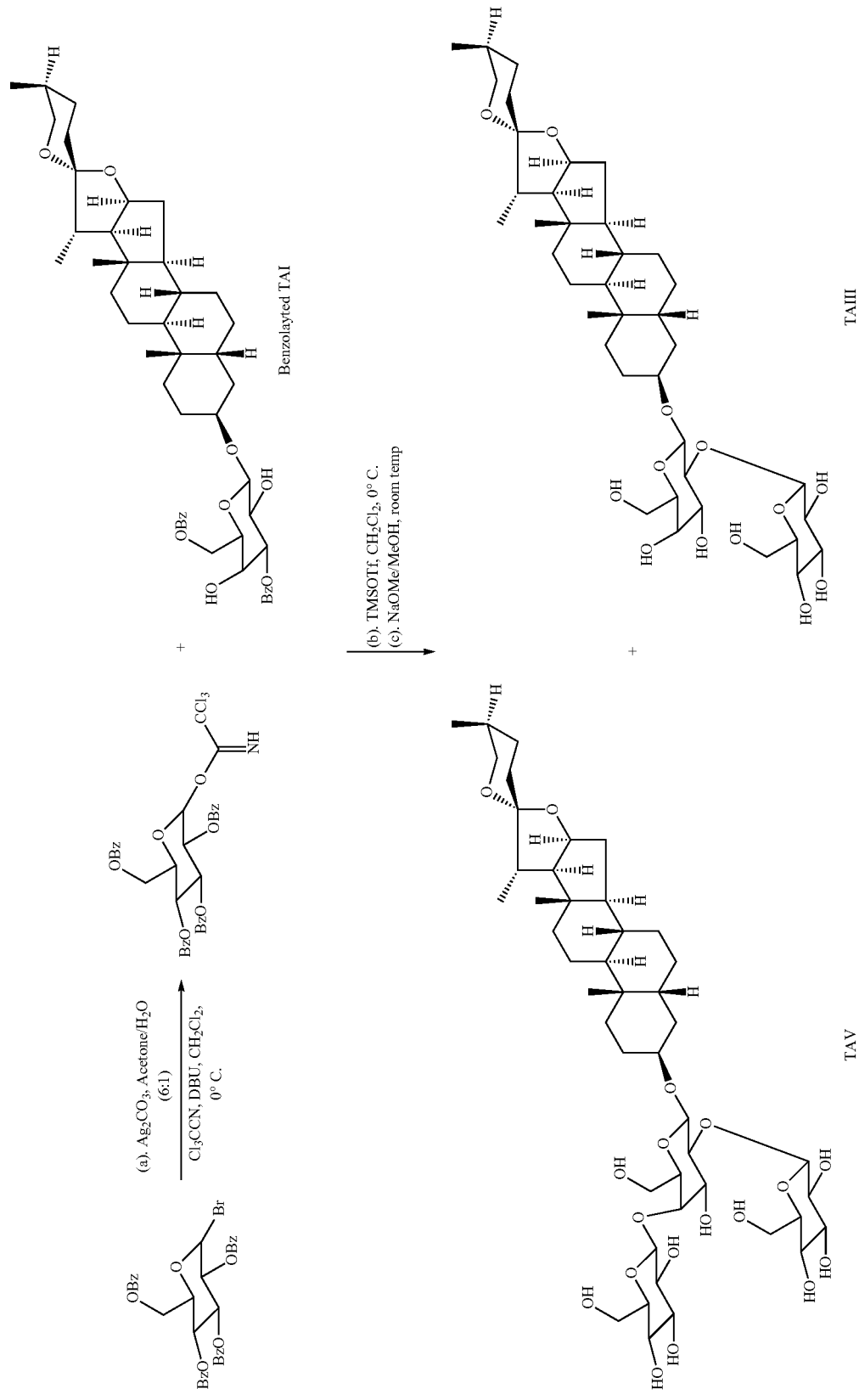
FIG. 2 Syntheses of Timosaponin A V (TAV) and Timosaponin A III (TAIII).

Step (a)

To a solution of the crude 2,3,4,6-tetra-O-benzoyl-α-D-glucopyranosyl bromide (1.0 g, 1.52 mmol) in acetone/H$_2$O (6:1, 7 mL) was added Ag$_2$CO$_3$ (1.3 g, 4.72 mmol) to form a mixture. The mixture was stirred at room temperature for 4 hr. The mixture was then filtered through CELITE® and the filtrate was concentrated. A solution of the resulting hemiacetal and Cl$_3$CCN (1.05 mL, 10.5 mmol) in anhydrous CH$_2$Cl$_2$ (5 mL) at 0° C. was added with 1,8-diazabicyclo[5.4.0]undec-7-ene (DBU) (0.27 mL, 1.8 mmol) under N$_2$ and stirred at 0° C. for 3 hr. The mixture was concentrated and subjected to column chromatography using n-hexane:EtOAc:CH$_2$Cl$_2$ (10:1:2) as eluent to afford 2,3,4,6-tetra-O-benzoyl-α-D-glucopyranosyl trichloroacetimidate (828 mg, yield 75%).

Step (b)

To a mixture of sarsasapogenin 3,6-di-O-benzoyl-β-D-glucopyranose (benzolayted TAI, 65.7 mg, 0.083 mmol), 2,3,4,6-tetra-O-benzoyl-α-D-glucopyranosyl trichloroacetimidate (160 mg, 0.184 mmol) and powdered 4 Å molecular sieves (100 mg) in anhydrous CH$_2$Cl$_2$ (10 mL) at 0° C. under N$_2$ was added TMSOTf (4.5 μA, 0.026 mmol). After stirring at 0° C. for 2 hr, the reaction was quenched with TEA. The reaction mixture was filtered through CELITE®. The filtrate was concentrated and subjected to column chromatography using n-hexane:EtOAc (2:1) as eluent to give the crude O-benzoylated product.

Step (c)

To a solution of crude O-benzoylated product dissolved in anhydrous CH$_2$Cl$_2$:MeOH (2:1, 18 mL) was added NaOMe in MeOH (0.2 mL, 1.0 M). After stirring at room temperature for 2 hr, TLC monitoring (CH$_2$Cl$_2$:MeOH=4:1) indicated consumption of all starting materials. The reaction mixture was neutralized with Amberlite IR 120 (H$^+$), filtered and concentrated. The crude sample was purified by column chromatography using CH$_2$Cl$_2$:MeOH (4:1) as eluent to obtain timosaponin A V (23 mg, yield 31%) and TAIII (31 mg, yield 60%).

Example 16

Chemistry

Synthesis of Asparagoside A

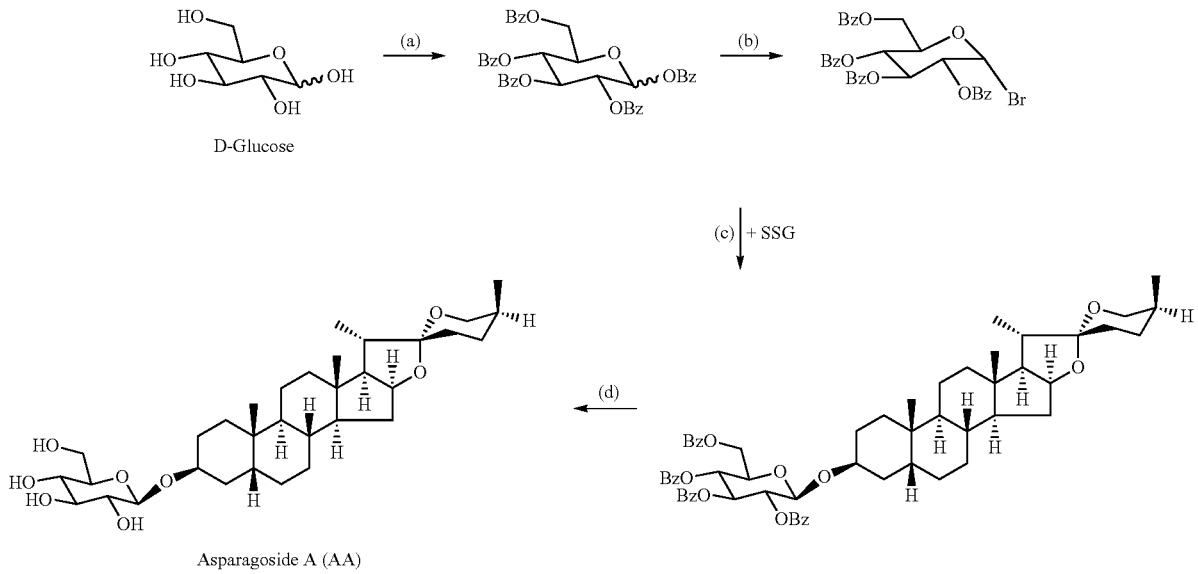

FIG. 3 Sythesis of Asparagoside A (AA).

Step (a)

To a solution of D-glucose (1.8 g, 10.0 mmol) in pyridine (10 mL) was added benzoyl chloride (6.2 mL, 53 mmol) and DMAP (~5 mg) as a catalyst. After stirring overnight at room temperature, the reaction mixture was quenched with H$_2$O (30 mL), extracted with CH$_2$Cl$_2$, dried with anhydrous Na$_2$SO$_4$, filtered and concentrated. The crude product was subjected to column chromatography using n-hexane:EtOAc (2:1) as eluent to obtain the mixed products of 1α,2,3,4,6-penta-O-benzoyl-D-glucopyranose and 1β,2,3,4,6-penta-O-benzoyl-D-glucopyranose (7.0 g, yield 85%).

Step (b)

To a solution of 1,2,3,4,6-penta-O-benzoyl-D-glucopyranose (2.5 g, 3.57 mmol) in anhydrous CH$_2$Cl$_2$ at 0° C. was added HBr solution in AcOH (33%, 10 mL) and stirred for 1 hr. The temperature was then increased to room temperature and stirred for another hour. The solvent was removed under vacuum and the residue was dissolved in CH$_2$Cl$_2$ (100 mL) and neutralized with saturated aqueous NaHCO$_3$ (50 mL). The organic layer was separated and washed with H$_2$O (3×50 mL), saturated aqueous NaHCO$_3$ (3×30 mL) and brine (2×30 mL). Then the solution was dried with anhydrous Na$_2$SO$_4$, filtered and concentrated in vacuum to afford 2,3,4,6-tetra-O-benzoyl-α-D-glucopyranosyl bromide quantitatively as a white foamy solid.

Step (c)

To a mixture of sarsasapogenin (208 mg, 0.499 mmol), 2,3,4,6-tetra-O-benzoyl-α-D-glucopyranosyl bromide (311 mg, 0.472 mmol) and powdered 4 Å molecular sieves (600 mg, 0.472 mmol) in anhydrous $CH_2Cl_2$ (10 mL) at −42° C. under $N_2$ was added AgOTf (130 mg, 0.5 mmol) in dry toluene (2 mL). The reaction mixture was stirred at −42° C. for 3 hr and then stirred at room temperature overnight. The mixture was diluted with $CH_2Cl_2$ (10 mL) followed by filtration through CELITE®. The filtrate was then concentrated. The crude product was subjected to column chromatography using n-hexane:EtOAc:$CH_2Cl_2$ (10:1:2) as eluent to give the benzyolated asparagoside A (169 mg, yield 36%).

Step (d)

Benzyolated Asparagoside A (290 mg, 0.291 mmol) was dissolved in anhydrous $CH_2Cl_2$:MeOH (2:1, 10.5 mL) followed by dropwise addition of NaOMe in MeOH (0.15 mL, 1.0 M) at room temperature. After stirring for 2 hr, TLC ($CH_2Cl_2$:MeOH=9:1) indicated complete consumption of all starting material. The reaction mixture was neutralized with Amberlite IR 120 ($H^+$), filtered and concentrated. The crude product was subjected to column chromatography using $CH_2Cl_2$:MeOH (10:1) as eluent to obtain asparagoside A (160 mg, yield 95%).

Example 17

Chemistry

Synthesis of Dihydrosarsasapogenin

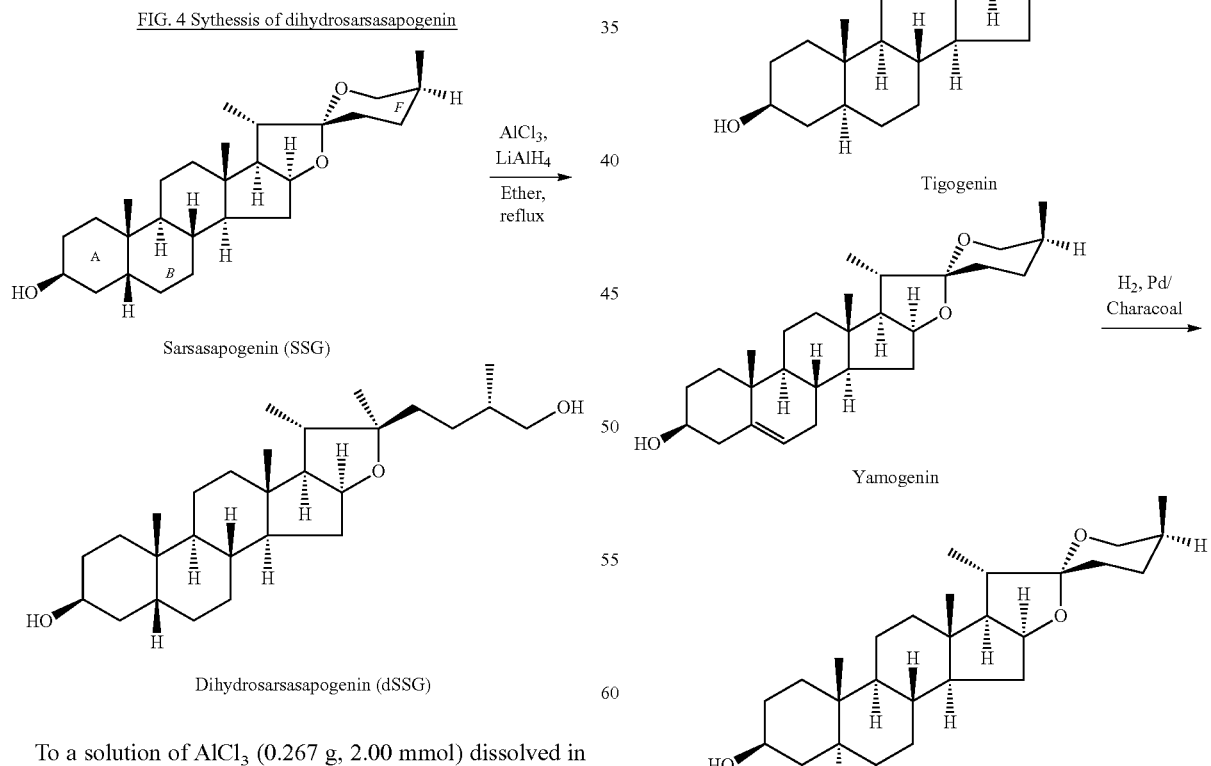

FIG. 4 Sythessis of dihydrosarsasapogenin

To a solution of $AlCl_3$ (0.267 g, 2.00 mmol) dissolved in anhydrous $Et_2O$ (3 mL) at 0° C. was added ethereal $LiAlH_4$ solution (0.5 mL, 1.0 M) and the solution was stirred for 0.5 hr. Sarsasapogenin (417 mg, 1.0 mmol) was then added. After the ice bath was removed, the solution was stirred overnight at room temperature. The reaction was quenched by addition of $H_2SO_4$ (10%, 20 mL). The clear ether layer was separated and aqueous layer was extracted with $Et_2O$ thrice. The organic layers were combined, dried with anhydrous $Na_2SO_4$, filtered and concentrated to afford a crude product which was then subjected to column chromatography using MeOH:$CH_2Cl_2$ (1:30) as eluent to afford dihydrosarsasapogenin (160 mg, yield 38%).

Example 18

Chemistry

Syntheses of Tigogenin and Neotigogenin

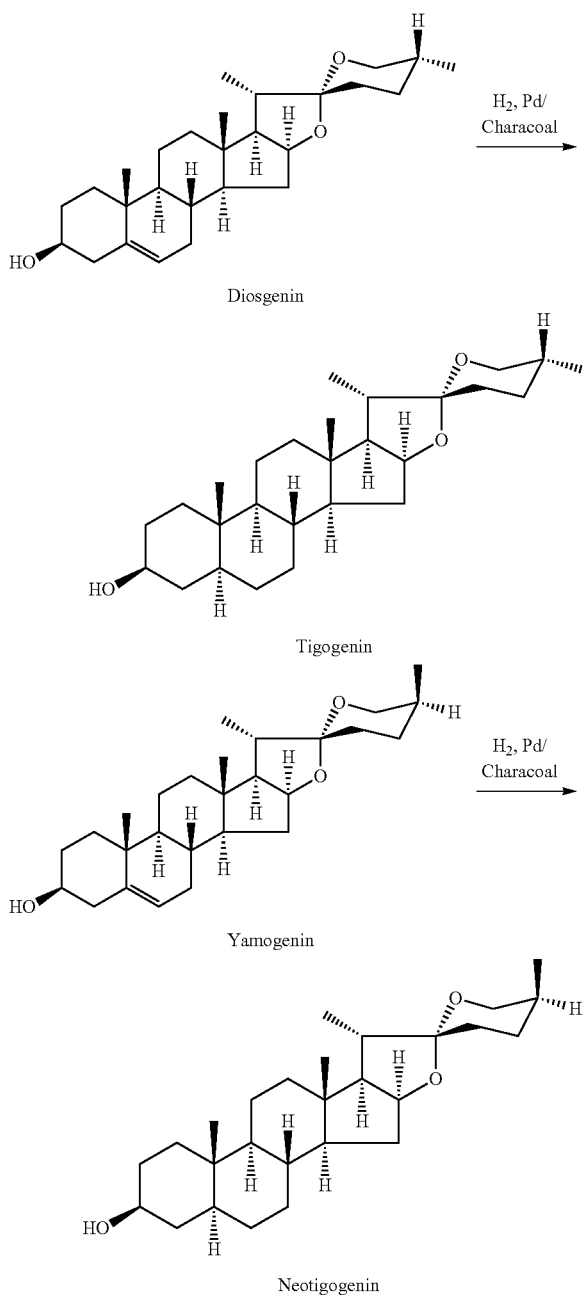

FIG. 5 Syntheses of Tigogenin and Neotigogenin.

To a solution of diosgenin (10 mg, 0.024 mmol) dissolved in MeOH (15 mL) was added Pd/charcoal (5%, 3 mg) as a catalyst. $H_2$ was bubbled in and stirred at room temperature for 3 hr. Filtered and dried to obtain tigogenin.

To a solution of yamogenin (5 mg, 0.012 mmol) dissolved in MeOH (7.5 mL) was added Pd/charcoal (5%, 1.5 mg) as a catalyst. $H_2$ was bubbled into the solution for 5 hr under stirring at room temperature. The solution was then filtered and dried to obtain neotigogenin.

Example 19

Chemistry

Syntheses of Sarsasapogenone and Episarsasapogenin

FIG. 6 Syntheses of Sarsasapogenone and Episarsasapogenin.

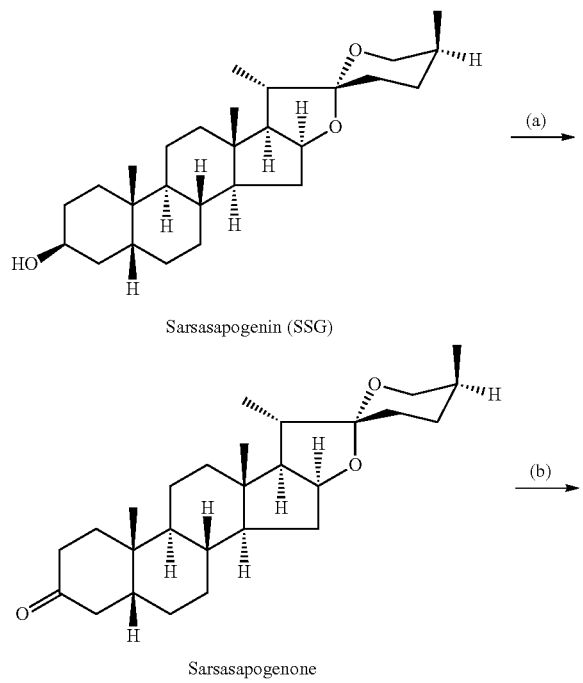

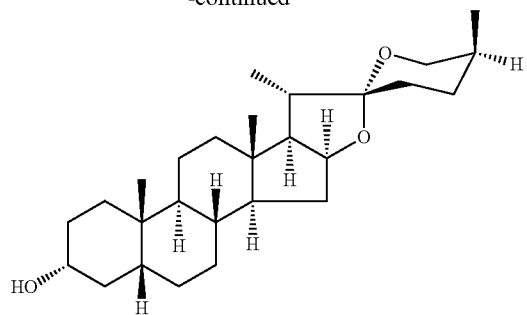

Episarsasapogenin

Step (a)

To a solution of sarsasapogenin (500 mg, 1.20 mmol) in acetone (25 mL) at 30° C. was added 8N chromic acid in $H_2SO_4$ (40%, 1.5 mL) with stirring for 30 min. The completion of the reaction was monitored by TLC (n-hexane: EtOAc=3:1). After completion, the solution was dried to afford a crude product. After water was added, the solution was extracted with $CH_2Cl_2$. The dry crude product was subjected to column chromatography using n-hexane: EtOAc (5:1) as eluent to give sarsasapogenone as a white solid (251 mg, yield 50%).

Step (b)

To a solution of sarsasapogenone (50 mg, 0.12 mmol) in THF (1.5 mL) at room temperature was slowly added lithium tri-tert-butoxyaluminohydride (0.16 mL, 1M in THF) at such a rate that the temperature was maintained. After the addition was complete, the mixture was stirred at room temperature overnight. When TLC ($CH_2Cl_2$: EtOAc=10:1) indicated complete consumption of sarsasapogenone, saturated $NH_4Cl$ solution was added to quench the reducing reagent. The mixture was filtered and the solid was washed with $CH_2Cl_2$. The combined filtrates were extracted with $CH_2Cl_2$ and the organic layer was evaporated to afford a crude product which was subjected to column chromatography using $CH_2Cl_2$:EtOAc (10:1) as eluent yielding episarsasapogenin (80 mg, yield 80%) was obtained as white solid.

Example 20

Chemistry

Synthesis of Capsicoside $A_3$

FIG. 7 Synthesis of Capsicoside A3

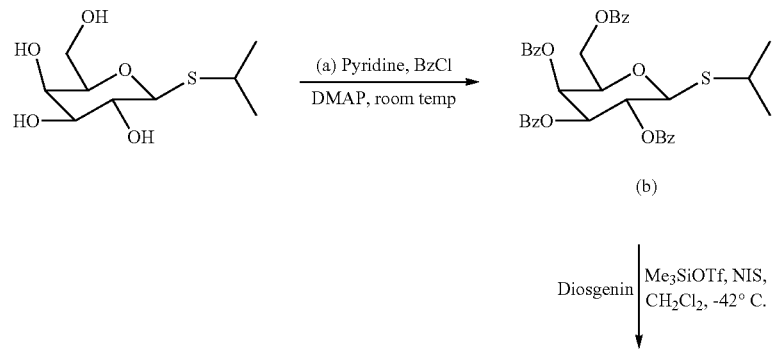

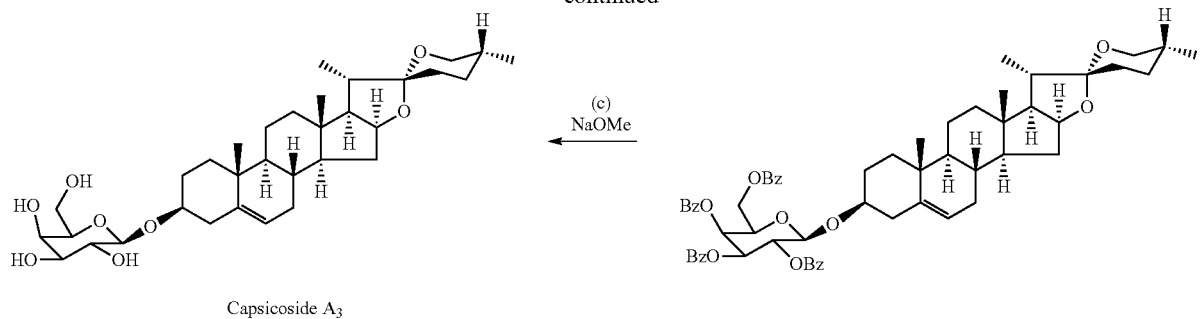

Capsicoside A₃

Step (a)

To a solution of isopropyl β-D-1-thiogalactopyranoside (IPTG, 1.019 g, 4.3 mmol) and 4-dimethylaminopyridine (DMAP, 3 mg) as a catalyst in anhydrous pyridine (7 mL) was added slowly benzoyl chloride (3.0 mL, 17.6 mmol). A white precipitate was observed. The mixture was stirred at room temperature until complete consumption of IPTG. The consumption of IPTG was monitored by TLC. The solution was diluted with $CH_2Cl_2$, and then washed with dilute HCl solution, saturated $NaHCO_3$ solution and brine sequentially. The organic layer was dried over anhydrous $Na_2SO_4$ and evaporated to dryness. The crude product was then subjected to column chromatography using n-hexane:$CH_2Cl_2$ (25:1) as eluent to obtain isopropyl 2,3,4,6-tetra-O-benzoyl-1-thio-β-D-galactopyranoside (2.377 g, yield 85%) as white solid.

Step (b)

To a mixture of isopropyl 2,3,4,6-tetra-O-benzoyl-1-thio-β-D-galactopyranoside (327 mg, 0.50 mmol) and Diosgenin (207 mg, 0.50 mmol) in anhydrous $CH_2Cl_2$ (10 mL) was added NIS (123 mg, 0.55 mmol) and $Me_3SiOTf$ (8.8 μL, 0.005 mmol) under $N_2$ at −42° C. The mixture was stirred under these conditions for 2 hr, then neutralized with TEA and concentrated. The crude product was subjected to column chromatography using n-hexane:$CH_2Cl_2$:EtOAc (40:40:3) as eluent to obtain diosgenin isopropyl 2,3,4,6-tetra-O-benzoyl-1-thio-β-D-galactopyranoside (135 mg, yield 28%) as white solid.

Step (c)

To a solution of diosgenin isopropyl 2,3,4,6-tetra-O-benzoyl-1-thio-β-D-galactopyranoside (85 mg, 0.086 mmol) in anhydrous $CH_2Cl_2$-MeOH (2:1, 7.5 mL) was added dropwise NaOMe in MeOH (0.1 mL, 1.0 M) at room temperature to form a mixture. The mixture was stirred at room temperature for 3.5 hr. After TLC ($CH_2Cl_2$:MeOH=9:1) result indicated that all starting material was consumed, the mixture was then neutralized with Amberlite IR 120 ($H^+$), filtered and concentrated. The product was subjected to column chromatography using $CH_2Cl_2$:MeOH (10:1) as eluent to obtain capsicoside $A_3$ (46 mg, yield 93%) as white solid.

Example 21

Chemistry

Syntheses of 5β-H, 6β-OH and 5α-H, 6α-OH of Yamogenin and Diosgenin.

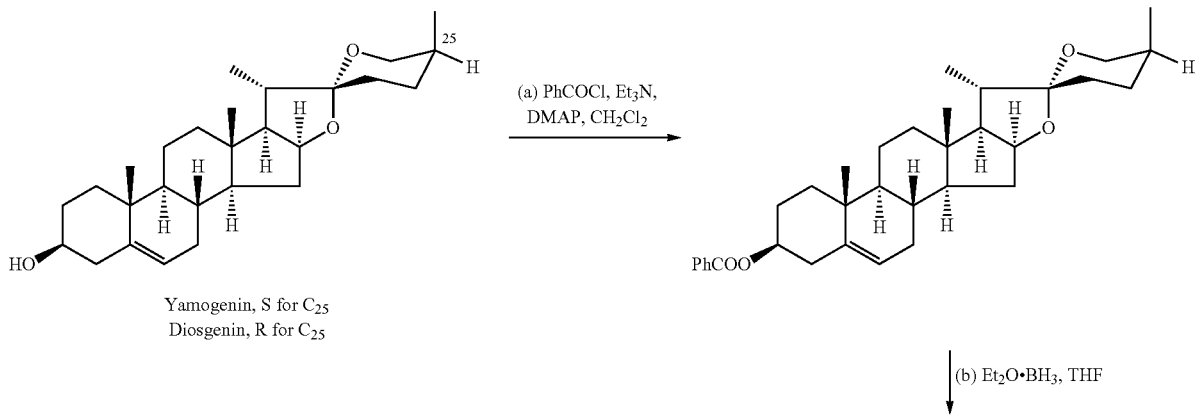

FIG. 8 Syntheses of 5a-H, 6a-OH and 5b-H, 6b-OH of Yamogenin.

-continued

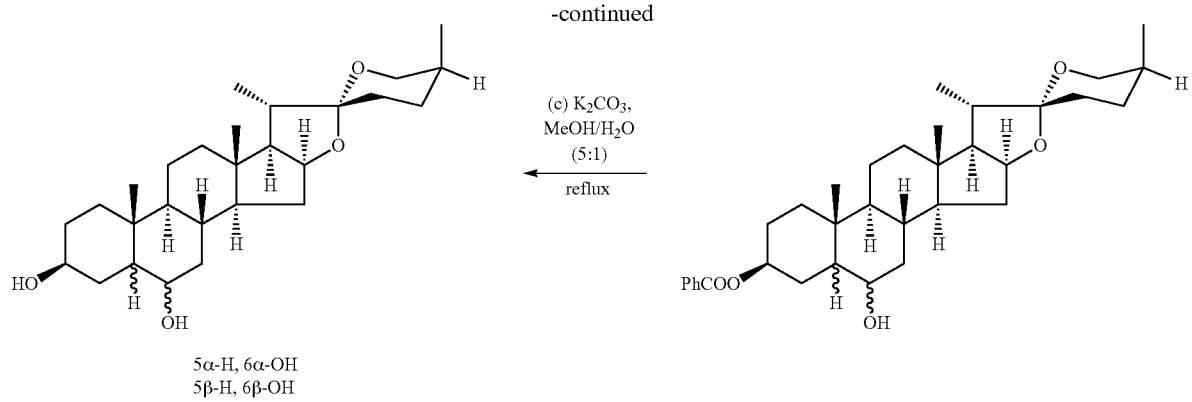

5α-H, 6α-OH
5β-H, 6β-OH

Step (a)

To a solution of yamogenin (21 mg, 0.01 mmol) in anhydrous CH$_2$Cl$_2$ (5 mL) at 0° C. were added benzoyl chloride (21 mg), Et$_3$N (25 mg) and DMAP (2.5 mg) subsequently. The solution was warmed to room temperature and monitored by TLC (~8 hr). The solution was concentrated under reduced pressure and the residue was subjected to column chromatography using EtOAc/n-Hexane as eluent to obtain 3-benyolated yamogenin (Yield: 83%).

Step (b)

To a solution of 3-benyolated yamogenin (52 mg, 0.1 mmol) in anhydrous THF (5 mL) at 0° C. was added Et$_2$O.BH$_3$ (0.15 mmol). The solution was warmed to room temperature and monitored by TLC (~12 hr). Na$_2$CO$_3$ (200 mg), H$_2$O (2 mL) and H$_2$O$_2$ (200 µL) were added slowly to the mixture and stirred for 1 hr. Then, the solution was extracted with CH$_2$Cl$_2$ (3×20 mL) and the organic fraction was dried over MgSO$_4$ and concentrated under reduced pressure. The residue was subjected to column chromatography using EtOAc/n-Hexane as eluent to obtain 3-benzyolated 5β-H, 6β-OH yamogenin (Yield: 27%) and 3-benzyolated 5α-H, 6α-OH yamogenin (Yield: 47%).

Step (c)

To a solution of 3-benzyolated 5β-H, 6β-OH yamogenin (27 mg, 0.05 mmol) in MeOH—H$_2$O (5:1, 6 mL) was added K$_2$CO$_3$ (30 mg). The reaction mixture was heated under reflux and monitored by TLC (~5 hr). The mixture was extracted with CH$_2$Cl$_2$ (3×20 mL). The organic fraction was then dried over MgSO$_4$ and concentrated under reduced pressure. The residue was purified by column chromatography using EtOAc/n-Hexane as eluent to obtain 5β-H, 6β-OH yamogenin (Yield: 83%).

Similarly, 5α-H, 6α-OH and 5β-H, 6β-OH of diosgenin were prepared.

Example 22

Chemistry

Synthesis of Ethereal Sarsasapogenin

FIG. 9 Synthesis of Ethereal Sarsasapogenin.

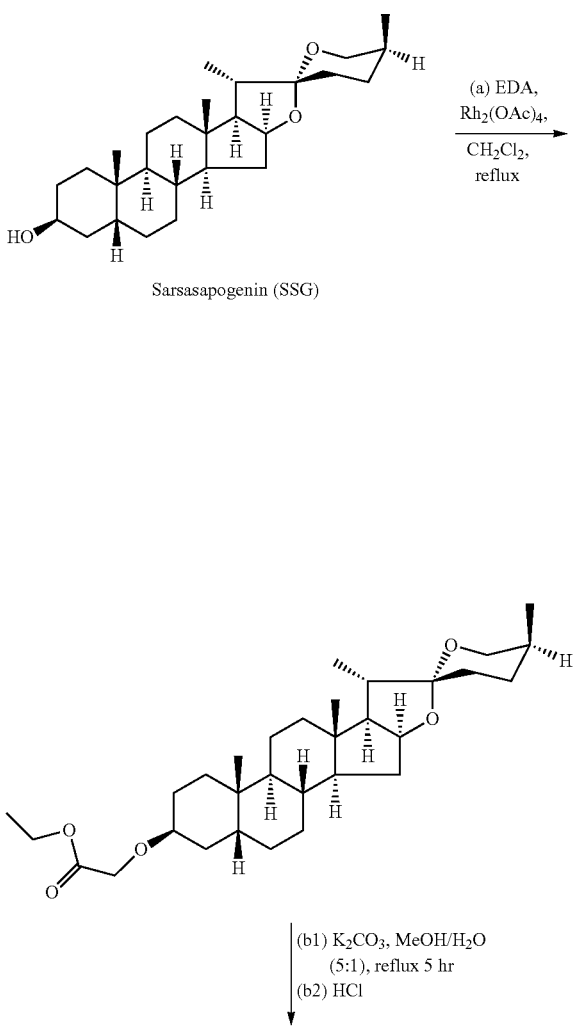

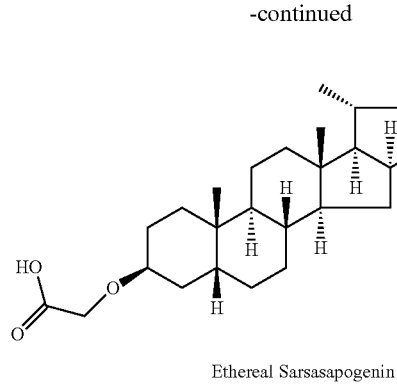

Ethereal Sarsasapogenin

To a solution of sarsasapogenin (42 mg, 0.1 mmol) and $Rh_2(OAc)_4$ (1 mg) in anhydrous $CH_2Cl_2$ (2 mL) was added with a solution of EDA (35 mg) in $CH_2Cl_2$ (2 mL) through a syringe pump over 1 hr to form a reaction mixture. The reaction mixture was then concentrated and the resulting residue was dissolved in MeOH—$H_2O$ (5:1, 6 mL) followed by addition of $K_2CO_3$ (300 mg). The reaction mixture was heated under reflux for about 5 hr and monitored by TLC. The pH of the reaction mixture was adjusted to pH 2 with dilute HCl. The reaction mixture was extracted with $CH_2Cl_2$ (3×20 mL). The organic fraction was dried over $MgSO_4$ and concentrated under reduced pressure. The residue was subjected to column chromatography using EtOAc/Hexane as eluent to obtain ethereal SSG (Yield: 80%).

TABLE 4

$IC_{50}$ (mean ± S.D, n ≥ 3) of timosaponins and SSG epimers in lowering Aβ42 production in N2A-APPswe cells, as measured using methods specified in Example 5

| Compound | $IC_{50}$ (μM) |
|---|---|
| Formula I | |
| Timosaponin AIII (TAIII) | 2.3 ± 0.2 |
| Timosaponin AI (TAI) | 6.1 ± 2.8 |
| Timosaponin AV (TAV) | 4.2 ± 1.2 |
| Asparagoside A (AA) | 6.0 ± 1.4 |
| Sarsasapogenin (SSG) | 53 ± 9 |
| Ergosterol | >100 |
| Smilagenin | >100 |
| Yamogenin | >100 |
| Neotigogenin | >100 |
| Tigogenin | >100 |
| Sarsasapogenone | 50 ± 5 |
| Episarsasapogenin | >100 |
| Diosgenin | >100 |
| Capsicoside $A_3$ | >100 |
| Ethereal SSG | 27 ± 8 |
| 5β-H, 6β-OH diosgenin | >100 |
| 5α-H, 6α-OH diosgenin | >100 |
| 5β-H, 6β-OH yamogenin | 45 ± 4 |
| 5α-H, 6α-OH yamogenin | >100 |
| Formula II | |
| Timosaponin BI (TBI) | >100 |
| Timosaponin BII (TBII) | >100 |
| Formula III | |
| Dihydrosarsasapogenin | >100 |

TABLE 5

$IC_{50}$ (mean ± S.D., n = 3) of steroidal saponins against growth of cancer cell lines (HeLa, human cervical carcinoma cells, NCI-H460, human non-small lung carcinoma cells, HepG2, human hepatoma cells and SW480, human colon adenocarcinoma cells) as measured by methods specified in Example 6.

| | HeLa | NCI-H460 | HepG2 | SW480 |
|---|---|---|---|---|
| Formula I | | | | |
| Timosaponin AIII (TAIII) | 7.47 ± 2.39 | 6.90 ± 0.31 | 7.28 ± 0.56 | 12.21 ± 0.28 |
| Timosaponin AI (TAI) | 44.47 ± 1.15 | 10.17 ± 4.64 | 10.47 ± 4.64 | 12.08 ± 3.83 |
| Asparagoside A (AA) | 65.41 ± 20.86 | 14.14 ± 0.64 | 7.72 ± 2.68 | 15.56 ± 1.96 |
| Timosaponin AV (TAV) | 21.6 ± 5.20 | 19.97 ± 0.71 | 17.42 ± 4.29 | 21.69 ± 2.27 |
| Sarsasapogenin (SSG) | 50.00 ± 2.00 | 19.21 ± 0.45 | 32.62 ± 4.58 | 29.41 ± 5.09 |
| Formula II | | | | |
| Timosaponin BI (TBI) | >100 | >100 | >100 | >100 |
| Timosaponin BII (TBII) | >100 | >100 | >100 | >100 |

The data from Table 5 suggest that timosaponins and SSG treatment inhibit cancer cell growth.

Figure 18:
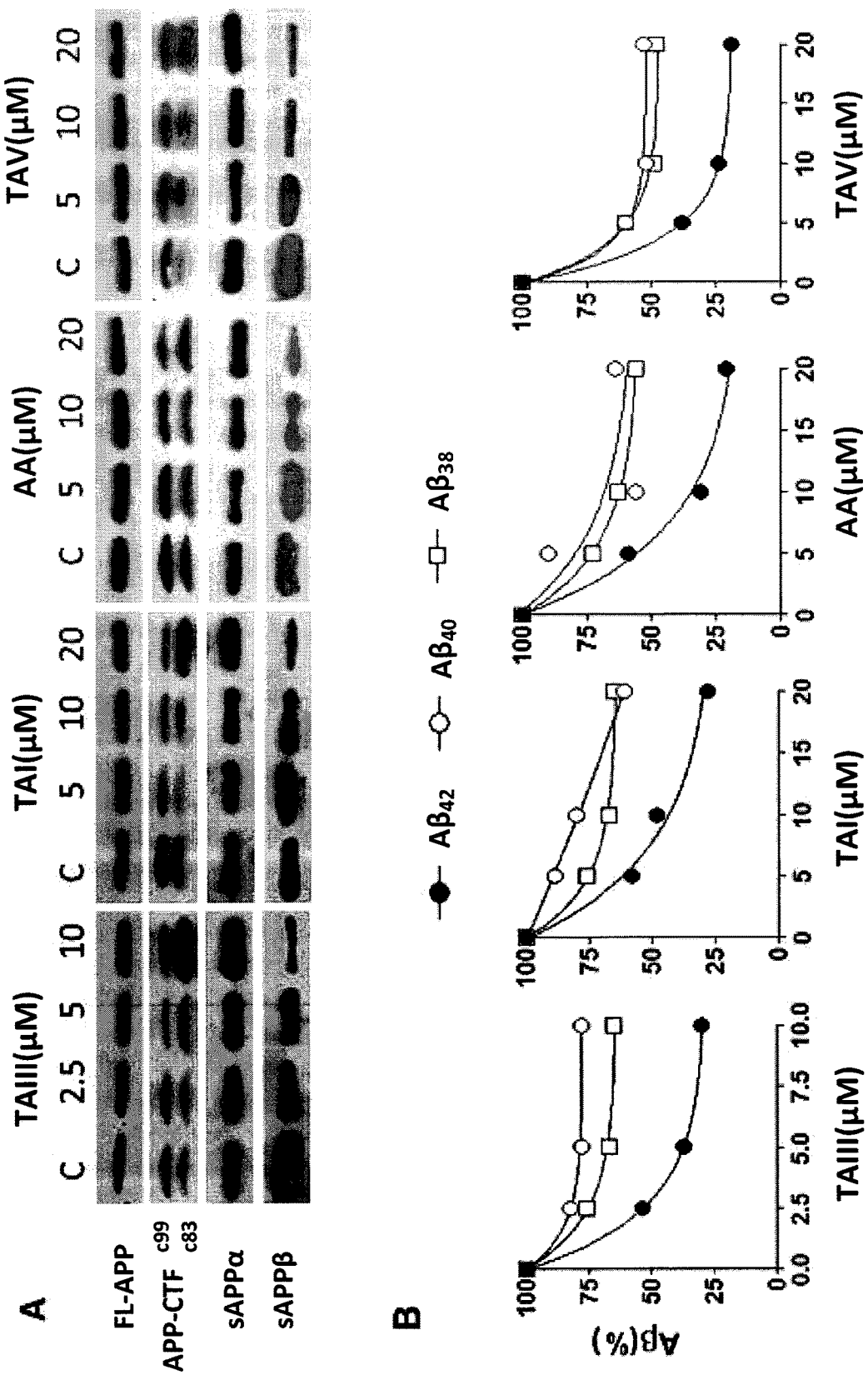
FIG. 18 depicts the effects of timosaponins on the APP processing and Aβ profiles in N2A-APPswe cells.

FIG. 18 shows the effects of timosaponins on the APP processing and Aβ profiles in N2A-APPswe cells. Cells were treated with various concentrations of (TAIII/TAI/AA/TAV) and DMSO vehicle (C) for 18 hr. In part A of FIG. 18, the expression of full length (FL) and CTF (c99 and c83) in cell lysates and secreted APP (sAPPα and sAPPβ) in the conditioned medium were examined by immunoblot using methods specified in Example 6. In part B of FIG. 18, the profiles of Aβ$_{42}$, Aβ$_{40}$ and Aβ$_{38}$ in the conditioned medium were determined by ELISA using methods specified in Example 5.

The data from FIG. 18 suggest that Timosaponins (TAIII, TAI, AA and TAV) preferentially lower Aβ$_{42}$ production.

Figure 19:
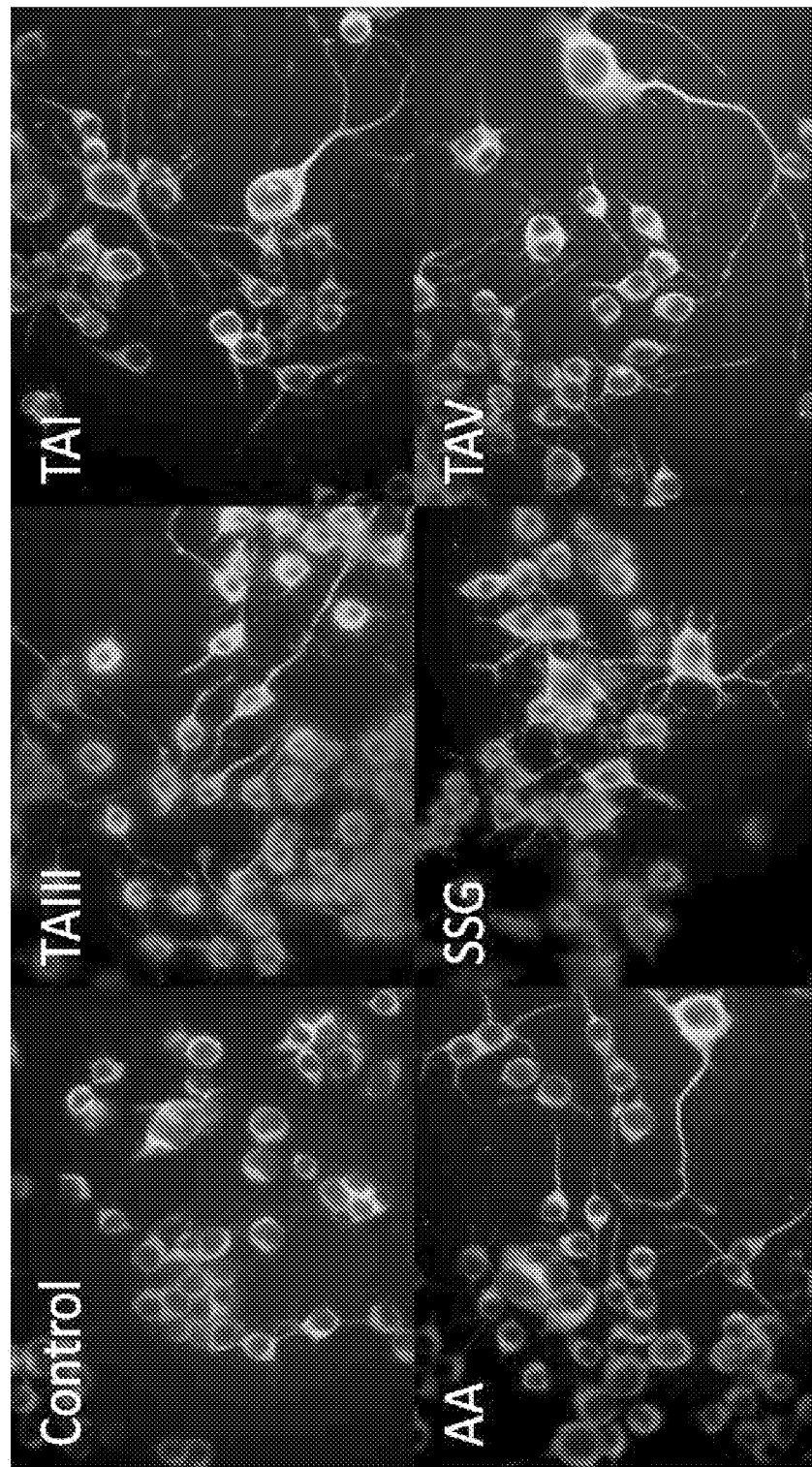
FIG. 19 depicts the effect of timosaponins on neurite outgrowth of Neuro-2A cells.

FIG. 19 shows the effect of timosaponins on neurite outgrowth of Neuro-2A cells. Cells were treated with DMSO (Control), TAIII (5 µM), TAI (10 µM), AA (10 µM), TAV (10 µM) and SSG (25 µM) for 18 hr, stained with monoclonal antibody raised against type III β-tubulin and examined by fluorescence microscopy using methods specified in Example 8.

The data from FIG. 19 suggest that treatment with Timosaponins (TAIII, TAI, AA) and SSG resulted in significant extension and branching of neurites.

Figure 20:
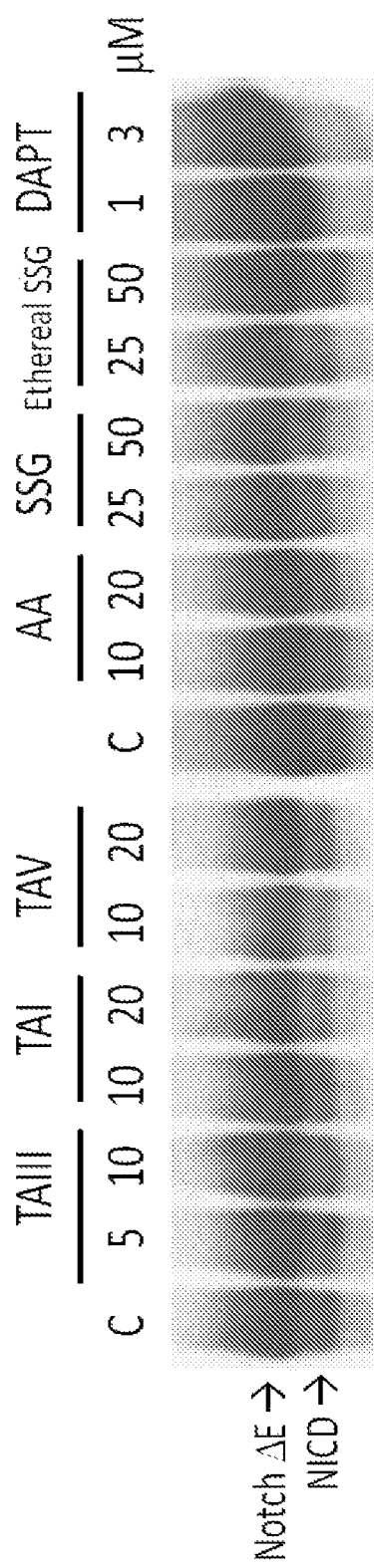
FIG. 20 depicts the effect of timosaponins on Notch cleavage by γ-secretase.

FIG. 20 shows the effect of timosaponins on Notch cleavage by γ-secretase. N2A-APPswe cells were transfected with myc-tagged NotchΔE construct, which was constitutively cleaved by γ-secretase to generate NICD. Cells were then treated with indicated concentrations of timosaponins or DAPT (as positive control for γ-secretase inhibition) for 18 hr and the expression of NotchΔE and NICD were examined by immunoblot analysis using methods specified in Example 6.

The data from FIG. 20 suggest that treatment of cells with the timosaponins, SSG and Ethereal SSG added at concentrations that effectively lower Aβ levels did not affect the Notch processing, indicating the specific effects of timosaponins on APP cleavage.

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A compound of Formula I:

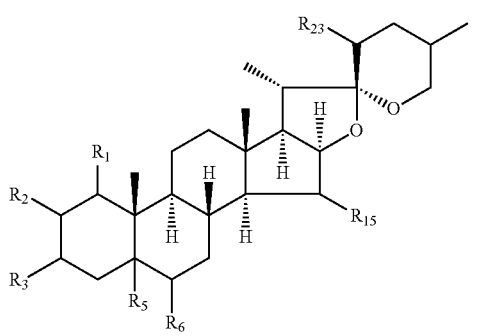

(I)

or a single enantiomer, a mixture of an enantiomeric pair, an individual diastereomer, or a mixture of diastereomers; or a pharmaceutically acceptable salt, solvate, or prodrug thereof, wherein:
  each of $R_1$, $R_2$, $R_{15}$, and $R_{23}$ is independently H, OH, oxo, O-acyl, halo, O-alkyl, $OSO_3H$, $OSO_3Na$, $N_3$, $NH_2$, NHR, NRR', $NHSO_2R$, SR, SOR, $SO_2R$, $OPO_3H_2$, $OPO_3HNa$, $OPO_3Na_2$, O-monosaccharide, O-disaccharide or O-oligosaccharide;
  $R_3$ is O-alkyl;
    wherein the alkyl in $R^3$ is substituted by —C(O)OR$_a$ wherein R$_a$ is hydrogen, or $C_{3-20}$-alkyl; or
    wherein the alkyl in $R^3$ is substituted by —C(O)NR$^b$R$^c$, and wherein R$^b$ and R$^c$ are each independently hydrogen and alkyl, wherein the alkyl is optionally substituted with heterocyclyl which is optionally substituted with one or more —OR$_a$ substituents where R$_a$ is hydrogen or alkyl; and
  each of $R_5$ and $R_6$ is independently H, OH, O-acyl, halo, $OSO_3H$, O-alkyl, $OSO_3H$, $OSO_3Na$, $N_3$, $NH_2$, NHR, NRR', $NHS_2R$, SR, SOR, $SO_2R$, $OPO_3H_2$, $OPO_3HNa$, $OPO_3Na_2$, epoxy, O-monosaccharide, O-disaccharide or O-oligosaccharide, or $R_5$ and $R_6$ together form a double bond,
  where each of R and R' independently is alkyl, aryl, arylalkyl, alkaryl, heteroaryl, alkenyl, alkynyl, cycloalkyl, or heterocyclyl;
  wherein each monosaccharide in $R_1$, $R_2$, $R_{15}$, $R_{23}$, $R_5$, and $R_6$ is independently glucose, fructose, galactose, xylose, ribose, or mannose;
  wherein each disaccharide in $R_1$, $R_2$, $R_{15}$, $R_{23}$, $R_5$, and $R_6$ is independently sucrose, lactose, maltose, trehalose, or cellobiose; and
  wherein each oligosaccharide in $R_1$, $R_2$, $R_{15}$, $R_{23}$, $R_5$, and $R_6$ is independently starch, glycogen, cellulose, chitin, and combinations thereof.

2. The compound of claim 1, wherein each of $R_5$ and $R_6$ is hydrogen; or a single enantiomer, a mixture of an enantiomeric pair, an individual diastereomer, or a mixture of diastereomers; or a pharmaceutically acceptable salt thereof.

3. A pharmaceutical composition comprising the compound of claim 1 or a single enantiomer, a mixture of an enantiomeric pair, an individual diastereomer, or a mixture of diastereomers; or a pharmaceutically acceptable salt thereof; and
  one or more pharmaceutically acceptable carriers.

4. The pharmaceutical composition of claim 3, wherein the composition is formulated as an oral, parenteral, or intravenous dosage form.

5. The pharmaceutical composition of claim 3, wherein the pharmaceutical composition further comprises a therapeutic agent which is an acetyl cholinesterase inhibitor, an N-methyl-D-aspartate receptor antagonist, Donepezil (Aricept™), ENA-713 (Exelon™), Galantamine (Reminyl™) Memantine (Namenda™) Tacrine (Cognex™), Risperidone (Risperidol™), a serotonin reuptake inhibitor (sris), a benzodiazepine, Ginkgo biloba extract, alpha-tocopherol (vitamin E), melatonin, docosahexanoic acid (DHA)/omega-3 fatty acid, or a combination thereof.

6. The compound of claim 1, wherein the alkyl in $R_3$ is methyl or ethyl; and wherein the methyl or ethyl is substituted by —C(O)OR$_a$ where R$_a$ is hydrogen or $C_{3-20}$-alkyl; or a single enantiomer, a mixture of an enantiomeric pair, an individual diastereomer, or a mixture of diastereomers; or a pharmaceutically acceptable salt thereof.

7. The compound of claim 6, wherein each of $R_1$, $R_2$, $R_5$, $R_6$, $R_{15}$, and $R_{23}$ is H; or a single enantiomer, a mixture of an enantiomeric pair, an individual diastereomer, or a mixture of diastereomers; or a pharmaceutically acceptable salt thereof.

8. The compound of claim 1, wherein each of $R_1$, $R_2$, $R_5$, $R_6$, $R_{15}$, and $R_{23}$ is H; or a single enantiomer, a mixture of an enantiomeric pair, an individual diastereomer, or a mixture of diastereomers; or a pharmaceutically acceptable salt thereof.

9. The compound of claim 1, wherein
each of $R_1$, $R_2$, $R_{15}$, and $R_{23}$ is H; and
each of $R_5$ and $R_6$ is H, or $R_5$ and $R_6$ together form a double bond; or a single enantiomer, a mixture of an enantiomeric pair, an individual diastereomer, or a mixture of diastereomers; or a pharmaceutically acceptable salt thereof.

10. The compound of claim 1

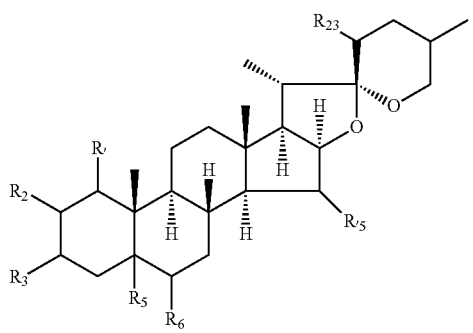

or a single enantiomer, a mixture of an enantiomeric pair, an individual diastereomer, or a mixture of diastereomers; or a pharmaceutically acceptable salt thereof, wherein:

$R_5$ and $R_6$ together form a double bond.

11. The pharmaceutical composition of claim 3, wherein the alkyl in $R_3$ is methyl or ethyl; wherein the methyl or ethyl is substituted by —C(O)OR$_a$ where R$_a$ is hydrogen; or a single enantiomer, a mixture of an enantiomeric pair, an individual diastereomer, or a mixture of diastereomers; or a pharmaceutically acceptable salt thereof.

12. The pharmaceutical composition of claim 11, wherein each of $R_1$, $R_2$, $R_5$, $R_6$, $R_{15}$, and $R_{23}$ is H; or a single enantiomer, a mixture of an enantiomeric pair, an individual diastereomer, or a mixture of diastereomers; or a pharmaceutically acceptable salt thereof.

13. The pharmaceutical composition of claim 3, wherein
each of $R_1$, $R_2$, $R_{15}$, and $R_{23}$ is H; and
each of $R_5$ and $R_6$ is H, or $R_5$ and $R_6$ together form a double bond; or a single enantiomer, a mixture of an enantiomeric pair, an individual diastereomer, or a mixture of diastereomers; or a pharmaceutically acceptable salt thereof.

* * * * *